US011254714B2

United States Patent
Cho et al.

(10) Patent No.: US 11,254,714 B2
(45) Date of Patent: Feb. 22, 2022

(54) **METHOD FOR INHIBITING, IMPROVING, OR PREVENTING AGING USING RECOMBINANT FUSION PROTEIN OF PATHOGENIC ANTIGEN PROTEIN AND FLAGELLIN OF *VIBRIO VULNIFICUS***

(71) Applicant: MEDISPAN CO., LTD., Seongnam-si (KR)

(72) Inventors: Kyung A. Cho, Gwangju (KR); Jae Sung Lim, Gwangju (KR); Joon Haeng Rhee, Gwangju (KR)

(73) Assignee: MEDISPAN CO., LTD., Gyeonggi-do (KR)

( * ) Notice: Subject to any disclaimer, the term of this patent is extended or adjusted under 35 U.S.C. 154(b) by 0 days.

(21) Appl. No.: 16/197,751

(22) Filed: Nov. 21, 2018

(65) Prior Publication Data

US 2019/0077838 A1    Mar. 14, 2019

Related U.S. Application Data

(60) Continuation-in-part of application No. 15/801,467, filed on Nov. 2, 2017, now Pat. No. 10,407,471,
(Continued)

(30) Foreign Application Priority Data

Nov. 30, 2012    (KR) .................. 10-2012-0138234

(51) Int. Cl.
*C07K 14/315* (2006.01)
*C07K 14/28* (2006.01)
(Continued)

(52) U.S. Cl.
CPC ........ *C07K 14/3156* (2013.01); *A61K 38/164* (2013.01); *A61K 39/092* (2013.01);
(Continued)

(58) Field of Classification Search
CPC ............ C07K 2319/00; C07K 14/3156; C07K 14/28; A61K 2039/58; A61K 39/107;
(Continued)

(56) References Cited

U.S. PATENT DOCUMENTS

| 10,407,471 B2 | 9/2019 | Cho et al. | |
| 2010/0291109 A1* | 11/2010 | Kedl | .................. A61K 39/0008 424/173.1 |

(Continued)

FOREIGN PATENT DOCUMENTS

| KR | 2006-0118737 A | 11/2006 |
| KR | 10-0795839 B1 | 1/2008 |

(Continued)

OTHER PUBLICATIONS

Of Nguyen et al., (Vaccine. Aug. 5, 2011;29(34):5731-9. Epub Jun. 13, 2011) (Year: 2011).*

(Continued)

*Primary Examiner* — Jana A Hines
(74) *Attorney, Agent, or Firm* — Clark & Elbing LLP; Susan M. Michaud

(57) ABSTRACT

The present invention relates to a method for inhibiting, improving, or preventing aging, comprising administering to a subject in need thereof a composition comprising a recombinant protein of flagellin, which is the constituent of *Vibrio vulnificus* flagella, fused with a pathogenic protein antigen, which is pneumococcal surface protein A (PsaA) of *Streptococcus pneumonia*. According to the present invention, the recombinant protein of the present invention can improve external and internal aging-related malfunctions and enhance immunity. Also, the composition of the present invention can easily perform immunization through mucosal administration.

9 Claims, 51 Drawing Sheets

Figure 1:
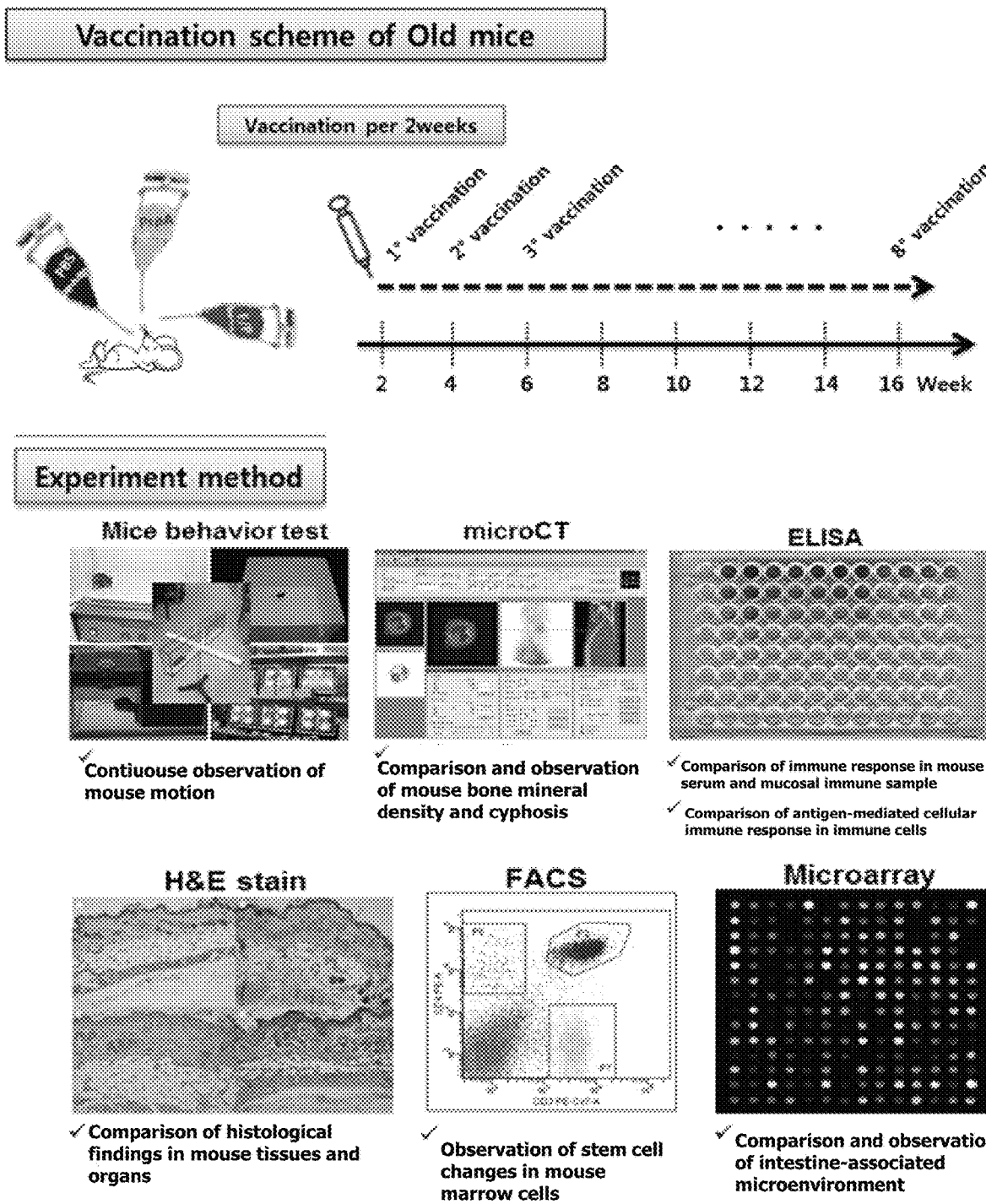

Specification includes a Sequence Listing.

Related U.S. Application Data which is a division of application No. 14/764,466, filed as application No. PCT/KR2013/002547 on Mar. 27, 2013, now abandoned.

(51) Int. Cl.

| *A61K 39/02* | (2006.01) |
|---|---|
| *A61K 39/09* | (2006.01) |
| *A61K 38/16* | (2006.01) |
| *A61P 31/04* | (2006.01) |
| *C12N 15/62* | (2006.01) |
| *A61K 39/00* | (2006.01) |

(52) U.S. Cl.
CPC ............ *A61K 39/107* (2013.01); *A61P 31/04* (2018.01); *C07K 14/28* (2013.01); *C12N 15/62* (2013.01); *A61K 2039/543* (2013.01); *A61K 2039/58* (2013.01); *A61K 2039/6068* (2013.01); *C07K 2319/00* (2013.01)

(58) Field of Classification Search
CPC ............ A61K 38/164; A61K 2039/543; A61K 2039/6068; A61K 39/092; C12N 15/62; A61P 31/04

See application file for complete search history.

(56) References Cited

U.S. PATENT DOCUMENTS

| 2016/0083437 A1 | 3/2016 | Cho et al. |
| 2018/0118792 A1 | 5/2018 | Cho et al. |

FOREIGN PATENT DOCUMENTS

| KR | 20100114620 | * | 10/2010 | ............ A61K 39/106 |
| KR | 20100114620 A | | 10/2010 | |
| KR | 10-1130884 B1 | | 4/2012 | |
| WO | WO-2005/070455 A1 | | 8/2005 | |
| WO | WO-2007/098371 A2 | | 8/2007 | |
| WO | WO-2014/084456 A1 | | 6/2014 | |

OTHER PUBLICATIONS

Richardson et al., Measures of Healthspan as Indices of Aging Mice. J Gerontol A Biol Sci Med Sci. Apr. 2016; 71(4): 427-430 published online Aug. 22, 2015. (Year: 2015).*

Reich et al., (Gastroenterol Hepatol (N Y). Sep. 2016; 12(9): 540-546). (Year: 2016).*

Baheti et al., "Cataract surgery in patients with history of uveitis," Saudi J Ophthalmol. 26(1):55-60 (2012).

International Search Report for PCT International Application No. PCT/KR2013/002547, dated Jun. 14, 2013 (8 pages).

Kumar et al., "Topical flagellin protects the injured corneas from Pseudomonas aeruginosa infection," available in PMC Nov. 1, 2011, published in final edited form as: Microbes Infect. 12(12-13):978-89 (2010) (19 pages).

Lee et al., "A bacterial flagellin, *Vibrio vulnificus* FlaB, has a strong mucosal adjuvant activity to induce protective immunity," Infect Immun. 74(1):694-702 (2006).

Lotti et al., "Cataract as a complication of severe microbial keratitis," Eye (Lond). 6(Pt 4):400-3 (1992).

Nguyen et al., "Intranasal immunization with recombinant PspA fused with a flagellin enhances cross-protective immunity against *Streptococcus pneumoniae* infection in mice," Vaccine. 29(34):5731-9 (2011).

Komori, "Animal models for osteoporosis," Eur J Pharmacol. 759:287-94 (2015).

Robertson et al., "Animal model of aluminum-induced osteomalacia: role of chronic renal failure," Kidney Int. 23(2):327-35 (1983).

Scholz-Ahrens et al., "Modulation of vitamin D status and dietary calcium affects bone mineral density and mineral metabolism in Göttingen minipigs," ISRN Rheumatol. 2013:460512 (2013) (12 pages).

U.S. Appl. No. 16/524,719, Cho et al.

Etienne-Mesmin et al., "Hepatocyte toll-like receptor 5 promotes bacterial clearance and protects mice against high-fat diet-induced liver disease," Cell. Mol. Gastroenterol. Hepatol. 2(5):584-604 (2016).

Singh et al., "Proneness of TLR5 deficient mice to develop colitis is microbiota dependent," Gut Microbes 6(4):279-283 (2015).

Tsukahara et al., "The relationship between wrinkle depth and dermal thickness in the forehead and lateral canthal region," Arch. Dermatol. 147(7):822-828 (2011).

Vijay-Kumar et al., "Deletion of TLR5 results in spontaneous colitis in mice," J. Clin. Invest. 117(12):3909-3921 (2007).

* cited by examiner

Fig. 6

| Mice No. | | Cellularity | Cell No. (/HPF) | | | Dysplastic feature | | | CD34 count/HPF |
|---|---|---|---|---|---|---|---|---|---|
| | | | Megakaryocytes | Myeloid | erythroid | Megakaryocytes | Myeloid | erythroid | |
| 1 | O-control (22 months) | 65% | 3 | preserved | preserved | (-) | (-) | (-) | 4~5 |
| 2 | O-control (25 months) | 95% | 4 | preserved | preserved | 1+ | (-) | (-) | 3~4 |
| 3 | O-PBS (1)(25 months) | 90% | 6 | preserved | preserved | (-) | (-) | (-) | 6~7 |
| 4 | O-PBS (2)(25 months) | 60% | 2 | preserved | preserved | 1+ | (-) | (-) | 6~7 |
| 5 | O-PspA(1)(25months) | 90% | 2 | preserved | preserved | (-) | (-) | (-) | 7~8 |
| 6 | O-PspA(2)(24months) | 80% | 5 | preserved | preserved | (-) | (-) | (-) | 3~4 |
| 7 | O-PspA(3)(24months) | 95% | 6 | preserved | preserved | (-) | (-) | (-) | 8~9 |
| 8 | O-FP(1)(24months) | 80% | 10 | preserved | preserved | 2+ | (-) | (-) | 10~12 |
| 9 | O-FP(2)(25months) | 90% | 5 | preserved | preserved | (-) | (-) | (-) | 10~12 |
| 10 | O-FP(3)(25months) | 80% | 6 | preserved | preserved | 1+ | (-) | (-) | 12~14 |

FP; FlaB-PspA conjugated proteins

Fig. 8
Spine
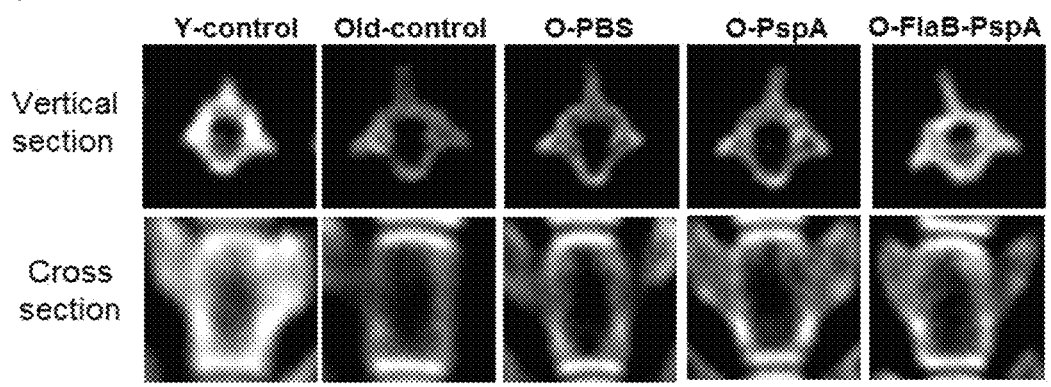
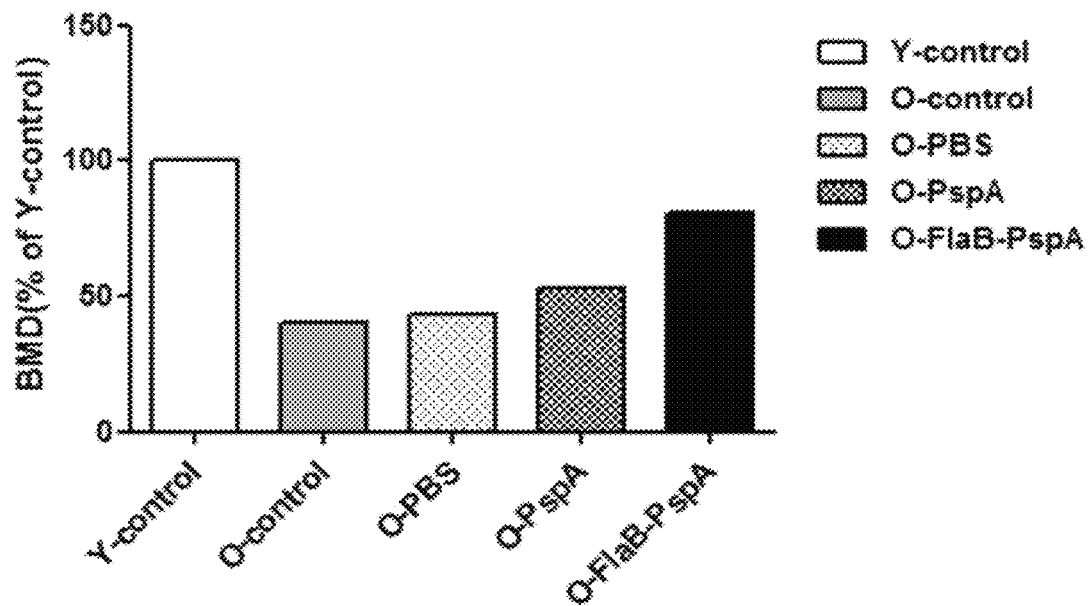

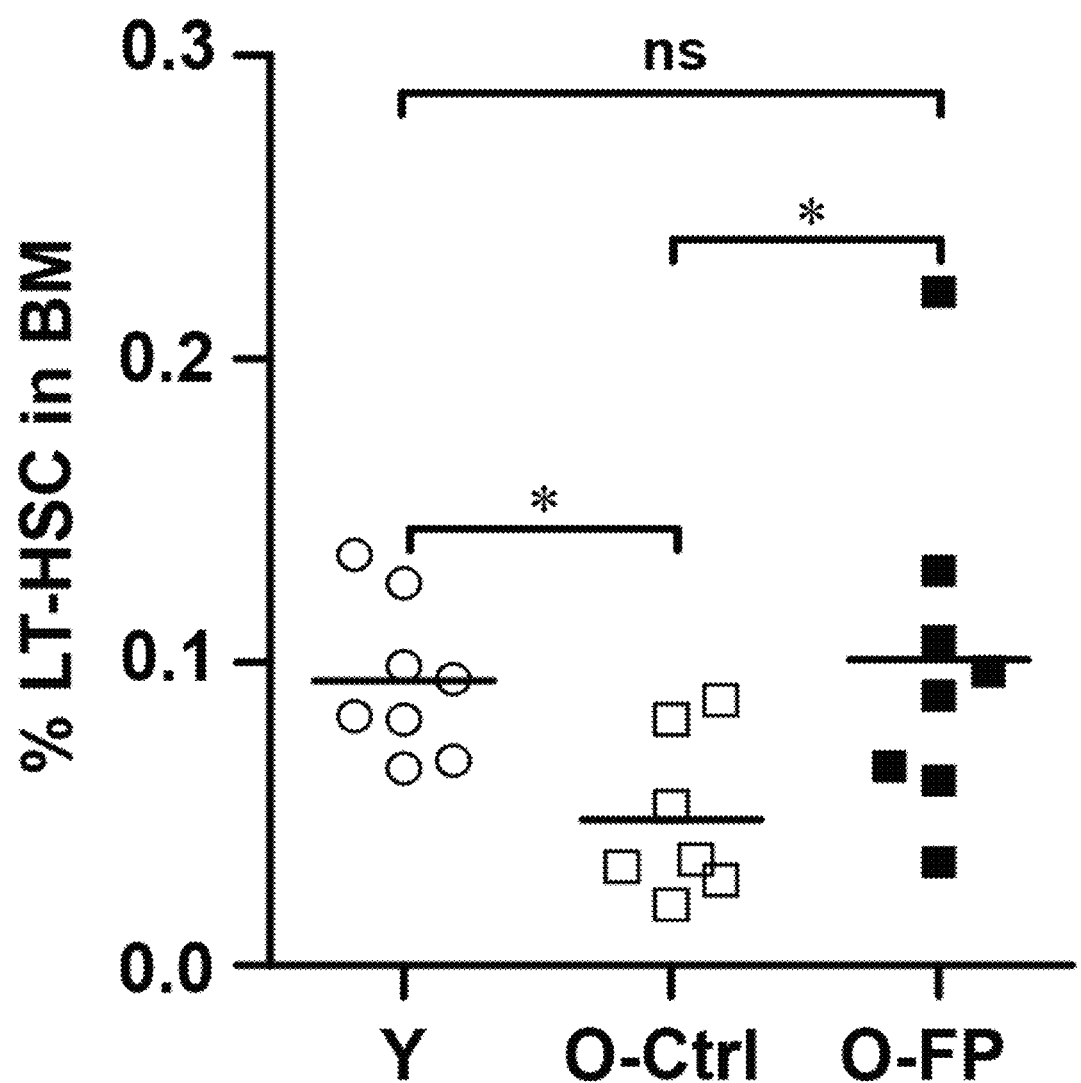

Fig. 11A
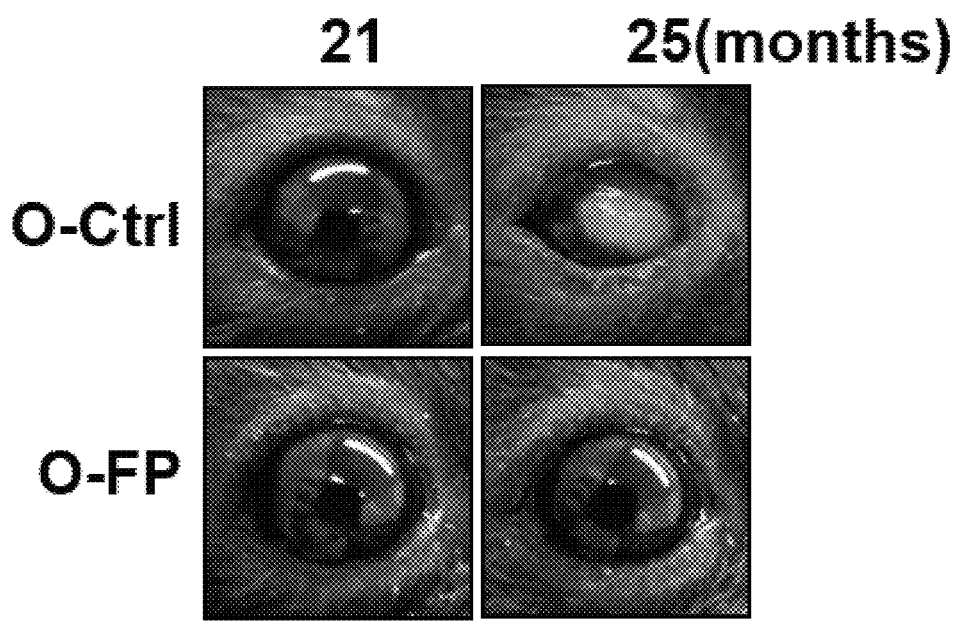
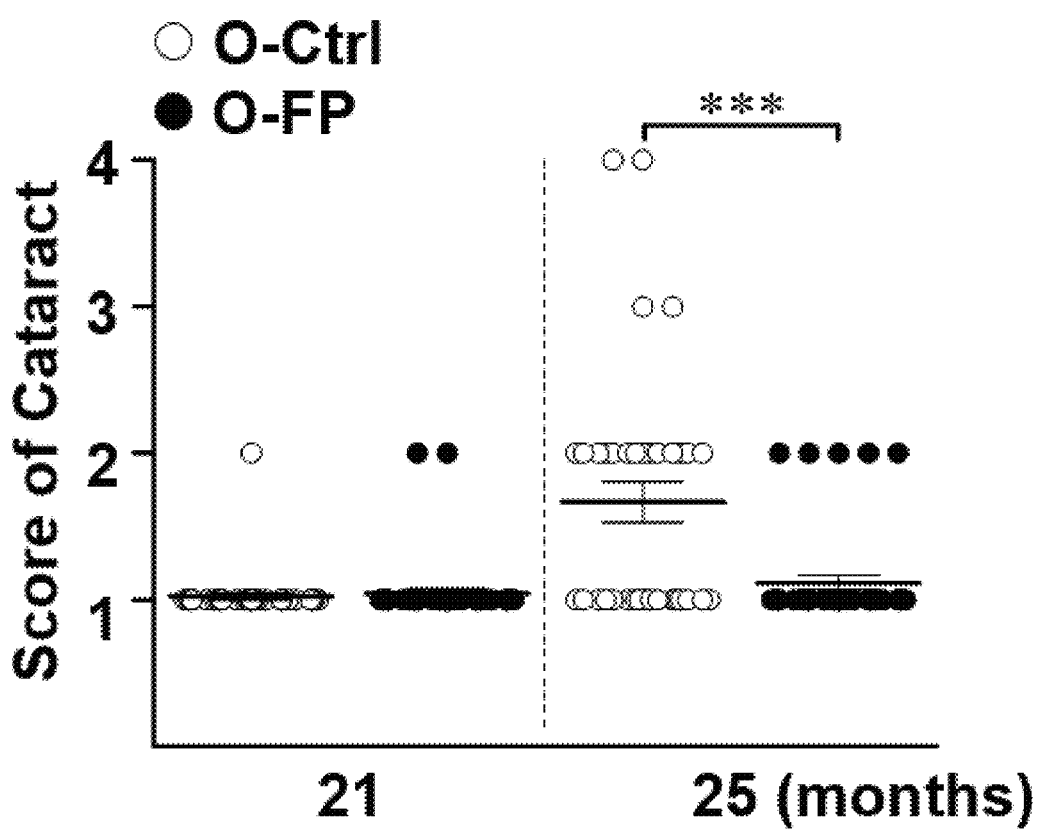

Fig. 11B
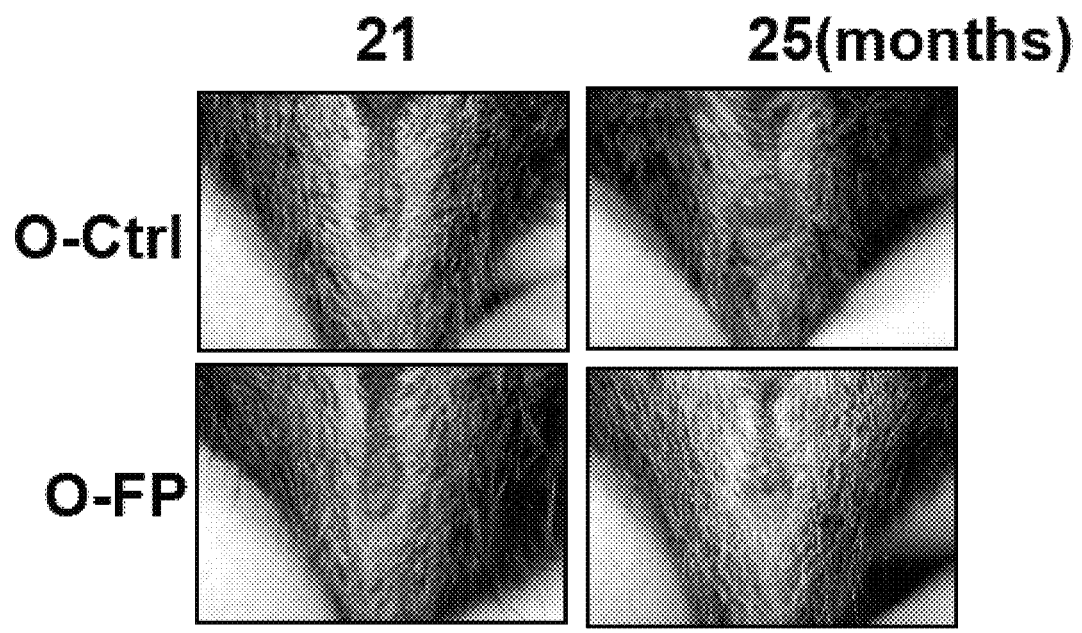
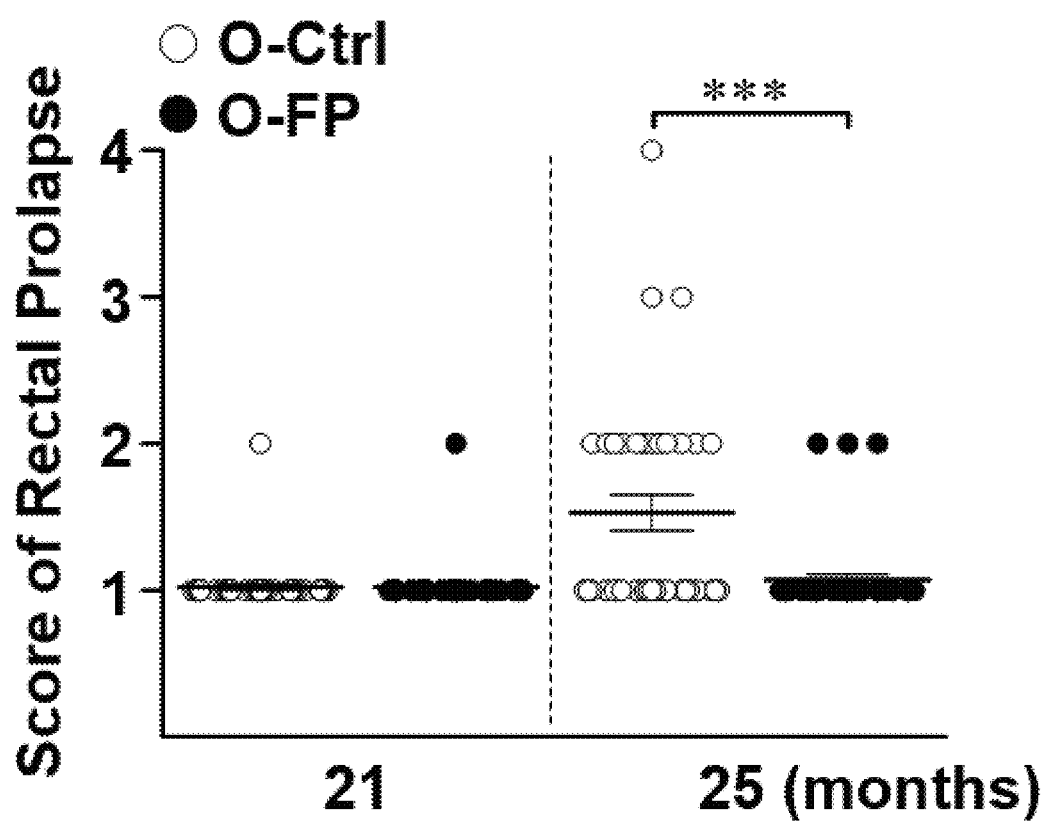

Fig. 11C
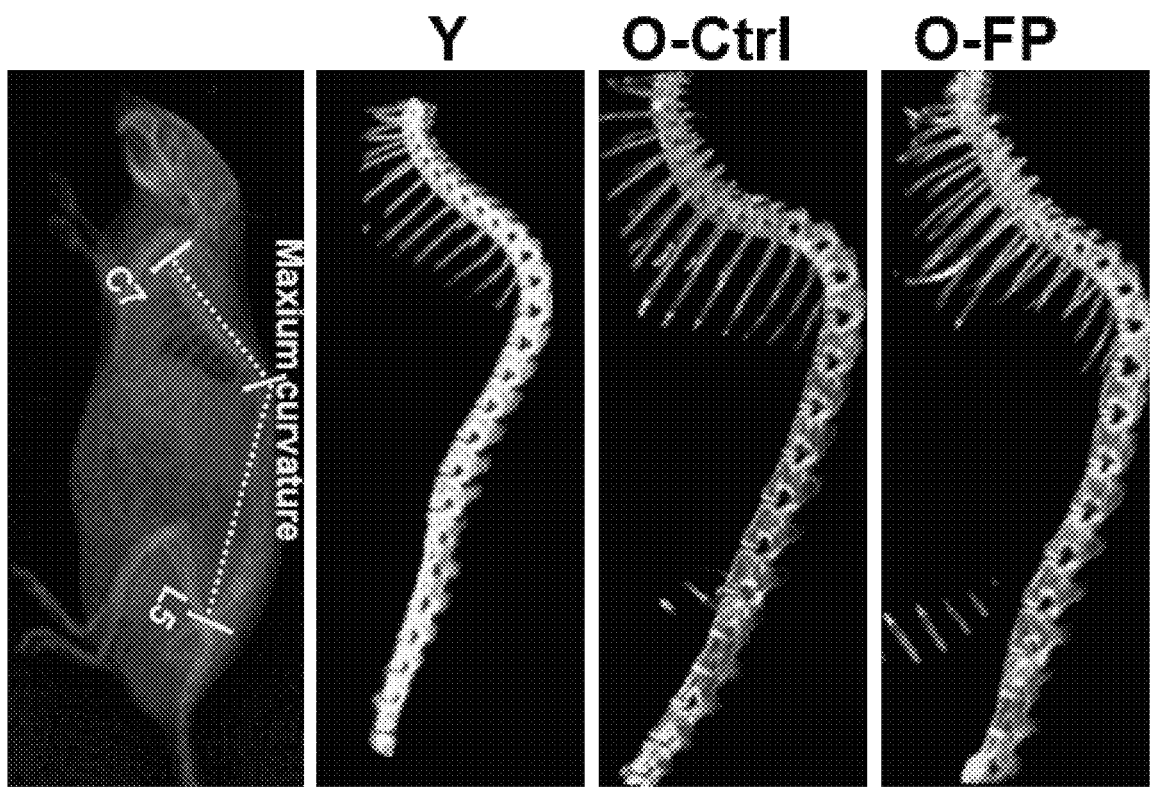
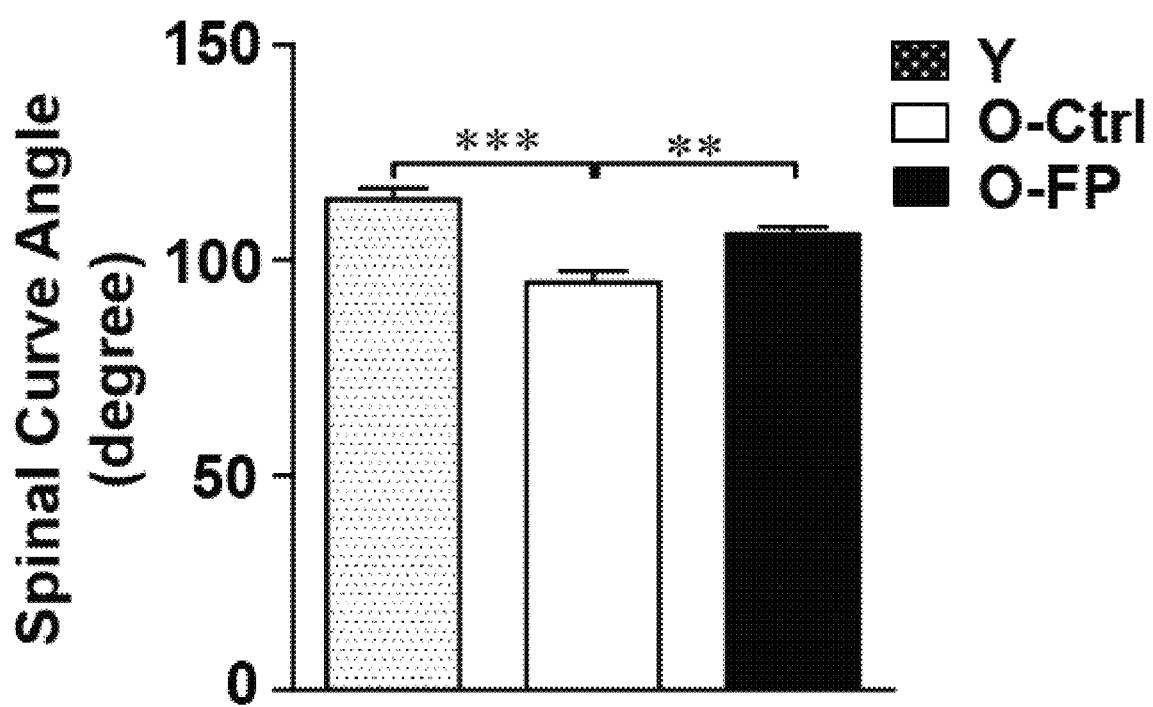

Fig. 14C

Fig. 15A

TLR5 binding site

```
         89                                                    98
FlaB WT   L   Q   R   M   R   D   L   S   L   Q
          cta caa cgt atg cgt gac cta tct cta caa FlaB SDM  L   Q   R   A   R   D   A   S   L   Q
          cta caa cgt gcg cgt gac gca tct cta caa
```

Fig. 16D
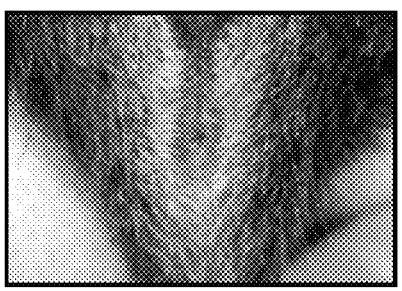
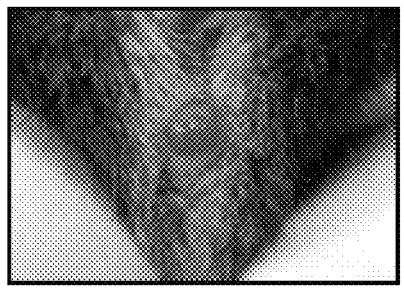
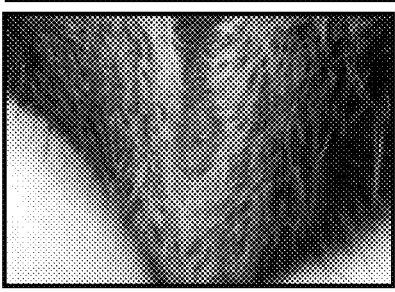
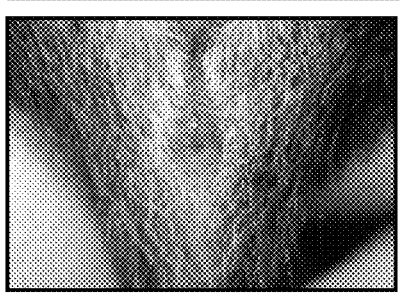
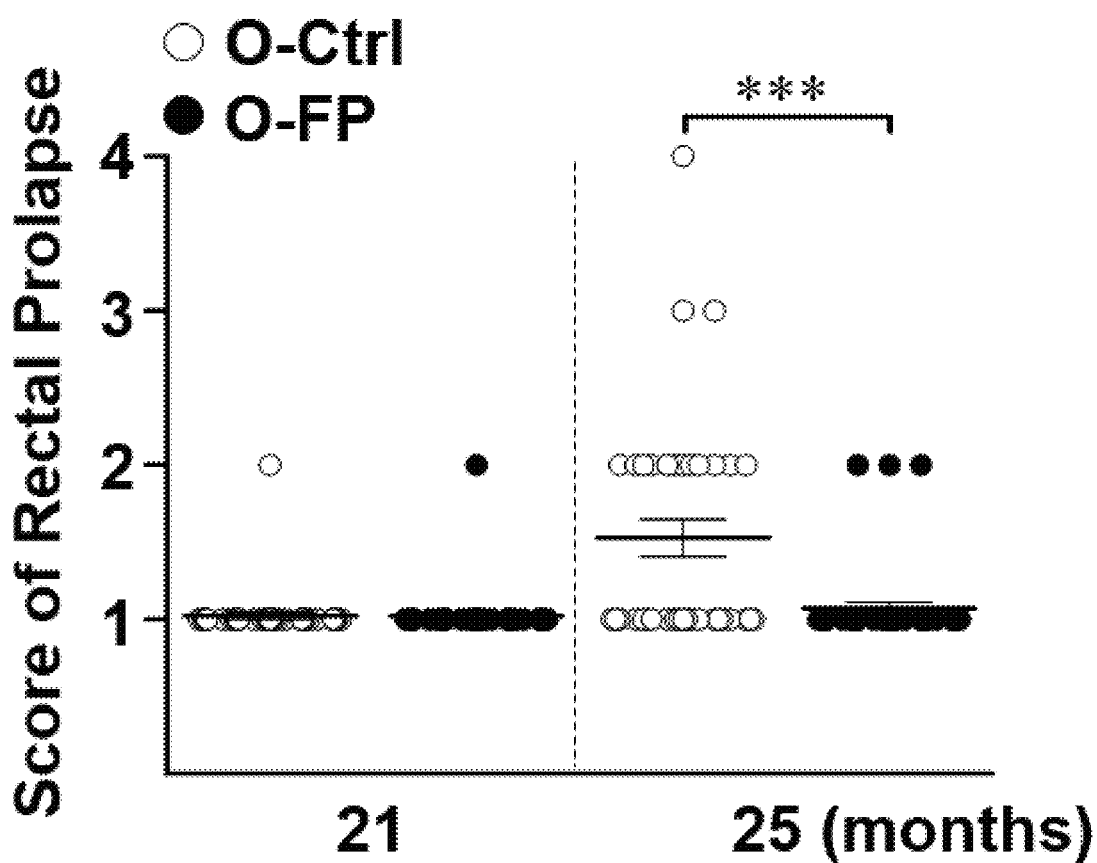

METHOD FOR INHIBITING, IMPROVING, OR PREVENTING AGING USING RECOMBINANT FUSION PROTEIN OF PATHOGENIC ANTIGEN PROTEIN AND FLAGELLIN OF *VIBRIO VULNIFICUS*

TECHNICAL FIELD

The present invention was supported by the National Research Foundation of Korea (NRF) grant funded by the Korea government (MIST), under Project No. NRF-2017R1E1A2A02081815, which was conducted in the program titled "X-project" in the project named "Development of anti-aging vaccine for preventing of aging-related disease" by the Chonnam National University under the management of the National Research Foundation of Korea, from Nov. 1, 2017 to Oct. 31, 2018.

Furthermore, the present invention was supported by the National Research Foundation of Korea (NRF) grant funded by the Korea government (MIST), under Project No. NRF-2017R1E1A1A01074674, which was conducted in the program titled "Strategic project" in the project named "Development of new senolytic agents from natural products and mechanism studies" by the Seoul National University & Chonnam National University under the management of the National Research Foundation of Korea, from Nov. 1, 2017 to Oct. 31, 2021.

Furthermore, the present invention was supported by the National Research Foundation of Korea (NRF) grant funded by the Korea government (MIST), under Project No. NRF-2018R1D1A1B051207, which was conducted in the program titled "Individual Basic Science&Engineering Research Program—General Individual" in the project named "The study of anti-aging effect via regulation of TLR5 signal transduction by the mucosal immunological activator FlaB/PspA" by the Chonnaml National University under the management of the National Research Foundation of Korea, from Jun. 1, 2018 to May 31, 2021.

Furthermore, the present invention was supported by the National Research Foundation of Korea (NRF) grant funded by the Korea government (MSIT), under Project No. 2018R1A5A2024181.

The present invention relates to a method for inhibiting, improving, or preventing aging using the composition comprising a recombinant protein of flagellin, which is the constituent of *Vibrio vulnificus* flagella and an agonist of a toll-like receptor 5 (TLR-5), fused with a pathogenic antigen.

BACKGROUND ART

Humans are facing various problems not seen before due to the advent of an aging society caused by a prolonged average life span. In socio-economic aspects, the elderly sustenance allowance per head is expected to increase due to the increase in the elderly population and the reduction in the productive age population, and the interest in the improvement of the quality of life of the elderly is also a growing trend. As the social demands for the healthy and happy life of the elderly increase as described above, studies on the change in aging-related disease aspect and prevention of aging-related diseases are under active progress.

The aging process causes a wide variety of changes. Various changes appear, including reduced functions of respective main tissues, food intake and digestive disorders, reduced brain functions including defective memory, and reduced cardiovascular functions, as well as various appearance changes, such as skin wrinkles, hair decoloration, spine curving, and the change in motion. Moreover, these changes induce the reduction of functions and diseases of the respective tissues, and therefore, it is very important to understand causes of the reduction of external and internal functions due to aging and develop techniques of regulating the functions.

Besides, one of the large changes in functions due to aging is the reduction in immune function. This is called immunosenescence. When pathogens invade a host, the host defection action is made by two immune systems, an innate immune system and an adaptive immune system. Of these, the innate immune system is activated immediately after infection, to promptly regulate infecting pathogens, and takes charge of the initial infection until the adaptive immune system is activated. In this innate immune system, a receptor recognizing "pathogen associated molecular patterns (PAMPs) existing in the pathogens is called "pattern recognition receptors (PRRs), and these receptors are called toll-like receptors in a mammal. So far, 13 kinds of TLRs have been found, and studies on agonists of the respective TLRs have been actively conducted (Shizuo Akira et al, Cell, Pathogen Recognition and Innate Immunity, 124(4): 783-801, 2006). PRRs like TLRs exist on the cell surface or in the protoplasm, and have been known to regulate the innate immune response by various stimuli of PAMPs, and further regulate the adaptive immune response. Therefore, the agonists of TLRs may be target materials suitable for the development of various immunomodulators and vaccine adjuvants.

Of studies on aging, the fields that have received the most attention so far are the life span adjustment of aging or functional recovery of aging. Recently, studies on the extension of life span are rapidly increasing through various methods, such as by inhibiting the expression of a particular gene or overexpressing the particular gene in studies using drosophila models or nematodes, restricting diet, or treating with rapamycin. In addition, the interest in the maintenance of functions or recovery of functions, instead of the simple extension of life span, is also a growing trend. However, the regulation of a particular gene referring to the results shown in lower animal models may cause other functional side effects, and thus has a limitation in the application to humans. Moreover, the treatment with a drug, such as rapamycin, may greatly influence the immune function.

DETAILED DESCRIPTION OF THE INVENTION

Technical Problem

The present inventors have endeavored to develop a material capable of preventing, improving, or treating dysfunction due to aging. As a result, the present inventors have confirmed that the expressions of most toll-like receptors are reduced but toll-like receptor-5 is well expressed to keep functions thereof in aging immune cells, and confirmed that, when aged mice are immunized with a recombinant protein of flagellin, which is the constituent of *Vibrio vulnificus* flagella, fused with a pathogenic protein antigen of a pathogen, the immunity of the aged mice is activated and external and internal functions of the aged mice are improved, and thus have completed the present invention.

Therefore, an object of the present invention is to provide a composition for preventing, improving, or treating aging, the composition comprising, as an active ingredient, a recombinant protein of flagellin, which is the constituent of *Vibrio vulnificus* flagella, fused with a pathogenic protein antigen.

Another object of the present invention is to provide a composition for preventing, improving, or treating hair-related disease, the composition comprising the recombinant protein as an active ingredient.

Still another object of the present invention is to provide a composition for preventing, improving, or treating eye-related disease, the composition comprising the recombinant protein as an active ingredient.

Still another object of the present invention is to provide a composition for preventing, improving, or treating bowel disease, the composition comprising the recombinant protein as an active ingredient.

Still another object of the present invention is to provide a composition for preventing, improving, or treating bone disease, the composition comprising the recombinant protein as an active ingredient.

Still another object of the present invention is to provide a method for inhibiting, improving or preventing aging.

Still another object of the present invention is to provide a method for increasing the lifespan of a mammal.

Another object of the present invention is to provide a method for preventing, improving, or treating aging.

Technical Solution

According to an aspect of the present invention, the present invention provides a composition for preventing, improving, or treating aging, the composition comprising, as an active ingredient, a recombinant protein of flagellin, which is the constituent of *Vibrio vulnificus* flagella, fused with a pathogenic protein antigen.

The present inventors have endeavored to develop a material capable of preventing, improving, or treating dysfunction due to aging. As a result, the present inventors have confirmed that the expressions of most toll-like receptors are reduced but toll-like receptor-5 is well expressed to keep functions thereof in aging immune cells, and confirmed that, when aged mice are immunized with a recombinant protein of flagellin, which is the constituent of *Vibrio vulnificus* flagella, fused with a pathogenic protein antigen, the immunity of the aged mice is activated and external and internal functions of the aged mice are improved.

The largest feature of the present invention is to use a recombinant protein of flagellin, which is the constituent of *Vibrio vulnificus* flagella, fused with a pathogenic protein antigen.

As used herein, the term "flagellin" refers to a unit molecule constituting flagella, which are the cilia to determine the mobility of bacteria. The flagellin of the present invention includes all flagellins and their derivatives, which have TLR5 binding domain derived from various strains including *Vibrio*. A conserved TLR5 binding domain of flagellins from Gram-negative and Gram-positive bacteria bind and activate TLR5 (Wan Seok Song et al., Scientific Reports, volume 7, Article number: 40878 (2017)).

According to an embodiment of the present invention, the flagellin of the present invention is flagellin and its derivative that act as a TLR-5 activator of *Vibrio vulnificus*. According to other embodiment of the present invention, the flagellin of the present invention is FlaB, which is the flagellin of *Vibrio vulnificus*.

The largest feature of the present invention is to use a recombinant protein of flagellin, which is the constituent of *Vibrio vulnificus* flagella, fused with a pathogenic protein antigen.

Examples of the pathogenic protein antigen usable herein may include an α-helix domain of surface protein A (PspA) and pneumococcal surface protein A (PsaA) of *Streptococcus pneumonia*; subunit hemagglutinin (HA) and neuraminidase (NA) of influenza virus; and spike (S) protein of severe acute respiratory syndrome virus (SARS virus), but are not limited thereto. According to an embodiment of the present invention, the pathogenic protein antigen is surface protein A (PspA) of *Streptococcus pneumonia*.

According to an embodiment of the present invention, the recombinant protein of the present invention is FlaB-PspA protein having an amino acid sequence of SEQ ID NO: 1.

As used herein, the term "aging" refers to a functional, structural, and biochemical procedure that continuously occurs in a subject from birth until death. The aging occurs in the overall cells and body tissues constituting the subject, and indicates the decrease in the metabolic rate, the increase in diseases, and the deterioration in adaptability, ultimately leading to death in cells and the whole body. For example, examples of aging include external changes, such as the increase in skin wrinkles, the reduction of hair gloss, hair decoloration, hair loss, the thickness reduction of the dermal layer in which hair follicles are present, the reduction in the number of follicles, spine curving, and the reduction in exercising; internal changes, such as the reduction in immune functions and the reduction in functions of main tissues; and the consequent occurrence of diseases of respective tissues, but are not limited thereto.

According to an embodiment of the present invention, the recombinant protein of the present invention enhances immunity. As used herein, the term "enhancing immunity" refers to keeping the immune response or activity of the in vivo immune system at a level of a non-aged control group or enhancing the same to a level of an aged control group. According to another embodiment of the present invention, the recombinant protein of the present invention prevents the reduction of functionality of immune-related organs due to aging or enhances the functionality compared with the aged control group, by increasing the production of secretory globulin A (secretory lgA, slgA) antibody, increasing the frequency of hematopoietic stem cells which are essentially associated with T cell differentiation, preventing thymic involution, or preventing the hypertrophy of mesenteric lymph nodes (MLNs) or spleens.

According to an embodiment of the present invention, the recombinant protein of the present invention prevents, improves, or treats the deteriorations in metabolic functions, functions of skin tissues, functions of intestinal tissues, functions of muscular tissues, brain functions, or cardiovascular functions. According to another embodiment of the present invention, the recombinant protein of the present invention prevents, improves, or treats the deteriorations in metabolic functions, functions of skin tissues, functions of intestinal tissues, or functions of muscular tissues. According to a particular embodiment of the present invention, the recombinant protein of the present invention prevents, improves, or treats the deteriorations in functions of the dermal tissue in which hair follicles are present, functions of large intestine tissues, or functions of muscular tissues.

According to another embodiment of the present invention, the present invention provides a composition for preventing, improving, or treating metabolic disease, the composition comprising the recombinant protein as an active ingredient.

As used herein, the term "metabolic disease" refers to a syndrome in which risk factors, such as obesity, diabetes, hypertriglyceridemia, hypertension, cardiovascular disease, and blood clotting, are shown together. The syndrome per se is not fatal, but has a predisposition to severe diseases, such as diabetes or ischemic cardiovascular diseases, resulting in a great threat to modern people. The syndrome was once called several names, including syndrome X, since the cause of the syndrome was not known, but recently, the syndrome was officially named metabolic syndrome or insulin resistance syndrome through adult treatment program III (ATP III) established by the World Health Organization and the US National Institutes of Health. According to an embodiment of the present invention, the metabolic disease of the present invention is obesity.

According to another embodiment of the present invention, the present invention provides a composition for preventing, improving, or treating hair-related disease, the composition comprising the recombinant protein as an active ingredient.

Examples of the hair-related disease which can be prevented, improved, or treated by the composition of the present invention include the reduction of hair gloss, hair decoloration, hair loss, the thickness reduction of the dermal layer in which hair follicles are present, the reduction in the number of follicles, and the like, but are not limited thereto.

According to still another embodiment of the present invention, the present invention provides a composition for preventing, improving, or treating bowel disease, the composition comprising the recombinant protein as an active ingredient.

Examples of the bowel disease which can be prevented, improved, or treated by the composition of the present invention include irritable bowel syndrome (IBS), uncontrolled diarrhea-associated irritable bowel syndrome (dIBS), Crohn's disease, traveler's diarrhea, ulcerative colitis, enteritis, small intestine bacterial overgrowth, chronic pancreatitis, pancreatic insufficiency, colitis, diverticular disease, hepatic encephalopathy, and hernia, but are not limited thereto. According to an embodiment of the present invention, the bowel disease of the present invention is enteritis or hernia. According to another embodiment of the present invention, the bowel disease of the present invention is colitis or hernia.

According to still another embodiment of the present invention, the present invention provides a composition for preventing, improving, or treating bone disease, the composition comprising the recombinant protein as an active ingredient.

Examples of the bone diseases which can be prevented or treated by the compositions of the present invention include osteoporosis, scoliosis, osteomalacia, rickets, bone metastasis of cancer cells, bone damage caused by bone metastases of cancer cells, osteolysis caused by bone metastases of cancer cells, fibrous dysplasia, aplastic bone disease, metabolic bone disease, rheumatoid arthritis, osteoarthritis, degenerative arthritis, and disc disease, but are not limited thereto. According to an embodiment of the present invention, the bone-related disease of the present invention is osteomalacia, metabolic bone disease, rheumatoid arthritis, osteoarthritis, or degenerative arthritis. According to another embodiment of the present invention, the bone disease of the present invention is osteoporosis or osteomalacia.

The composition for preventing, improving, or treating the foregoing diseases of the present invention contains the foregoing recombinant protein as an active ingredient, and thus descriptions of overlapping contents with the recombinant protein are omitted to avoid excessive complication of the specification due to repetitive descriptions thereof.

The composition of the present invention may be provided as a pharmaceutical composition.

According to an embodiment of the present invention, the composition of the present invention is a pharmaceutical composition comprising (a) a pharmaceutically effective amount of the recombinant protein any one of the recombinant proteins of the present invention; and (b) a pharmaceutically acceptable carrier. The term "pharmaceutically effective amount" refers to an amount enough to show and accomplish efficacies and activities of the recombinant protein of this invention as described above.

According to the present invention, the pharmaceutical composition may contain pharmaceutically acceptable carriers. The pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition of this invention may be administered mucosally, orally, or parenterally, according to an embodiment, mucosally injection.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition, and physicians of ordinary skill in the art can determine an effective amount of the pharmaceutical composition for desired treatment. Generally, suitable dosage unit for human host is to administer with the pharmaceutical composition in 0.001-100 mg/kg (body weight).

According to the conventional techniques known to those skilled in the art, the pharmaceutical composition may be formulated with pharmaceutically acceptable carrier and/or vehicle as described above, finally providing several forms including a unit dose form and a multi-dose form. Formulation may be oil or aqueous media, resuspension or emulsion, extract, powder, granule, tablet and capsule and further comprise dispersant or stabilizer.

The composition of the present invention may be provided as a food composition.

According to an embodiment of the present invention, the composition of the present invention is a food composition comprising (a) a sitologically effective amount of the recombinant protein any one of the recombinant proteins of the present invention; and (b) a sitologically acceptable carrier. When the composition of the present disclosure is prepared as a food composition, the food composition of the present disclosure may comprise, in addition to the recombinant protein of the present disclosure as active ingredients, ingredients commonly added for preparation of food. For example, proteins, carbohydrates, fats, nutrients, seasoning or flavors may be added. The carbohydrate may be, for example, a sugar such as a monosaccharide, e.g. glucose, fructose, etc., a disaccharide, e.g. maltose, sucrose, oligosaccharide, etc. or a polysaccharide, e.g. dextrin, cyclodextrin, etc. or a sugar alcohol such as xylitol, sorbitol, erythritol, etc. The flavor may be a natural flavor [thaumatin, stevia extract (e.g. rebaudioside A, glycyrrhizin, etc.]) or a synthetic flavor (saccharin, aspartame, etc.). For example, when the food composition of the present disclosure is prepared as a drink, it may further comprise, in addition to the recombinant protein of the present disclosure as the active ingredient, citric acid, high-fructose corn syrup, sugar, glucose, acetic acid, malic acid, fruit juice, eucommia extract, jujube extract, licorice extract, or the like.

The composition of the present invention may be provided as a cosmetic composition.

In cases where the composition of the present invention is used to prepare a cosmetic composition, the composition of the present invention contains not only the foregoing recombinant protein but also ingredients normally used in the cosmetic composition, for example, a carrier and normally additives, such as an antioxidant, a stabilizer, a solubilizer, vitamins, a pigment, and a flavor.

As the carrier, purified water, monohydric alcohol (ethanol or isopropyl alcohol), polyhydric alcohol (glycerol, 1,3-butylene glycol or propylene glycol), higher fatty acid (palmitic acid or linolenic acid), oil (wheat germ oil, camellia oil, jojoba oil, olive oil, squalene, sunflower oil, macadamia peanut oil, avocado oil, soybean water-added lecithin or fatty acid glyceride) or the like may be used, but the carrier is not limited thereto. In addition, a surfactant, a sterilizer, an antioxidant, a UV absorber, an anti-inflammatory agent, and a refreshing agent may be added as needed.

The surfactant may include one selected from the group consisting of polyoxyethylene, hardened castor oil, polyoxyethylene, oleyl ether, polyoxyethylene monooleate, glyceryl monostearate, sorbitan monostearate, polyoxyethylene monostearate, sorbitan, sucrose fatty acid ester, hexaglycerine monolaurate, polyoxyethylene reduced lanolin, POE, glyceryl pyroglutamate, isostearic acid, diester, N-acetylglutamine, and isostearyl ester.

The sterilizer may include one selected from the group consisting of hinoki thiol, triclosan, chlorhexidine gluconate, phenoxy ethanol, resorcin, isopropyl methyl phenol, azulene, salicylic acid, and zinc pyrithione.

As the antioxidant, any one of butyl hydroxyanisole, gallic acid, propyl gallate, and erythorbic acid may be used.

As the UV absorbent, any one of benzophenones such as dihydroxy benzophenone, melanin, para-amino benzoic acid ethyl, para-dimethylamino benzoic acid 2-ethylhexyl ester, cynocite, para-methoxy cinnamic acid 2-ethylhexylester, 2-(2-hydroxy-5-methylphenyl)benzotriazole, urocanic acid, and metal oxide microparticles may be used.

For the anti-inflammatory agent, glycyrrhetinic acid dipotassium or allantoin may be used, and as the refreshing agent, capsicum tincture or 1-menthol may be used.

The dosage form of the composition is any dosage form that can blend the recombinant protein as an active ingredient, and examples of the dosage form of cosmetics for preventing hair loss may include various forms of a sol, a gel, an emulsion, oil, wax, aerosol, and the like, such as hair tonic, hair cream, hair lotion, hair shampoo, hair rinse, hair conditioner, hair spray, hair aerosol, pomade, a powder, and a gel, but are not limited thereto.

In still another aspect of this invention, there is provided a method for inhibiting, improving, or preventing aging, comprising administering to a subject in need thereof a composition comprising a recombinant protein of flagellin, which is the constituent of *Vibrio vulnificus* flagella, fused with a pathogenic protein antigen, which is pneumococcal surface protein A (PsaA) of *Streptococcus pneumonia*.

We have generated a new adjuvant-antigen fusion combo vaccine FP, composed of flagellin (FlaB, F) of *Vibrio vulnificus* and pneumococcal surface protein A (PspA, P) aiming at elderly community. The immunization with FP resulted in a significant antigen-specific antibodies production and successful aging protective efficacy against infection of *S. pneumoniae* in both young and aged mice.

Toll-like receptor 5 (TLR5) plays an important role in prolonging the lifespan or healthspan mediated by recombinant proteins comprising flagellin and pneumococcal surface proteins. According to an embodiment of the present invention, the administration of the composition of the present invention not only has a direct effect of prolonging the life span, but also prevents hair loss, prolapse of the rectum and cataracts; increases bone density and maintains spinal curve angle; increases bone marrow-derived stem cell activity; recovers athletic ability and cognitive function; enhances GALT (gut-associated lymphoid tissue)-mediated immunity and metabolic activity (e.g., gluconeogenesis in liver), thus improves various symptoms associated with aging. These results show that the recombinant proteins of the present invention exhibit lifespan extension or healthspan prolongation effects by inhibiting the aging-related phenomenon through the TLR5-dependent molecular pathway.

According to an embodiment of the present invention, the aging is immunosenescence. Immunosenescence is one of the hallmarks of aging. Immunosenescence is multifaceted with an enhanced susceptibility to infection and chronic tissue inflammation, resulting in induction of aging dependent degenerative diseases such as metabolic diseases, cardiovascular disease, neurodegenerative syndromes and frailty, etc. Since the immune system is responsible also for tissue homeostasis and repair, this could be a target of intervention for healthy aging.

According to an embodiment of the present invention, the recombinant protein of the present invention is FlaB-PspA protein comprising an amino acid sequence of SEQ ID NO: 1.

As used herein, the term "administration" or "administer" refers to provide the subject with the desired material in any suitable manner. The administration route of the composition for inhibiting, improving or preventing of aging may be orally or parenterally administered through any route as long as it can reach the target tissue. The composition of the present invention may also be administered using any device capable of delivering the active ingredient to the target cell or tissue.

The composition of the present invention may be administered orally or parenterally. In case parenteral administration, the composition may be injected through intravenous, subcutaneous, intramuscular, intraperitoneal, transdermal, intranasal, mucosal administration.

According to an embodiment of the present invention, the composition of the present invention may be administered intranasally. In this case, the active ingredient can be absorbed through the intranasal mucosa.

The administration can be continuously performed at regular intervals, for example, the composition of the present invention can be continuously administered at intervals of 1 to 30 days.

According to an embodiment of the present invention, the composition of the present invention can be continuously administered at intervals of 1 to 20 days. According to another embodiment of the present invention, the composition of the present invention can be continuously administered at intervals of 3 to 20 days, 5 to 20 days, or 7 to 20 days. According to other embodiment of the present invention, the composition of the present invention can be continuously administered at intervals of 7 to 14 days. According to certain embodiment of the present invention, the composition of the present invention can be continuously administered at intervals of 7 days (1 week) or 14 days (2 weeks).

The administration may be performed a predetermined number of times or more at regular intervals.

According to one embodiment of the present invention, the composition of the present invention may be administered three or more times continuously at regular intervals. According to another embodiment of the present invention, the composition of the present invention may be administered more than 4 times, more than 5 times, more than 6 times, more than 7 times, more than 8 times, more than 9 times, more than 10 times, more than 11 times, more than 12 times, more than 13 times, more than 14 times, more than 15 times, more than 16 times, more than 17 times, more than 18 times, more than 19 times, or more than 20 times continuously at regular intervals. According to certain embodiments of the invention, the composition of the invention may be administered 8 or more times to immunize.

A suitable dosage amount of the recombinant protein of the present invention may vary depending on formulation methods, administration methods, the subject's age, body weight, sex, pathogenic state, diet, administration time, administration route, an excretion rate and sensitivity for a used composition, and physicians of ordinary skill in the art can determine an effective amount of the recombinant protein for desired treatment. Generally, suitable dosage unit for human host is to administer with the recombinant protein in 0.001-1000 μg/kg (body weight) per dosing interval.

According to one embodiment of the present invention, the recombinant protein, which is an active ingredient of the composition of the present invention, can be administered at a dose of 0.001-1000 μg/kg (body weight) per administration.

According to one embodiment of the present invention, the recombinant protein can be administered at a dose of 0.01-1000 μg/kg (body weight) per administration.

According to another embodiment of the present invention, the recombinant protein can be administered at a dose of 0.1-1000 μg/kg (body weight) per administration.

According to other embodiment of the present invention, the recombinant protein can be administered at a dose of 1-1000 μg/kg (body weight) per administration.

According to still other embodiment of the present invention, the recombinant protein can be administered at a dose of 10-1000 μg/kg (body weight), 100-1000 μg/kg (body weight), 200-1000 μg/kg (body weight), 300-1000 μg/kg (body weight), 400-1000 μg/kg (body weight), 500-1000 μg/kg (body weight), 600-1000 μg/kg (body weight), 700-1000 pig/kg (body weight), 800-1000 μg/kg (body weight), or 900-1000 μg/kg (body weight) per administration.

According to still other embodiment of the present invention, the recombinant protein can be administered at a dose of 10-900 μg/kg (body weight), 10-800 μg/kg (body weight), 10-700 μg/kg (body weight), 10-600 μg/kg (body weight), 10-500 μg/kg (body weight), 10-400 μg/kg (body weight), 10-1000 μg/kg (body weight), 10-200 μg/kg (body weight), or 10-100 μg/kg (body weight) per administration.

According to still other embodiment of the present invention, the recombinant protein can be administered at a dose of 100-900 μg/kg (body weight), 100-800 μg/kg (body weight), 100-700 μg/kg (body weight), 100-600 μg/kg (body weight), 100-500 μg/kg (body weight), 100-400 μg/kg (body weight), 100-300 μg/kg (body weight), or 100-200 μg/kg (body weight) per administration.

According to still other embodiment of the present invention, the recombinant protein can be administered at a dose of 125 μg/kg (body weight), 200 μg/kg (body weight), or 325 μg/kg (body weight) per administration.

On the other hand, the composition of the present invention to be administered for inhibiting, improving, or preventing aging may be a pharmaceutical composition or a food composition.

Since the method for inhibiting, improving, or preventing aging of the present invention uses the above-described composition for preventing, improving, or treating aging, descriptions of overlapping contents therebetween are omitted to avoid excessive complication of the specification due to repeated descriptions thereof.

In still another aspect of this invention, there is provided a method for increasing the lifespan of a mammal, comprising administering to a subject in need thereof a composition comprising a recombinant protein of flagellin, which is the constituent of *Vibrio vulnificus* flagella, fused with a pathogenic protein antigen, which is pneumococcal surface protein A (PsaA) of *Streptococcus pneumonia*.

In still another aspect of this invention, there is provided a method for increasing the healthspan of a mammal, comprising administering to a subject in need thereof a composition comprising a recombinant protein of flagellin, which is the constituent of *Vibrio vulnificus* flagella, fused with a pathogenic protein antigen, which is pneumococcal surface protein A (PsaA) of *Streptococcus pneumonia*.

As used herein, the term "subject" includes, but is not limited to, human, monkey, cow, horse, sheep, pig, chicken, turkey, quail, cat, dog, mouse, rat, rabbit or guinea pig. Specifically, the subject of the present invention is a mammal. More specifically, the subject of the present invention is human.

An effective amount of the recombinant increases the lifespan of mammals. In one embodiment, an effective amount of the recombinant increases the lifespan of mammals by a statistically significant amount compared to the lifespan of an untreated mammal. In another embodiment, an effective amount of the recombinant increases the lifespan of mammals by at least 5%. In other embodiment, an effective amount of the recombinant increases the lifespan of mammals by at least 10%, 15%, 20%, 25%, 30%, 35%, 40%, 45%, 50%, 55%, 60%, 65%, 70%, 75%, 80%, 85%, 90%, 95%, or 100% over control. In still other embodiment, an effective amount of the recombinant increases the lifespan of mammals by at 5-20%.

Since the method for increasing the lifespan of healthspan of the present invention uses the above-described composition for preventing, improving, or treating aging, descriptions of overlapping contents therebetween are omitted to avoid excessive complication of the specification due to repeated descriptions thereof.

Advantageous Effects

The features and advantages of this invention will be summarized as follows:

(a) The present invention provides a composition for preventings, improving, or treating aging, the composition comprising, as an active ingredient, a recombinant protein of flagellin, which is the constituent of *Vibrio vulnificus* flagella, fused with a pathogenic protein antigen.

(b) The present invention provides a composition for preventing, improving, or treating metabolic disease, hair-related disease, eye disease, bowel disease, or bone disease, the composition comprising the recombinant protein as an active ingredient.

(c) The present invention can improve external and internal aging-related malfunctions and enhance immunity by using the recombinant protein of the present invention.

(d) The present invention can easily perform immunization through mucosal administration of the composition of the present invention.

BRIEF DESCRIPTION OF THE DRAWINGS

FIG. 1 shows a schematic view with respect to an experiment schedule and an experiment scheme for immunizing aged mice.

FIGS. 2A and 2B show graphs illustrating measurement results of changes in food intake (2B) and body weight (2A) in aged mice according to the immunization with FlaB-PspA recombinant protein.

FIG. 3 shows morphological change results of aged mice through continuous immunization of an antigen.

FIG. 4 is an IgA reaction graph in aged mice by continuous immunization.

FIG. 5 illustrates histopathological findings with respect to the cutaneous histological change of aged mice by immunization with FlaB-PspA recombinant protein.

FIG. 6 shows the changes of hematopoietic stem cells in marrow cells of aged mice by immunization with FlaB-PspA recombinant protein.

FIG. 7 shows organs illustrating lymphatic system changes of aged mice by immunization with FlaB-PspA recombinant protein.

FIG. 8 shows the change in bone mineral density of aged mice by immunization with FlaB-PspA recombinant protein.

FIG. 9 shows mucosal immunization and measurement of life span and healthspan. The mice were initially immunized at 650 days and continually immunized with phosphate-buffered saline (PBS, 16 μl), as a control, PBS containing FP (6.5 μg), FP SDM (6.5 μg), PspA (2.5 μg), or FlaB (4 μg) every 2 weeks via the intranasal route and evaluated various health parameters after 4 months (8th nasal vaccination). The lifespan was continuously observed until the mice die. FP, FlaB-PspA; SDM, site-directed mutation.

FIGS. 10A-10K show FPNI increase longevity with enhancement of healthspan.

Kaplan-Meier Survival graphs of female (n=26/each group)(10A) and male (n=27/each group)(10B) mice, comparing control mice to those nasally administered with FP recombinant protein (6.5 μg) starting at 650 days of age.

After eight times with FP or vehicle during 4 months, mice were analyzed and displayed by quantitative bar graphs with their symptoms of hair loss (n=36/O-Ctrl; n=43/O-FP) (10*c*), bone mineral density of spine and femur by micro-CT (n=13/Y; n=13/O-Ctrl; n=14/O-FP) (10*d*), total area of tube formation of bone marrow-drived stem cells (n=10) (10*e*), percent of LT-HSC in BM (n=8/Y; n=7/O-Ctrl; n=8/O-FP) (10*f*) and number of thymocytes (n=10/Y; n=7/O-Ctrl; n=12/O-FP) (10*g*). Cognitive functions were displayed the open field test (n=16/Y; n=8/O-Ctrl; n=16/O-FP) (10*h*), the nest score (n=9/Y; n=9/O-Ctrl; n=8/O-FP) (10*i*), the preference score (n=10/Y; n=7/O-Ctrl; n=8/O-FP) (10*j*), and the passive avoidance test (n=7/Y; n=6/O-Ctrl; n=6/O-FP (10*k*).

The data are expressed as mean±SEM. Differences between each group were analyzed by Log-rank test (10*a* and 10*b*), two tailed Student t-test (10*c*), Mann-Whiteny U-test (10*d*-10*k*). *P<0.05, P<0.01, *P<0.001. FP, stands for the FlaB-PspA fusion protein; Ctrl, vehicle control aged mice. LT-HSC, long term-hematopoietic stem cell; BM, bone marrow.

FIGS. 11A-11C show beneficial health effect by FPNI in aged mice. The mice (21 months) were immunized with FP or vehicle for eight times, and observed of phenotype and bone radiographs. Representative image of cataract (11A) and rectal prolapse (11B) was displayed and the symptoms were scored and quantitated by graphs (21 months: n=46/each group, 25 months: n=36/O-Ctrl; n=43/O-FP). Representative lateral radiograms demonstrated the kyphosis (11*c*, upper). The angle of spinal curvature was represented by a quantitative bar graph (11C, below). The data are expressed as mean±SEM. Differences between each compared group were analyzed by two-tailed Student t-test (11A and 11B) and Mann-Whitney U-test (11*c*). P<0.01, *P<0.001. Score range: 1 (Good) to 4 (Severe). Ctrl, vehicle control aged mice; C7, seventh cervical vertebra; L5, fifth lumbar vertebra.

FIGS. 12A-12D show the effect of FPNI in spleen from aged mice. After eight times of FP or vehicle immunization, (12A) Representative hematoxylin and eosin (H&E)-stained spleen (n=3/each group). (12B) The number of T-cell (n=5/Y; n=3/O-Ctrl; n=5/O-FP) and (12C) weight (n=30/Y; n=32/O-Ctrl; n=34/O-FP) in spleen. (12D) Western blot analysis showing p16INK4a and p53 protein levels from spleen tissues of young mice and FP- or vehicle-immunized aged mice (n=5/Y; n=6/O-Ctrl; n=7/O-FP) (upper) and represented by quantitative bar graphs with protein expression (below). The data are expressed as mean±SEM. Differences between each group were analyzed by Mann-Whiteny U-test (B and D) and two tailed Student t-test (C). *P<0.05, ***P<0.001.

FIGS. 13A-13J show the effect of FPNI on immune cell distribution in splenocytes. After eight times of FP or vehicle immunization, immune cell (13A-13D) and T-cell population or signaling (13E-13J) was analyzed by flow cytometry. Percentage of macrophages (13A), dendritic cells (13B), monocytes (13C) and B cells (13D) in splenocytes. Phenotypic analysis of naïve T-cells (13E), CD4+ T cells (13F), and CD8+ T cells (13*g*) in slenocytes and intracellular cytokine expression of IL2 (13H), TNF-α (13I), and IL10 (13J) in CD4+ T-cells. The data are expressed as mean±SEM (n=10/Y; n=7/O-Ctrl; n=10/O-FP). Differences between each group were analyzed by Mann-Whiteny U-test.

Figure 14C:
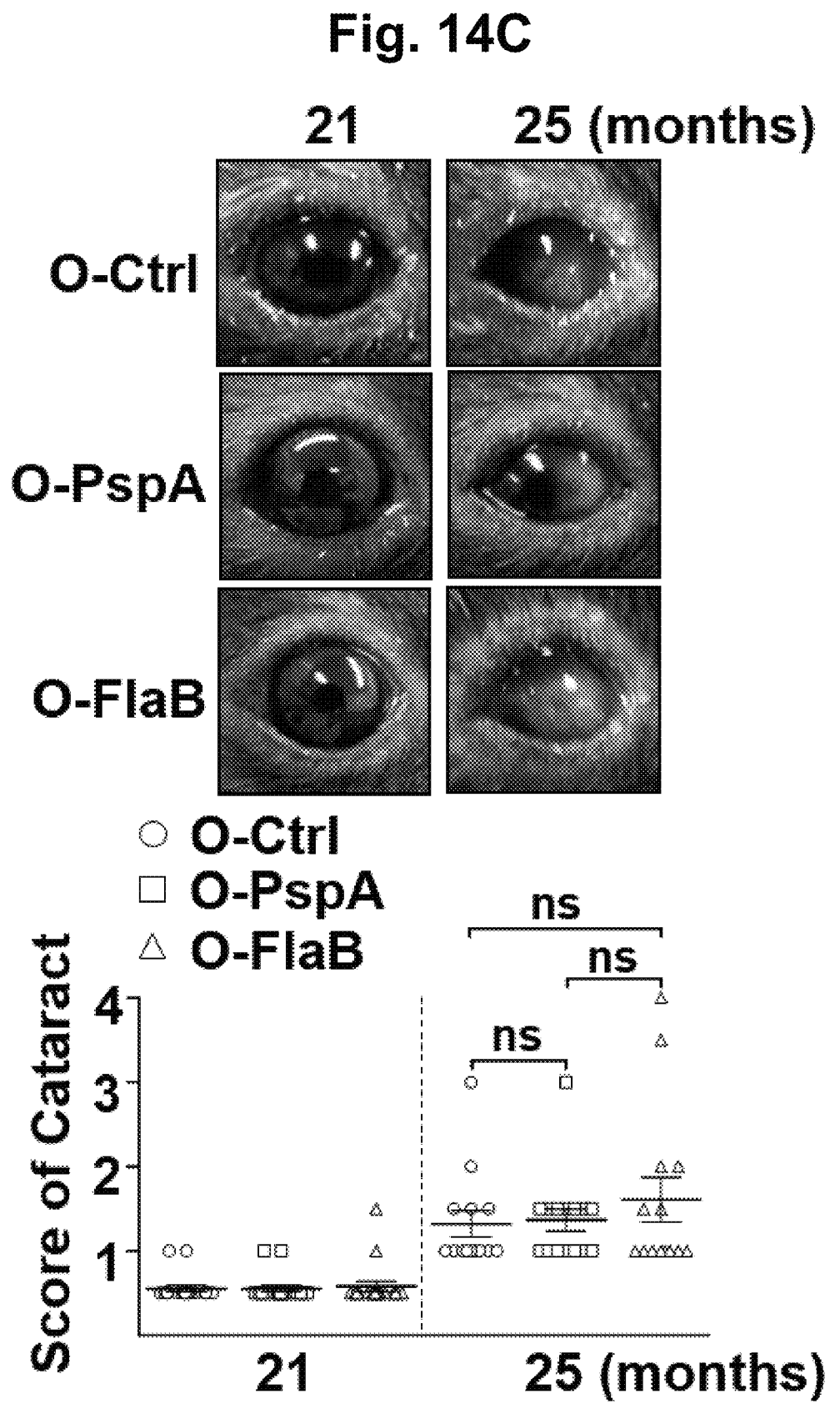

FIGS. 14A-14D show the aging phenotypes and glucose uptake by mucosal immune stimulation with the PspA and FlaB in mice. After eight times with PspA (2.5 μg), FlaB (4 μg) or vehicle during 4 months, mice were analyzed and displayed by quantitative bar graphs with their symptoms of hair loss (14A), rectal prolapse (14B), and cataract (14C) (n=14-19/O-Ctrl; n=15-19/O-PspA; n=14-19/O-FlaB). [$^{18}$F] FDG microPET images in mice brain (14D, left) and represented quantitative analysis of glucose uptake (14D, right) (n=4/each group). The data are expressed as mean±SEM. Differences between each group were analyzed by Mann-Whiteny U-test. *P<0.05.

Figure 15B:
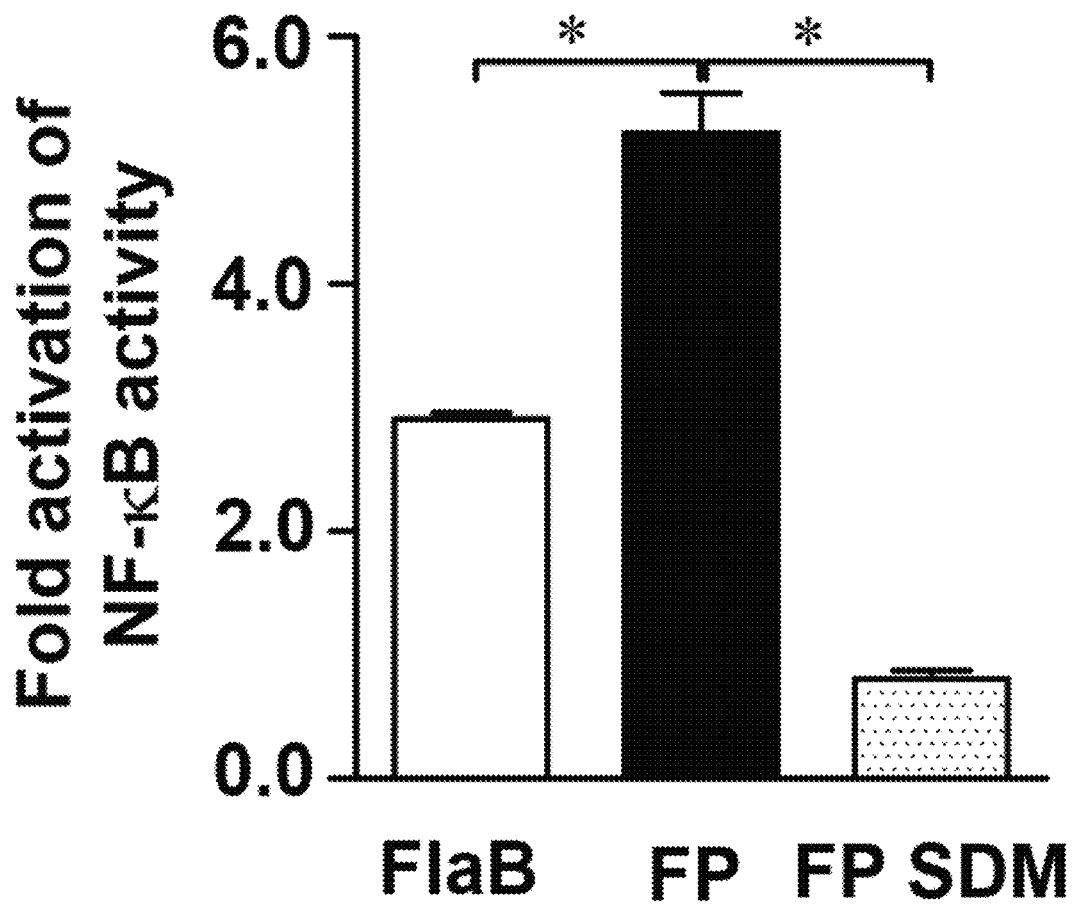
Figure 15C:
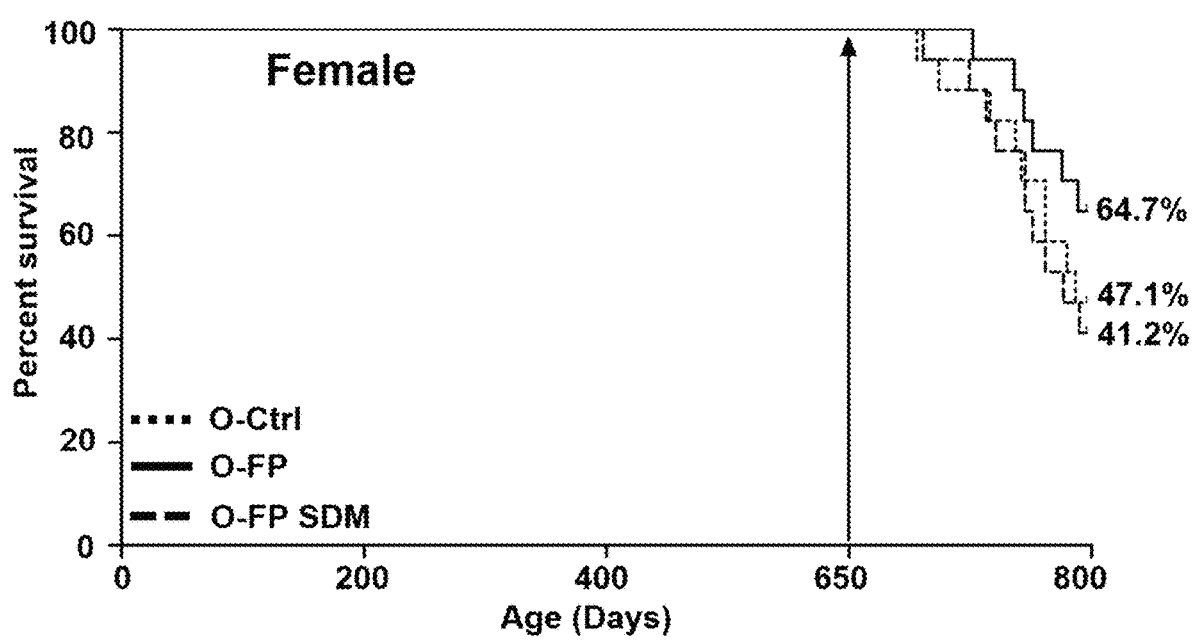

FIGS. 15A-15C show FPNI led to longevity via TLR5-dependent signaling. The FP or site-directed mutant FP (FP SDM), which cannot bind with TLR5, was generated and immunized at 650-day-aged female (21 months) and monitored their median survival. (15A) Amino acid sequences of TLR5 binding site (upper; SEQ ID NO: 4) and its mutant derivative (below; SEQ ID NO: 11). Location of site-directed mutations in the predicted TLR5 binding region (box) (SEQ ID NOs: 9 and 10). (15B) Activation of NF-κB signaling through TLR5 stimulation with FP SDM proteins. (15C) Survival rates of female mice (n=17/each group) received mucosal immunization with FP or FP SDM were compared with those of vehicle control mice. The survival rates were compared with the Kaplan-Meier analysis. The data are expressed as mean±SEM. Differences between each compared group were analyzed by the Mann-Whitney U-test. *P<0.05.

FIGS. 16A-16G show FPNI induced activation of intestinal mucosal immunity and metabolic enhancement. After eight times of FP or vehicle immunization, (16A) Western blot analysis showing TLR5, p16INK4a, p53 protein levels from small intestine tissues of young mice and FP- or vehicle-immunized aged mice (n=5/each group) (upper) and represented by quantitative bar graphs with protein expression (down), (16B) Representative hematoxylin and eosin (H&E)-stained ileum (n=3/each group). Insert box was indicated higher magnification. (16C) PspA-specific secretory IgA production in feces (n=5/each group). (16D) Serum leptin levels of young mice and FP- or vehicle-immunized aged mice (n=14/each group). (16E) [18F]FDG microPET images in mice brain (left) and represented quantitative analysis of glucose uptake (right) (n=12/Y; n=12/O-Ctrl; n=13/O-FP). The food intake (16F) and body weight (16G) were measured once a week after each immunization in aged mice (n=45-59/O-Ctrl; n=54-60/O-FP). The data are expressed as mean±SEM. Differences between each group were analyzed by Mann-Whiteny U-test (16a and 16c-16e) and two tailed Student t-test (16f and 16g). *P<0.05, P<0.01, *P<0.001. SUV, standardized uptake value; ns, not significant.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

Examples 1-7

Materials and Methods

Aged mice (C57BL/6J, aged at least 23 months) were intranasally immunized with purified protein and recombinant protein continuously at two-week intervals. PspA protein and FlaB-PspA protein were purchased from the laboratory of professor Jun-haeng, Lee of the Clinical Vaccine Development Project Group of Chonnam National University.

All immunization experiments were conducted in the specific pathogen free (SPF) facility. Young mice (8-10 week old) were used for a control group. A non-immunized aged mouse group, an aged mouse group intranasally immunized with PBS (16 µl/mouse) 8 times or more at 2-week intervals, an aged group intranasally immunized with only PspA (2.5 µg/16 µl/mouse) protein 8 times or more at 2-week intervals, and an aged group intranasally immunized with FlaB-PspA (6.5 µg/16 µl/mouse) recombinant protein 8 times or more at 2-week intervals were used for immunization experimental groups.

The morphological and behavioral changes of the aged mice were observed during the continuous immunization.

Following the immunization, the body weight and feed intake of each mouse were measured every week. In order to accurately measure the changes according to the immunization, the mice were separately managed one by one. In addition, 50 g of feed was provided for each mouse, and then the remainder of the feed was accurately measured at one-week intervals. Also, the body weight of each mouse was accurately measured using an animal scale every week.

In order to compare morphological changes of aged mice according to the immunization, the appearances of the mice, that is, the hair condition, hair loss, and decoloration was observed and the anus or eyes were also continuously observed, thereby collecting changed patterns.

In order to compare the behavior changes of the aged mice according to the immunization, the behavioral changes of the mice were observed at a certain point during the immunization. In order to verify the behavioral ability of the mice, the aged mice of each group were placed in a confined space, and the motions of the mice were observed for a period of time. The motions were compared based on general standard items of mouse behavioral ability, that is, the motion, the number of times of standing on hind legs, the number of times of supporting using forelegs, and the number of times of touching the nose.

During the continuous immunization, in order to verify the change of the immune response depending on the number of times of immunization, blood and feces were collected from some mice, and then the change in antibody production was measured using enzyme-linked immunosorbent assay (ELISA).

After immunization for an appropriate period of time, several samples were collected from the overall mice, and then the entire changes of the aged mice according to the immunization were measured through various experiments.

In order to verify the change of the immune response according to the continuous immunization, serum and several mucous samples (feces, saliva, vaginal washing, etc.) were collected from the mice, and in order to compare the mucosal immune response, the change in secretory immunoglobulin A (secretory IgA, sIgA) production was measured by ELISA.

In order to compare the morphological changes of the aged mice according to the immunization, various tissues including the skin tissue were collected, and fixed with formalin prior to making a paraffin-block, and pathological findings were compared through Hematoxylin and Eosin (H&E) staining. In addition, with reference to the effect of immunization and the feed intake through the mucosal immune response, pathological findings of the tissues of small and large intestines, which largely account for the mucosal immunity, were compared and observed through H&E staining.

In order to compare the antigen-mediated cellular immune response with respect to lymphocytes separated from immune-related tissues, the lymphocytes were separated from the cervical lymph nodes and spleen and then the antigen-mediated cellular response was compared by ELISA. In addition, in order to compare and observe changed patterns of various bone marrow cells with respect to the cells separated from the bone marrow, the bone marrow cells were separated from hind legs of the aged mice, and the comparison was conducted using flow cytometry (FACS, Beckman Coulter). Particularly, the frequency of hematopoietic stem cells essentially associated with T cell differentiation was compared and observed through immuno-staining using CD34, which is a hematopoietic stem cell indicator.

In order to compare the change in bone mineral density (BMD) of the aged mice according to the immunization with respect to spines separated from the mice, the spines were extracted from the mice, and then the bone mineral density (BMD) according to the continuous immunization and kyphosis according to aging of the aged mice were compared and observed using micro-computer tomography (microCT: Skyscan 1172, Micro Photonics Inc., US).

Next, for the ongoing study, the morphological and behavioral changes of the aged mice according to the continuous immunization were compared and compared in connection with metabolism. For this, after the blood was collected from the aged mice, the serum or plasma was separated therefrom, and then the changes in hormone-related and metabolism-related genes were compared. In addition, in order to compare and observe the change in mucosal immunity according to the immunization, the intestine-associated microenvironment was compared using normal microbiota. In addition, the blood and feces were collected from the aged mice continuously immunized with antigens, and then the gene expression pattern was compared and observed through advanced analysis methods, such as microarray.

Results

Example 1: Changes in Feed Intake and Body Weight in Aged Mice Immunized with Flagellin-PspA Recombinant Protein While the aged mice were intranasally immunized eight times at two-week intervals, the body weight and the feed intake of the mice of each group were measured. The non-immunized aged mice were used as a control group.

The aged mice were intranasally immunized eight times with phosphate buffered saline (PBS), prepared 2.5 μg of PspA, and 6.5 μg of FlaB-PspA recombinant protein at two-week intervals. The body weight and the feed intake of the mice of each group were measured every week. The measurement results are shown in FIGS. 2a and 2b.

Figure 2A:
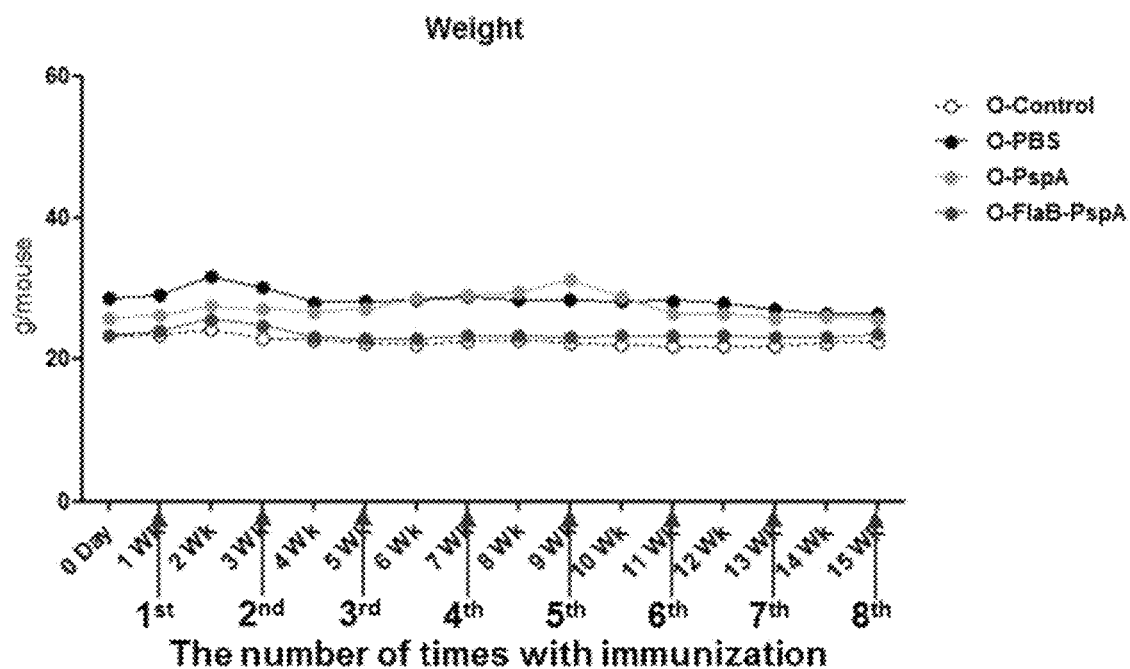
Figure 2B:
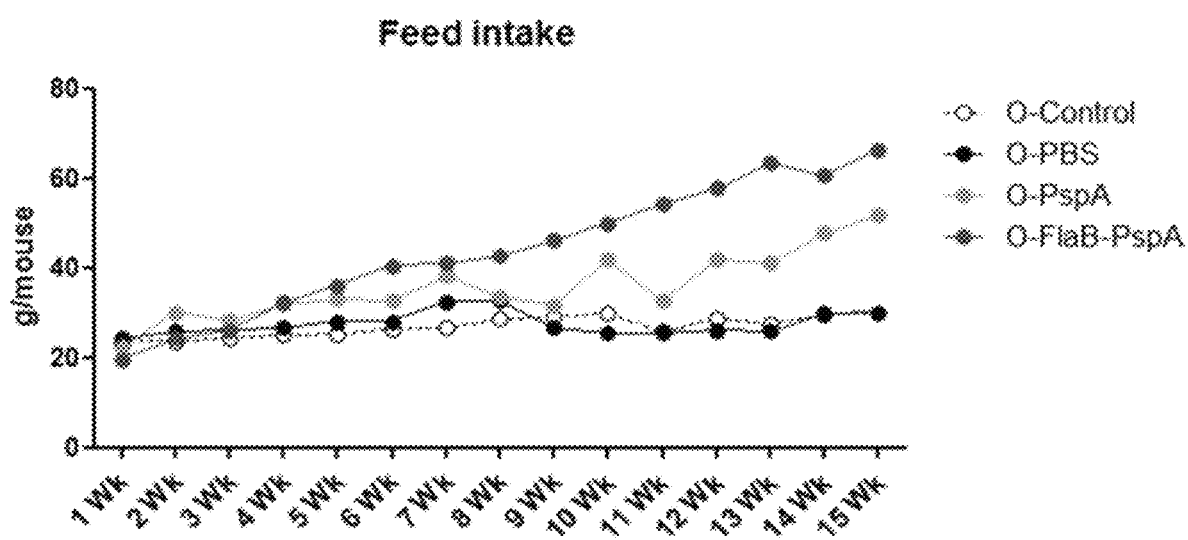

As a result of body weight measurement, it was verified that the non-immunized mouse group, the group immunized with PBS, the group immunized with PspA alone, and the group immunized with FlaB-PspA recombinant protein showed no change in body weight due to the immunization (FIG. 2a).

As a result of comparing the feed intake of the aged mice according to the immunization, the non-immunized mouse group showed no great change in the feed intake over time, and the group immunized with PBS also showed no great change in the feed intake, regardless of eight times of immunization at two-week intervals. On the other hand, the group immunized with PspA alone was verified to show a gradual increase in the feed intake during the continuous immunization. Particularly, it was shown that the group immunized with FlaB-PspA recombinant protein showed an increase in the feed intake through the continuous immunization, and here, the rate in increase of the feed intake was significantly higher than that of the group immunized with PspA alone (FIG. 2b).

As can be seen from the results of example 1, it can be confirmed that, when the aged mice are continuously immunized with antigens, the body change is not greatly changed, but the feed intake is greatly increased. Particularly, it can be seen that the immunization with a recombinant protein including a vaccine adjuvant fused with a pathogenic antigen significantly increases the feed intake.

Figure 3:
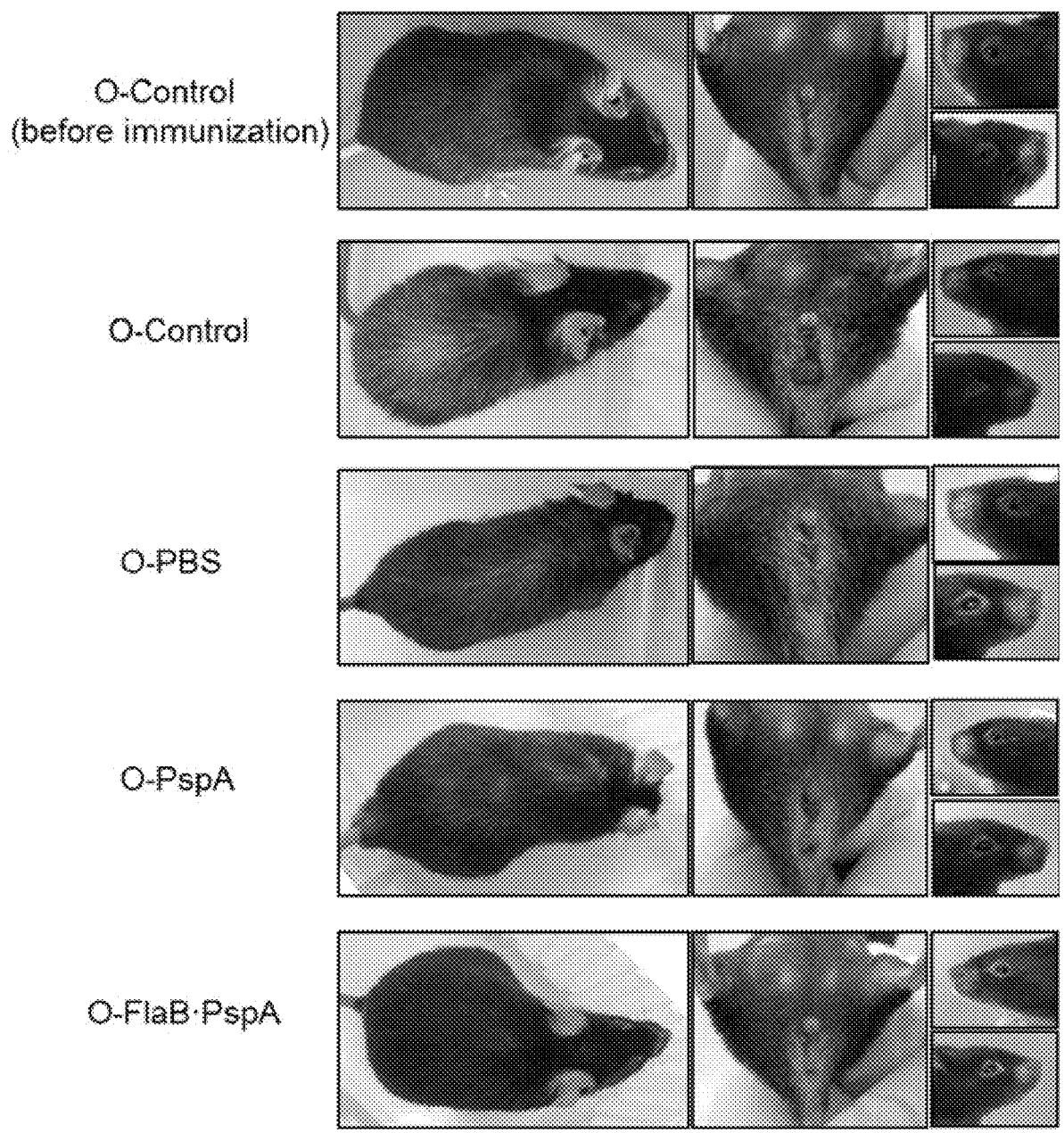

Example 2: Observation of Morphological Changes of Mice Through Continuous Immunization with Antigen While the aged mice were intranasally immunized eight times at two-week intervals, the morphological changes of the mice according to the immunization were monitored every week. The results are shown in FIG. 3. The non-immunized aged mice were used as a control group.

The aged mice prior to the immunization had no abnormal findings by appearances. There were no abnormal findings in view of hair condition, hair luster, hair decoloration, hair loss, the anus (colitis or hernia), or the eyes (cataracts).

However, as a result of observing the aged mice following the immunization, it was verified that the non-immunized aged mouse group had a worse hair condition than the group immunized eight times at two-week intervals, and the appearances became generally worse, such as a severe progression of hair decoloration or hair loss. Besides, normal findings, such as hernia, were severely shown in the anus, and abnormal findings, such as suspected cataracts, were severely shown also in both eyes (O-control). The group immunized with PBS also had a bad hair condition, and the appearances thereof became severely worse, such as severe progressions of hair decoloration and hair loss. In addition, findings of slight colitis or hernia were shown in the anus, and findings of suspected cataracts were severely shown in one eye (O-PBS).

On the other hand, as a result of eight times of immunization with PspA, slight decoloration was shown but the hair loss was not severe in the appearance of the aged mice, and abnormal findings were not observed in the anus or eyes (O-PspA). Particularly, it was verified that, the group immunized with FlaB-PspA recombinant protein had a good hair condition so that the hair condition of the aged mice of the group was very similar to that of the aged mice prior to the immunization, and abnormal findings were observed in neither the anus nor eyes (O-FlaB-PspA).

As can be seen from the results of example 2, it can be verified that the appearances of the aged mice are better through the continuous immunization. It is general that the aging causes a severe progression of hair decoloration or hair loss and abnormal findings, such as cataracts occurring in eyes. Rodents showed abnormal findings, such as hernia, in the anus due to the reduction in the muscle amount. However, the continuous immunization with antigens could be verified to prevent the occurrence of such abnormal findings. Particularly, it can be seen that, as for the group immunized with a recombinant protein including a vaccine adjuvant fused with a pathogenic antigen, the appearances of the aged mice are maintained over time or have a better condition.

Figure 4:
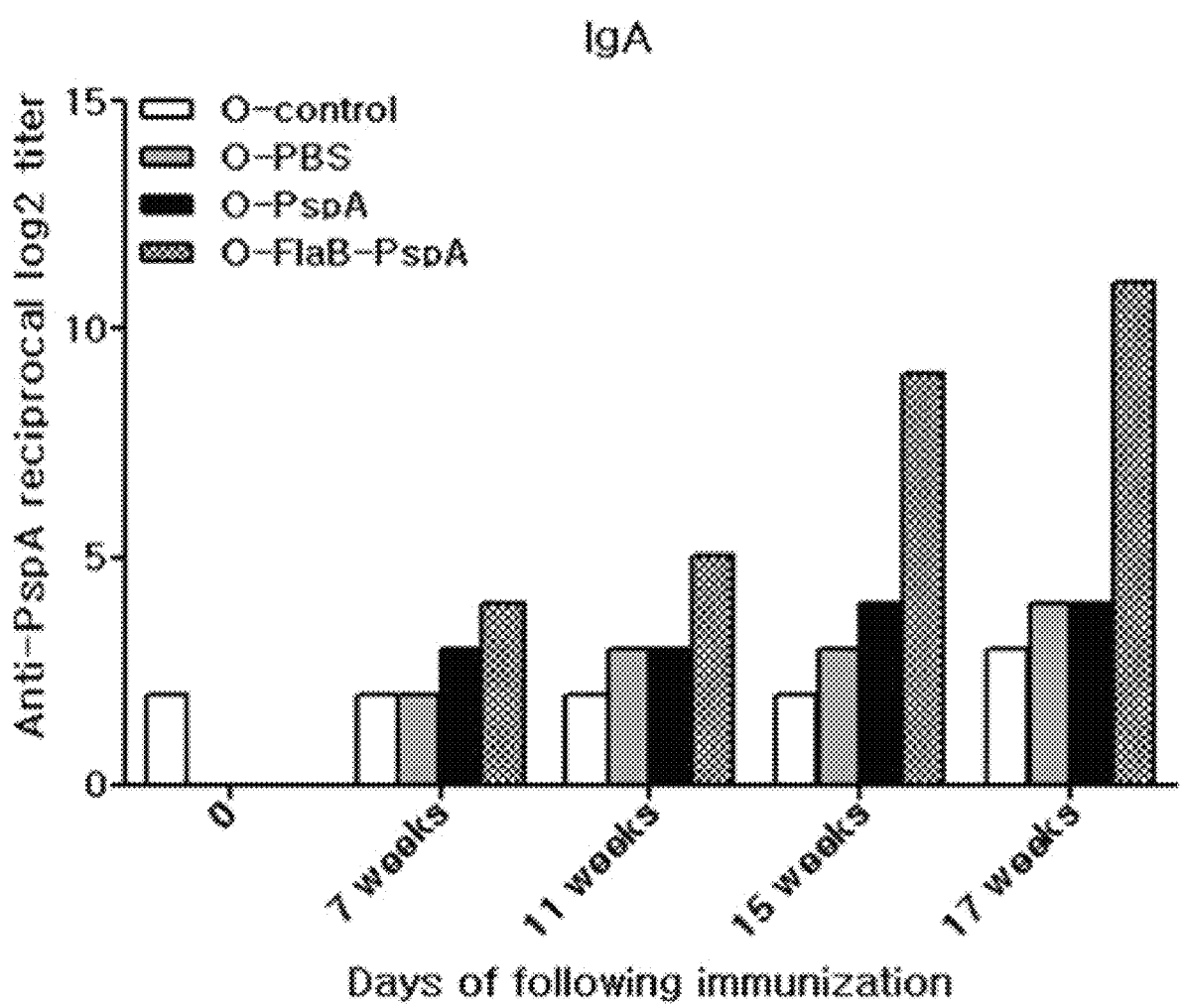

Example 3: Change in IgA Reaction of Aged Mice Through Continuous Immunization with Antigen During the continuous immunization, the feces were collected from the mice of each group after each immunization to verify the IgA reaction of the aged mice according to the immunization by ELISA. The results are shown in FIG. 4. The non-immunized aged mice were used as a control group.

The non-immunized aged mice had no great difference in the IgA response during the immunization (O-control). It was verified that the group immunized with PBS alone showed no great difference in the IgA response, and then showed a slight increase in the IgA response after the sixth immunization, but there is no great increase in the IgA response (O-PBS). The group treated with PspA alone showed the IgA response after the fourth immunization, but showed no great difference after that (O-PspA). Whereas, as for the group immunized with FlaB-PspA recombinant protein, the IgA response was significantly increased depending on the number of times of immunization (O-FlaB-PspA).

As can be seen from the results of example 3, it was verified that, as a result of verifying the IgA reaction with respect to the mucosal immune reaction of the aged mice through the continuous immunization, the IgA reaction was significantly increased depending on the immunization in the group immunized with FlaB-PspA recombinant protein while no great change in the IgA reaction or a slight IgA reaction was shown in the other groups. Judging from the results, the mucosal immunity of the aged mice is activated by the recombinant protein.

Figure 5:
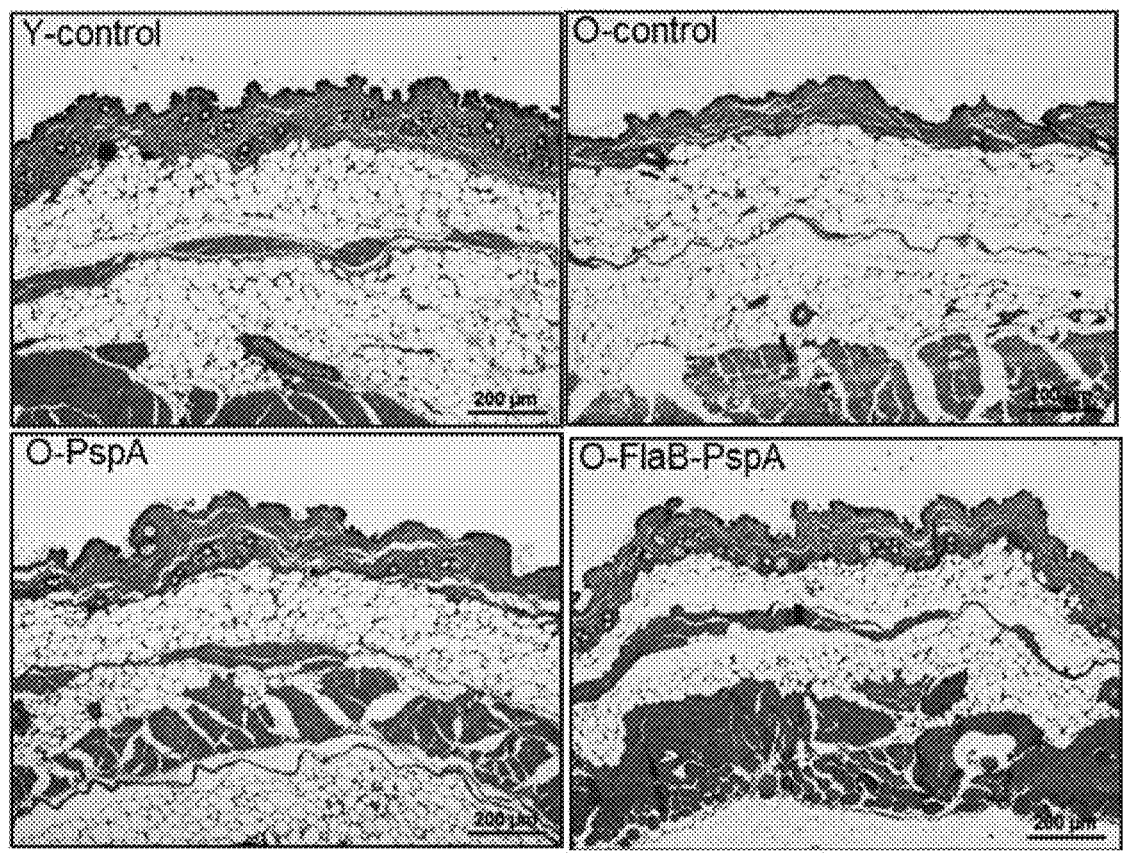

Example 4: Skin Histological Change of Aged Mice Through Immunization with Recombinant Protein The results of example 2 indicated that the hair condition of the aged mice became very favorable in the group continuously immunized with antigens, particularly, the recombinant protein. In order to prove these results in more detail, the results were confirmed through H&E staining. The H&E staining results are shown in FIG. 5. Young mice were used as a control group.

As a result of verifying H&E staining on the skin tissue of the back of the aged mice, it is general that the aging causes the progression of hair loss and the thinning of the dermis layer. It can be confirmed that, as for the young mice, the dermis layer is thick and a lot of hair follicles, that is, where hairs grow, exist in the dermis layer (Y-control). Whereas, it can be confirmed that, as for the aged mice, the dermis layer become thin and the number of hair follicles is significantly reduced (O-control). It could be verified that, when the aged mice were continuously immunized with an antigen (O-PspA) and a recombinant protein (O-FlaB-PspA), the dermis layer became thickened and the number of hair follicles was increased. Particularly, it could be verified that the number of hair follicles was significantly increased in the group immunized with FlaB-PspA recombinant protein.

As can be seen from the results of example 4, the histological assay confirmed that the continuous immunization with antigens improved the morphological findings of the aged mice (results of example 2). It could be confirmed through the histological assay that the amelioration of the progression of hair decoloration and hair loss of the aged mice, shown in the results of example 2, is due to the fact that the hair follicles are maintained in the aged mice due to the continuous immunization. In view of the results, it can be seen that the continuous immunization with the recombinant protein slows or prevents the progression of hair decoloration and hair loss occurring due to aging.

Example 5: Change in Bone Marrow Cells in Bone Marrow Through Immunization with Recombinant Protein The change in bone marrow cells in the bone marrow of the aged mice through the continuous immunization was verified, and the results are shown in FIG. 6. Non-immunized aged mice were used as a control group.

As a result of observing the change in bone marrow cells with respect to cells separated from the bone marrow of the aged mice, there is no difference between groups in view of cellularity.

As a result of confirming the proportions of bone marrow cells (megakaryocyte, myeloid, and erythroid lineages), it was verified that the bone marrow cells were generally well maintained and differentiated in the aged mice.

In addition, as a result of verifying the frequency of hematopoietic stem cells through immuno-staining using CD34, which is a hematopoietic stem cell indicator, it could be verified that CD34 was increased in the aged mice continuously immunized with FlaB-PspA recombinant protein rather than in the other groups.

As can be seen from the results of example 5, it could be verified that the continuous immunization with the recombinant protein is associated with not only the changes in the simple appearances but also the immune-related effects in the old mice.

Figure 7:
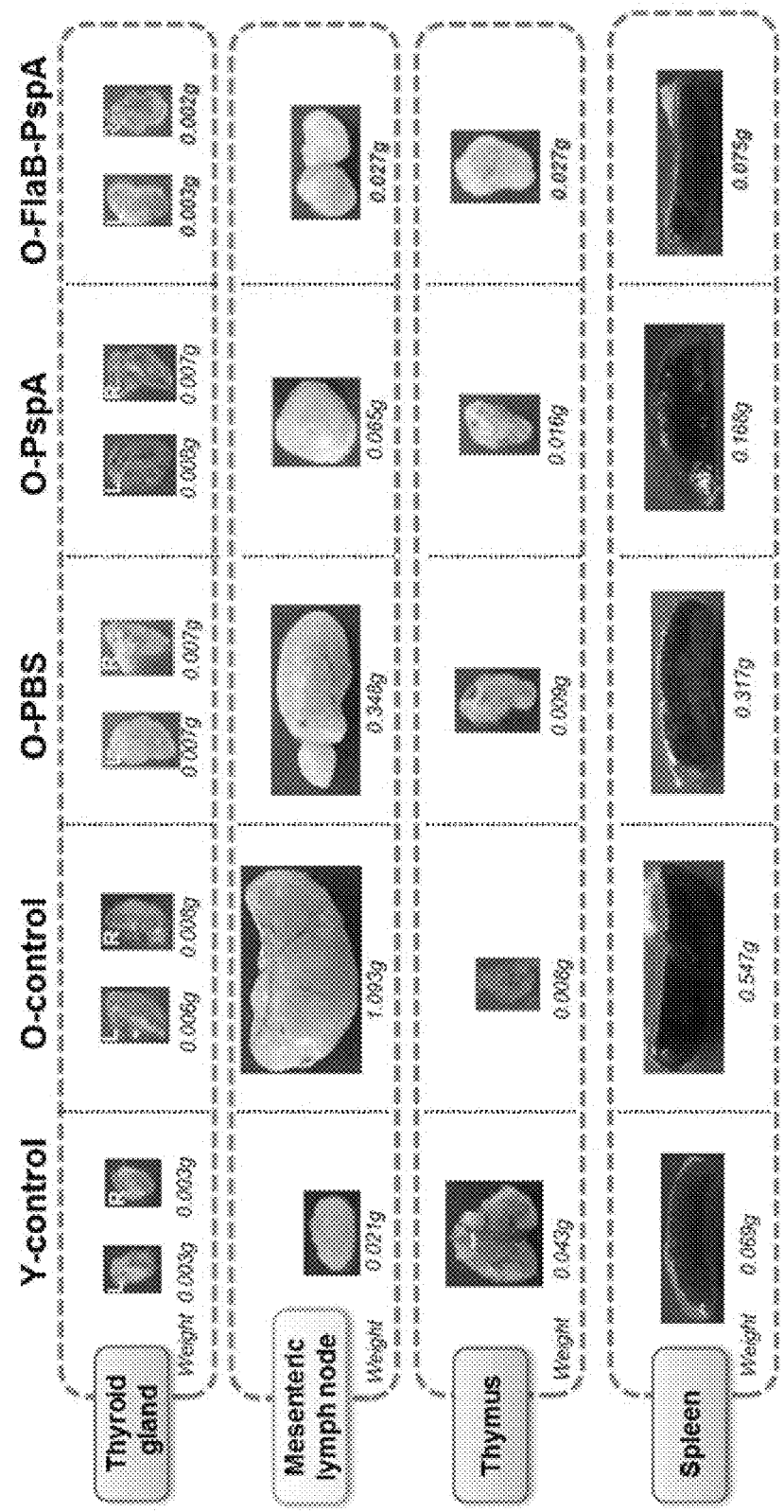

Example 6: Changes of Lymphatic System Organs Through Immunization with Recombinant Protein After the continuous immunization for an appropriate period of time, organs were extracted from the mice of each group, and the morphology and weight of each organ were measured. The measurement results are shown in FIG. 7. Young mice were used as a control group.

The tissues were extracted from the aged mice, and the morphological change and weight of each of the organs were measured. As a result, the difference caused by the continuous immunization was observed in the lymphatic system-related organs rather than in the other organs. Particularly, it was verified that the morphology and weight of the organs in the group immunized with FlaB-PspA recombinant protein were similar to those of the young mice.

Thymic involution with age is a general phenomenon, but it was verified that the thymus weight was increased in the aged mouse groups continuously immunized with antigens, and particularly, the thymus weight was significantly increased in the group immunized with FlaB-PspA recombinant protein. Besides, even though the mesenteric lymph nodes (MLNs) or the spleen, which are frequently used for systemic inflammation responses, mostly undergo a very hypertrophic morphology with age due to the continuous infection, it was verified that the thymus weight was larger in the aged mice continuously immunized with FlaB-PspA recombinant protein rather than in the other groups; and the spleen weight was smaller in the aged mice continuously immunized with FlaB-PspA recombinant protein rather than in the other groups, and the spleen morphology of the aged mice continuously immunized with FlaB-PspA recombinant protein was also similar to that of the young mice.

As can be seen from the results of example 6, it could be verified that the aged mice continuously immunized with antigens exhibited improved morphological features of the immune-related organs. Particularly, the aged mice immunized with FlaB-PspA recombinant protein were observed to have very similar organ morphological findings to the young mice.

Example 7: Change in Bone Mineral Density of Aged Mice Through Immunization with Recombinant Protein Spines were extracted from the aged mice, and the change in bone mineral density through the immunization with the recombinant protein of the aged mice was measured using micro-computer tomography (microCT). The measurement results are shown in FIG. 8. Young mice were used as a control group.

After eight times of continuous immunization, the spines were extracted from the aged mice, and the change in bone mineral density through immunization was measured using microCT. As a result, it could be verified that the bone mineral density was significantly improved in the group immunized with the recombinant protein. In connection with example 1, it could be thought that the facts that the body weight was not changed depending on the number of times of immunization and the feed intake was increased in only the group immunized with the recombinant protein are associated with the motion quantity of the aged mice, and it could be explained that, in this regard, the bone mineral density was more significantly increased in the group continuously immunized with the recombinant protein rather than in the other aged mouse groups.

Examples 8-16

Figure 9:
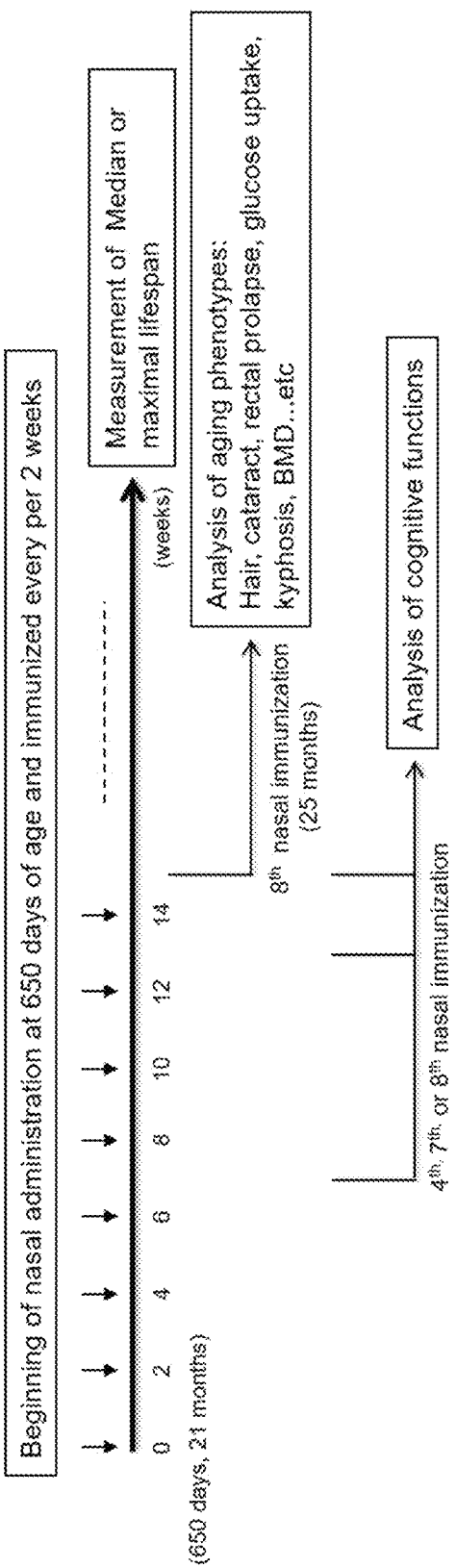

Materials and Methods
 Mice
 Female and male C57BL/6J aged mice were generated in house (by CHL at KRIBB, Korea) or purchased from the animal center in Korea Basic Science Institute (KBSI). All the mice were maintained in a specific pathogen-free (SPF) animal facility at the Clinical Vaccine R&D Center of Chonnam National University. All the mouse procedures were conducted in accordance with the guidelines of the Animal Care and Use Committee of Chonnam National University.
 Mucosal Immunization and Measurement of Life Span
 The mice were initially immunized at 650 days and continually immunized with phosphate-buffered saline (PBS, 16 µl), as a control, PBS containing FP (6.5 µg), FP SDM (6.5 µg), PspA (2.5 µg), or FlaB (4 µg) every 2 weeks via the intranasal route (FIG. 9). The principal endpoint was age at death (for mice found dead at daily inspections).
 Purification of FlaB-PspA and Mutant FlaB-PspA Recombinant Proteins
 The recombinant FlaB-PspA (FP) and site-directed mutant FlaB-PspA (FP SDM) proteins were prepared as previously described (D. Garigan et al., Genetics 161, 1101-1112 (2002); D. Gems et al., Genetics 154, 1597-1610 (2000)). Briefly, the proteins were purified from isopropyl β-D-1-thiogalactopyranoside (IPTG, 0.4 mM)-induced transformed Escherichia coli ER2566 strains (New England Biolabs, Beverly, Mass., USA) by affinity chromatography using chitin bead column (New England Biolabs) in accordance with the manufacturer's protocol.
 The purity of the recombinant proteins was confirmed by sodium dodecyl sulfate polyacrylamide gel electrophoresis (SDS-PAGE) and Western blot analysis using anti-FlaB and anti-PspA antibodies. Lipopolysaccharide (LPS) contamination was removed from the recombinant proteins using the Affinity Pak Detoxi-Gel Endotoxin Removing gel columns (Pierce Biotechnology Inc., Rockford, Ill., USA), and the residual LPS content of the proteins was determined using the gel-clotting Endosafe LAL Kit (Charles River Laboratories Inc., Charleston, S.C., USA). The LPS levels in FP or FP SDM proteins were less than that of the Food and Drug Administration (FDA) guidelines (<0.15 EU/30 g per mouse). The concentration of purified proteins was determined by the Bradford Assay.

Site-Directed Mutagenesis of FlaB and Expression Vector Construction
 Flagellin is the cognate ligand of TLR5. In *P. aeruginosa*, a short stretch of 10 amino acids (amino acids 88-97; LQRIRDLALQ; SEQ ID NO: 3) in the N-terminal region of the flagellin was predicted to be important for binding to TLR5. Site-specific mutations generated in the predicted TLR5-binding region of *P. aeruginosa* PAK flagellin reduced their ability to stimulate interleukin-8 release from A549 cells. We could identify the conserved TLR5-binding region in *Vibrio vulnificus* FlaB (amino acids 89-98).
 To abrogate the TLR5 recognition ability of FlaB, we constructed two site-directed mutations in the TLR5-binding region (92M to A; 95L to A) as showed in Extended Data FIG. 15a. The mutated FlaB DNA fragment was generated by crossover PCR by two sets of primers.
 The list of primers is as follows: F-FlaB-P1: 5'-GAATTC ATG GCA GTG AAT GTA AAT ACA A-3' (SEQ ID NO: 5), R-FlaB-P2: 5'-TTG TAG AGA TGC GTC ACG CGC ACG TTG TAG G-3' (SEQ ID NO: 6), F-FlaB-P3: 5'-CCT ACA ACG TGC GCG TGA CGC ATC TCT ACA A-3' (SEQ ID NO: 7), and R-FlaB-P4: 5'-CTGCAG TTA GCC TAG TAG ACT TAG CGC-3' (SEQ ID NO: 8).
 The underlined sequences indicate the restriction enzyme recognition sites. The mutated FlaB DNA fragment was cloned into the plasmid pTYB12 (New England Biolabs). The expected mutation was confirmed by DNA sequencing.
 The DNA fragment encoding the antigenic PspA polypeptide (D. Garigan et al., Genetics 161, 1101-1112 (2002)) was fused to the C-terminal of mutated FlaB and was expressed as the FP SDM proteins. The resulting expression plasmids were transformed into competent *E. coli* ER2566 strains (New England Biolabs) for protein expression.
 Analysis of Mice Phenotype Score
 The mice were observed every 2 weeks during the eight-time continual immunization. We monitored physical conditions of mice such as hair loss, rectal prolapse, and cataract by visual inspection. The mice phenotypes were assessed on the basis of the frailty index (FI) (Whitehead, J. C. et al., J Gerontol A Biol Sci Med Sci 69, 621-632 (2014); Fahlstrom, A. et al., Neurobiol Aging 32, 1868-1880 (2011)) and applied to the scoring system that was divided into grades from 1 (Good) to 4 (Severe) depending on each phenotype condition.
  a. Hair Loss
 We modified previously reported hair loss scoring systems to adjust to our model (Whitehead, J. C. et al., J Gerontol A Biol Sci Med Sci 69, 621-632 (2014); Honess, P. et al., Altern Lab Anim 33, 193-206 (2005)). The hair loss was scored by a progressive degree of hair loss at the back. A score of 1 denotes no detectable loss of hair. A score of 2 indicates few small patches or less than 10% of hair loss at the back. A score of 3 was given when several small patches or 20%-50% of hair loss at the back was observed. A score of 4 was marked when larger patches or generalized hair loss (not patchy) exceeds 50% of back hair was noted.
  b. Rectal Prolapse
 We modified previously reported rectal prolapse scoring systems to our ends (Adusumilli, S. et al., Colorectal Dis 15, e680-685 (2013); Wieslander, C. K. et al., Biol Reprod 80, 407-414 (2009)). The severity of rectal prolapse was scored by a progressive degree of protrusion from the anus. A score of 1 indicates no detectable rectal prolapse. A score of 2 means mild rectal prolapse. A score of 3 indicated moderate prolapse and a score of 4 represented severe rectal prolapse.

c. Cataract

Cataract was scored by a progressive degree of opacification in the posterior lens using a previously described opacification grading system (Geraldine, P. et al., Exp Eye Res 83, 1340-1349 (2006); Makri, O. E. et al., Mol Vis 19, 1188-1197 (2013)). A score of 1 indicates no opacity sign in the lens. A score of 2 was given to a slight degree of opacification or a randomly shaped lesion (amorphous pattern) in the lens. A score of 3 marks a diffuse opacification or a larger lesion of amorphous pattern in the entire lens. A score of 4 indicates an extensive thick opacification (hypermature cataract) in the entire lens.

Micro-CT Image Processing

Micro-computer tomography (CT) images for measurement of kyphosis and bone mineral density (BMD) were obtained using micro-CT (Inveon, Siemens Medical Soulutions, Malvern, Pa., USA) which uses multiple axial X-rays of the animal to generate cross-sectional information of 3-dimensional reconstruction of the animal or parts of the animal. The micro-CT system has a variable focus X-ray source, which provides resolution of up to 15 µm and a 125 mm detector capable of scanning an entire mouse in a single scan. Analysis of kyphosis and BMD measurement in micro-CT images was performed with PMOD software version 3.310 (PMOD Technologies Ltd., Zurich, Switzerland).

Analysis of Kyphosis

For analysis of kyphosis, spine was dissected after the eighth immunization and fixed in 10% neutral formation. The angle of spinal curvature was measured using the analysis of Cobb's angle as defined by the lines drawn to the seventh cervical vertebra (C7), maximal curvature, and the fifth lumbar (L5) vertebral endplates (Erb, M. et al., J Pharmacol Exp Ther 331, 787-795 (2009); Laws, N. et al., J Appl Physiol (1985) 97, 1970-1977 (2004)). The angle of spinal curvature was calculated by ImageJ software (National Institutes of Health, Bethesda, Md., USA).

Measurement of Bone Mineral Density

After the eight immunization, the right femur and spine were removed of the adherent soft tissues and fixed in 10% neutral formalin. The right femur and lumbar vertebrae (L3) in the spine were scanned for BMD by micro-CT. We drew the global region of interest (ROI) and defined the values using 30 slices approximately 0.3 mm from the distal femur and L3 in the spine. And then, the BMD was calculated by Housefield Unit (HU) value in global ROI. For accurate analysis of BMD, HU values of micro-CT image were converted to equivalent bone density (mg/cc) by the CT calibration method provided by Siemens. The values of BMD were estimated as the mean converted equivalent bone density within the global ROI.

Behavior Tests

Behavior tests were performed between 2 and 12 days after the fourth, seventh, or eighth intranasal immunization with FP or vehicle.

a. Open Field Test

The open field test has been described in a previous study (Kim, K. S. et al., Proc Natl Acad Sci USA 103, 3908-3913 (2006)). The locomotor activity was measured in the open field that was made of a white Plexiglas chamber (45 cm×45 cm×40 cm). Mice were habituated in the test room for 30 min. Each mouse was placed individually at the center of the open field and the horizontal locomotion was recorded for 30 min. The test was performed using a computerized video-tracking system (SMART; Panlab S.I., Barcelona, Spain).

b. Nesting Building

The mice were housed in single cages containing sawdust for 5 days. On the first day of testing, one piece of cotton (5×5 cm, Nestlets, Ancare, Bellmore, N.Y., USA) was introduced in the home cage to permit nesting. The presence and quality of nesting were rated 1 day later on a 5-point scale ranging from 1 to 5 as follows: 1=nestlet not noticeably touched (>90% intact), 2=nestlet partially torn up (50%-90% remaining intact), 3=mostly shredded but often no identifiable nest site, 4=an identifiable but flat nest, and 5=a (near) perfect nest. Immediately afterward, the mice were group-housed as before (Deacon, R. M. Nat Protoc 1, 1117-1119 (2006)).

c. Object Recognition Test

Novel object recognition is a validated and widely used test for assessing recognition memory (Antunes, M. et al., Cogn Process 13, 93-110 (2012); Akkerman, S. et al., Behav Brain Res 232, 317-322 (2012)). Mice were placed individually in a 40×20×20 cm3 testing chamber for 10 min with two identical objects (familiar, acquisition session). Then, the mice were returned to home cages and 1 day later placed back in the testing chamber in the presence of one of the original objects and one novel object (novel, recognition session) for 10 min. The original objects consisted of cylindrical wooden blocks measuring 10 cm high×2 cm diameter. The novel object consisted of a rectangular wooden block measuring 10 cm×2.5 cm×2 cm. The acquisition and recognition sessions were video recorded, and an observer who was blinded to drug treatment scored the time spent exploring the objects. The chambers and objects were cleaned with ethanol between trials. Exploration was defined as sniffing and touching the object with the nose and/or forepaws. Sitting on the object was not considered as exploratory behavior. In preliminary studies, naive mice exhibited no significant preference for the cylindrical or rectangular block. The time of exploring both objects was calculated. A preference score was calculated for each animal and expressed by the ratio of time spent exploring the novel object-time spent exploring the familiar object/(total time spent with both objects) on day 2.

d. Passive Avoidance Test

The test apparatus consisted of a light and a dark chamber (17×22×20 cm), each equipped with a shock-grid floor and a door between the two chambers. During the first day of testing, each mouse was placed in the light chamber and left to habituate to the apparatus for 5 min, while allowing it to explore the light and dark rooms. On the second day, the mice were placed in the light chamber. After 20 sec, the door was opened, and the mice were allowed to enter into the dark chamber such that all four paws were inside. When the mice entered the dark room, the door was closed, and one successive electric foot-shocks (0.1 mA, 2 sec) were delivered through the grid floor. After training, the mice were then returned to their home cages. After 7 days, the mice were individually replaced in the light chamber, and the latency to enter the dark chamber was measured, which was recorded as post-test. The cut-off time for the entry of the mouse into the dark chamber was 180 sec.

Statistical Analysis

Statistical analysis was performed using Prism 5 software (GraphPad, Inc., San Diego, Calif., USA). Differences between the experimental groups were analyzed by paired t-test and Mann-Whitney U-test. Survival rates were analyzed using Kaplan Meier plotting and Mantel-Cox log-rank test. The data shown are of at least three independent experiments and are represented as mean±SEM, except survival data, and considered statistically significant when P values were <0.05.

Immunological Analysis a. Analysis of Immune Cells by FACS

Isolation of Splenocytes and Thymocytes or Bone Marrow-Derived Cells

After eight times of FP or vehicle immunization from aged mice, spleen and thymus were dissected and cut into small pieces. To isolate splenocytes or thymocytes from individual mice, tissues were dissociated in RPMI 1640 medium supplemented with 10% FBS, 1% penicillin-streptomycin, 1% L-glutamine, and 0.1% β-mercaptoethanol. After harvesting single-cell suspensions through Cell Strainers (60 μm, BD Biosciences), the cells were washed with flow cytometry (FACS) staining buffer (eBioscience, #00-4222-57) and incubated for 2 min in ACK lysing buffer (Gibco #A10492-01), followed by centrifugation and wash with PBS, and final resuspension in FACS buffer. For isolation of bone marrow (BM)-derived cells, BM cells were isolated from femur and tibiae. Mononuclear cells were isolated by discontinuous density centrifugation using Nycoprep (Accurate Chemical and Scientific, Westbury, N.Y., USA) according to the manufacturer's instructions and labeled with a cocktail of anti-mouse antibodies: CD3, B220, CD11b, Gr-1, and Ter119 (BD Biosciences). Lin-cells were obtained using anti-rat Dynal beads (Invitrogen) according to the manufacturer's instructions and cells stained for flow cytometry.

Flow Cytometry Analysis

Single-cell suspensions were prepared from spleen and thymus or bone marrow. For cell surface staining of various marker in splenocytes and thymocytes, cells were blocked with Fc receptors (FcR) blocking reagents in FACS buffer and stained with different combinations of fluorochrome-conjugated antibodies (all from BD Biosciences) in FACS staining buffer for 20 min at RT in the dark. All antibodies for FACS were purchased BD Biosciences as follow: CD3-FITC, CD4-PE, CD8-APC, CD44-PE-Cy7, CD62L-APC, F4/80-FITC, CD11b-PE, CD11c-FITC, Ly6C-FITC, MHC-II-PE-Cy7, B220-FITC, CD19-PE, Ter119-FITC, C-kit-PE-Cy5, Sca1-APC-Cy7, CD34-PE, Flk2-APC. For intracellular staining of cytokine expression in splenocytes, the cells were stimulated with anti-CD32 (1 ug/ml) (abcam, #41899) for 4 hr. Intracellular staining was carried out after staining of surface markers. Cells were fixed with 4% paraformaldehyde and permeabilized using FACS Permeabilizing Solution (BD Biosciences). Then samples were incubated with IL-2-PE, TNF-α-PE, and IL-10-PE (BD Biosciences). Flow cytometry analysis FACS data were acquired using a FACS Ariall (BD Biosciences) and analyzed with FlowJo software (Tree star, Ashland, Oreg., USA).

b. Analysis of sIgA from Feces

While immunizing eight times of FP or vehicle immunization, feces sample was collected at every 2 weeks after immunization to determine the PspA-specific secretory IgA (sIgA) production by ELISA. The ELISA was performed as previously described (Lim J S et al Aging Cell 2015). Briefly, feces were lysed with blocking buffer (0.05% Tween-20, 1 mM ethylenediaminetetraacetic acid, and 0.5% bovine serum albumin) and centrifuged for 30 min at 13,000 rpm, and then collected supernatants. After coating the plates with PspA proteins (1 ug), feces samples were incubated and washed. The sIgA was detected by adding TMD (3,3',5,5'-tetramethylbenzidine) substrate solution (BD Bioscience, San Diego, Calif., USA). The absorbance was read on a microplate reader (Molecular Devices Corp., Menlo, Calif., USA) at 450 nm. The titer represents the reciprocal of the dilution that yielded an optical density of 0.1 at 450 nm.

Metabolic Analysis a. Analysis of Leptin in Serum

After eight times of immunization of vehicle- or FP-immunized aged mice, blood was collected from heart of anesthetized mice. Blood was deposited in serum separator gel tubes (BD Bioscience) and centrifuged for serum separation. The quantitative determination of serum leptin was conducted by ELISA using commercially available reagent kit, DuoSet®ELISA (R&D Systems, Minneapolis, Minn., USA) in accordance with the manufacturer's instructions.

b. Brain Glucose Uptake by Micro-PET

Micro-PET images using [$^{18}$F]FDG were obtained by a dedicated small-animal PET scanner (Inveon; Siemens Medical Solutions, Erlangen, Germany). [$^{18}$F]FDG (0.2 mCi/150 μl) was injected in young mice and FP- or vehicle-immunized aged mice through the tail vein. The 10 min static micro-PET images were acquired at 30 min after injection. During the micro-PET scanning, the animals were anesthetized by inhalation of 1.0-1.2% isoflurane in $O_2$. The micro-PET images were reconstructed by three dimension ordered subset expectation maximization (OSEM3D) algorithm (number of iterative: 4) which is an iterative method. The micro-PET images were analyzed by PMOD software 3.310 (PMOD Technologies LLC, Zurich, Switzerland). Images were rearranged on a short, horizontal and vertical axial and counts in images were converted to standardized uptake value (SUV). VOIs (voxel of interest) were drawn in brain region using PMOD option which is a mouse M. Mirrione-FDG template. The average glucose uptake of whole brain was calculated based on the SUV in drawn VOIs.

Results

Example 8: Survival Patterns of Aged Mice after Immunization

To evaluate that mucosal immune stimulation via TLR5 signaling might intervene aging process and may extend both lifespan and healthspan of aged animals, we first monitored median and maximal survival patterns of these mice concomitantly with aging-related health and functional parameters after FP nasal immunization (FPNI). FPNI was initiated at 650 days in both male and female mice and continued with 2-week intervals (FIG. 9).

Survival and anti-aging effect of a mixture of F and P in addition to FP fusion protein was analyzed and found FP fusion protein was much better than the mixture (Table 1). Table 1 shows overall survival test in male mice

TABLE 1

| Treatment regimens | Symptom[a] | |
|---|---|---|
| | Spontaneous tumor[b] | Liver abnormality[c] |
| Saline | 8/10 (80%) | 7/10 (70%) |
| FlaB + PspA (Mix) | 5/11 (45%) | 4/11 (36%) |
| FlaB – PspA (Fusion) | 4/11 (36%)* | 1/11 (9%)** |

[a]Statisical significance was determined using $\chi^2$ test.
*P < 0.05 and **P < 0.005 vs. saline injected group.
[b]Number of tumor bearing mice in internal organs. Visual inspection only
[c]Number of mice with abnormality (tumor, liver cirrhosis) in liver tissues. Visual inspection only.

Example 9: Extension of Lifespan in Aged Mice after Immunization

Figure 10A:
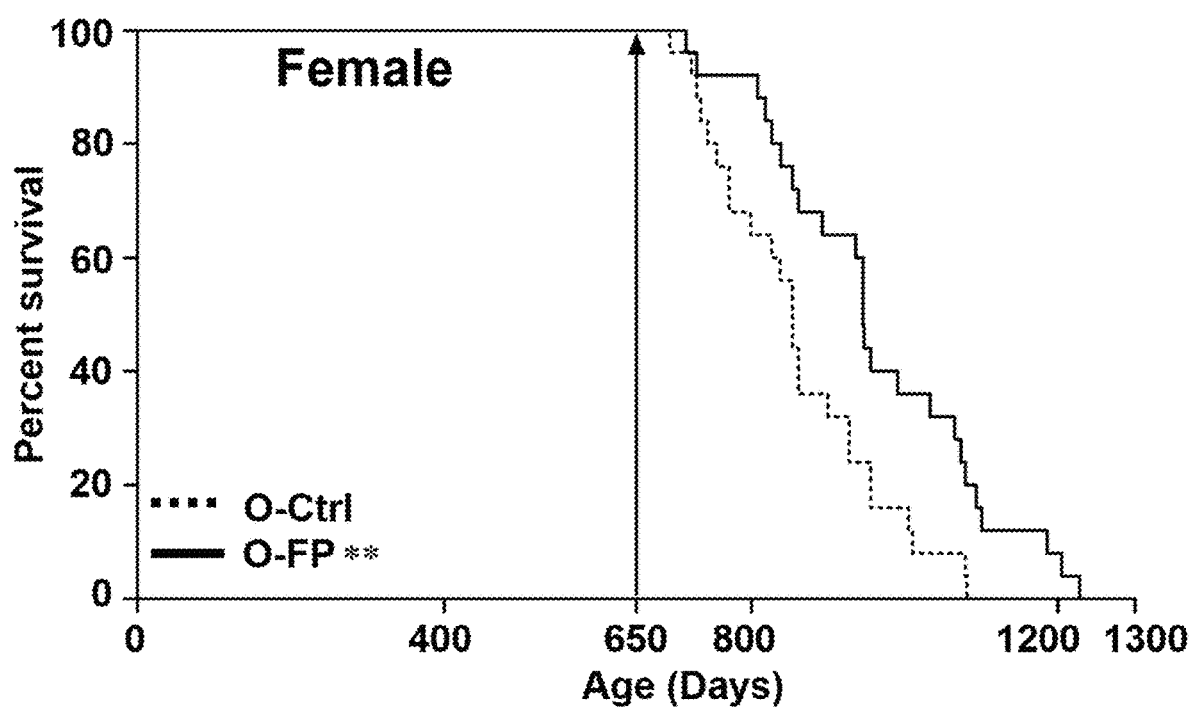
Figure 10B:
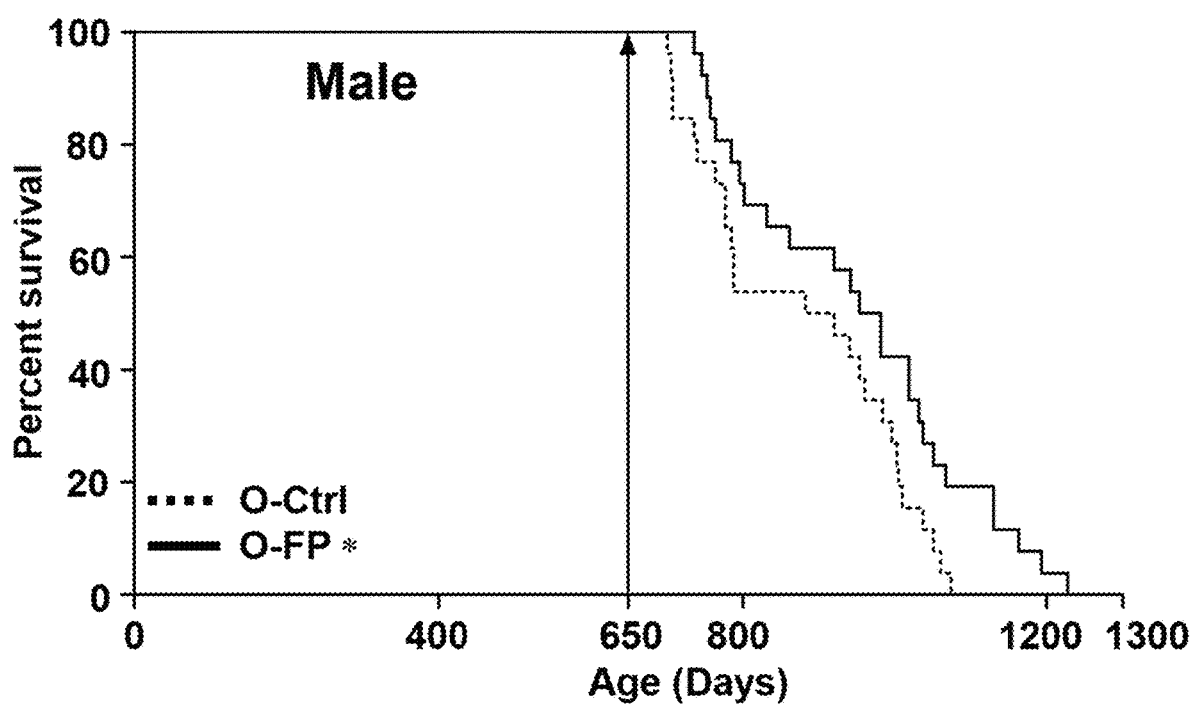

As shown in FIGS. 10a and 10b, FPNI significantly extended the median and maximal lifespan in both female and male mice compared with vehicle-treated control mice. Median survival was prolonged by 10.8% for females and 7.3% for males. Maximal survival was extended by 17.4% for females and 10.7% for males (Table 2). FP indicates FlaB-PspA recombinant proteins. Table 2 shows the FPNI-dependent extension of median and maximal survival in female and male mice.

TABLE 2

| | Median Lifespan (50%) | | | Maximal Lifespan (90%) | | |
|---|---|---|---|---|---|---|
| Sex | O-Ctrl | O-FP | Percent Increase | O-Ctrl | O-FP | Percent Increase |
| Female | 854 day | 946 day | 10.8% | 1010 day | 1186 day | 17.4% |
| Male | 902 day | 968 day | 7.3% | 1051 day | 1163 day | 10.7% |

The extension of lifespan in these mice is comparable to that of rapamycin, when administered starting at 600 days of age (D. E. Harrison et al., Nature 460, 392-395 (2009)). Note that 650 days (when we initiated FPNI) would be the latest initiation of any intervention for extension of longevity.

Example 10: Improvement of Healthspan in Aged Mice after Immunization—Hair Loss, Rectal Prolapse and Cataracts To determine whether FPNI enhanced the healthspan, we performed a second round of FPNI starting at 650 days (21 months) and assessed physical and functional aging phenotypes after the eighth treatment (FIG. 9). For a comparison of physical phenotypes, we monitored hair loss, rectal prolapse, and eye lens opacity in both sexes (Tables 3 and 4). Tables 3-4 show score mean of mouse phenotypes of hair loss, cataract and rectal prolapse in both of female and male. Table 5 shows score mean of mouse phenotypes from O-FP and O-FP SDM-immunized mice.

Figure 10C:
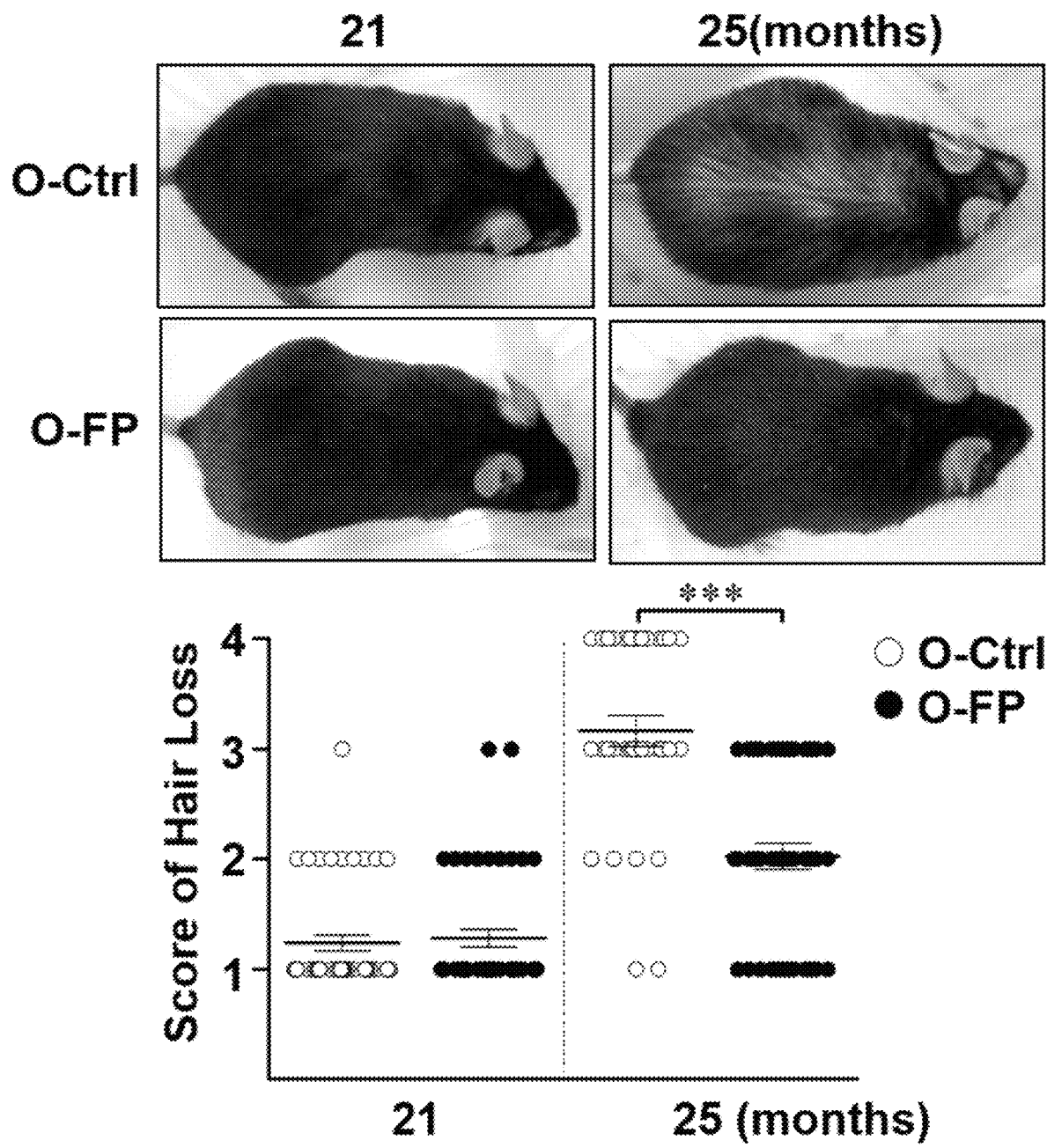

After four months, FPNI led to significant prevention of hair loss (FIG. 10c), rectal prolapse and cataracts (FIGS. 11a and 11b).

TABLE 3

| Age of animal (Months) | | Immunization frequencies | Female | | |
|---|---|---|---|---|---|
| | | | Hair loss | Cataract | Rectal Prolase |
| 21 | 0 | O-Ctrl (n = 46) | 1.41 ± 0.07 | 1.02 ± 0.02 | 1.02 ± 0.02 |
| | | O-FP (n = 46) | 1.43 ± 0.07 | 1.04 ± 0.03 | 1.02 ± 0.02 |
| 22 | 2nd | O-Ctrl (n = 45) | 1.58 ± 0.08 | 1.02 ± 0.02 | 1.07 ± 0.05 |
| | | O-FP (n = 46) | 1.50 ± 0.09 | 1.02 ± 0.02 | 1.02 ± 0.02 |
| 23 | 4th | O-Ctrl (n = 43) | 1.98 ± 0.12 | 1.14 ± 0.09 | 1.21 ± 0.09 |
| | | O-FP (n = 46) | 1.61 ± 0.09* | 1.04 ± 0.03 | 1.02 ± 0.02 |
| 24 | 6th | O-Ctrl (n = 40) | 2.40 ± 0.14 | 1.40 ± 0.11 | 1.48 ± 0.12 |
| | | O-FP (n = 43) | 1.70 ± 0.10*** | 1.07 ± 0.04* | 1.05 ± 0.03*** |
| 25 | 8th | O-Ctrl (n = 36) | 2.56 ± 0.16 | 1.67 ± 0.14 | 1.53 ± 0.12 |
| | | O-FP (n = 43) | 1.70 ± 0.11*** | 1.12 ± 0.05*** | 1.07 ± 0.04*** |

Score: 1 (Good)~4 (Severe)
Score of mouse phenotypes is shown as mean ± SEM.
*$P < 0.05$; $P < 0.01$; *$P < 0.001$, O-Ctrl vs. O-FP-immunized mice.

TABLE 4

| Age of animal (Months) | Immunization frequencies | Male | | |
|---|---|---|---|---|
| | | Hair loss | Cataract | Rectal Prolase |
| 21 | 0 | O-Ctrl (n = 26) | 1.12 ± 0.06 | 1.00 ± 0.00 | 1.04 ± 0.04 |
| | | O-FP (n = 26) | 1.04 ± 0.04 | 1.00 ± 0.00 | 1.00 ± 0.00 |
| 22 | 2nd | O-Ctrl (n = 24) | 1.21 ± 0.08 | 1.04 ± 0.04 | 1.00 ± 0.00 |
| | | O-FP (n = 26) | 1.04 ± 0.04* | 1.00 ± 0.00 | 1.00 ± 0.00 |
| 23 | 4th | O-Ctrl (n = 22) | 1.55 ± 0.10 | 1.14 ± 0.07 | 1.00 ± 0.00 |
| | | O-FP (n = 26) | 1.19 ± 0.08** | 1.04 ± 0.04 | 1.00 ± 0.00 |
| 24 | 6th | O-Ctrl (n = 20) | 1.50 ± 0.10 | 1.35 ± 0.11 | 1.00 ± 0.00 |
| | | O-FP (n = 24) | 1.25 ± 0.09 | 1.08 ± 0.06** | 1.00 ± 0.00 |
| 25 | 8th | O-Ctrl (n = 19) | 1.95 ± 0.08 | 1.37 ± 0.11 | 1.00 ± 0.00 |
| | | O-FP (n = 21) | 1.48 ± 0.10** | 1.05 ± 0.05** | 1.00 ± 0.00 |

Score: 1 (Good)~4 (Severe)
Score of mouse phenotypes is shown as mean ± SEM.
*$P < 0.05$; $P < 0.01$; *$P < 0.001$, O-Ctrl vs. O-FP-immunized mice.

Figure 10D:
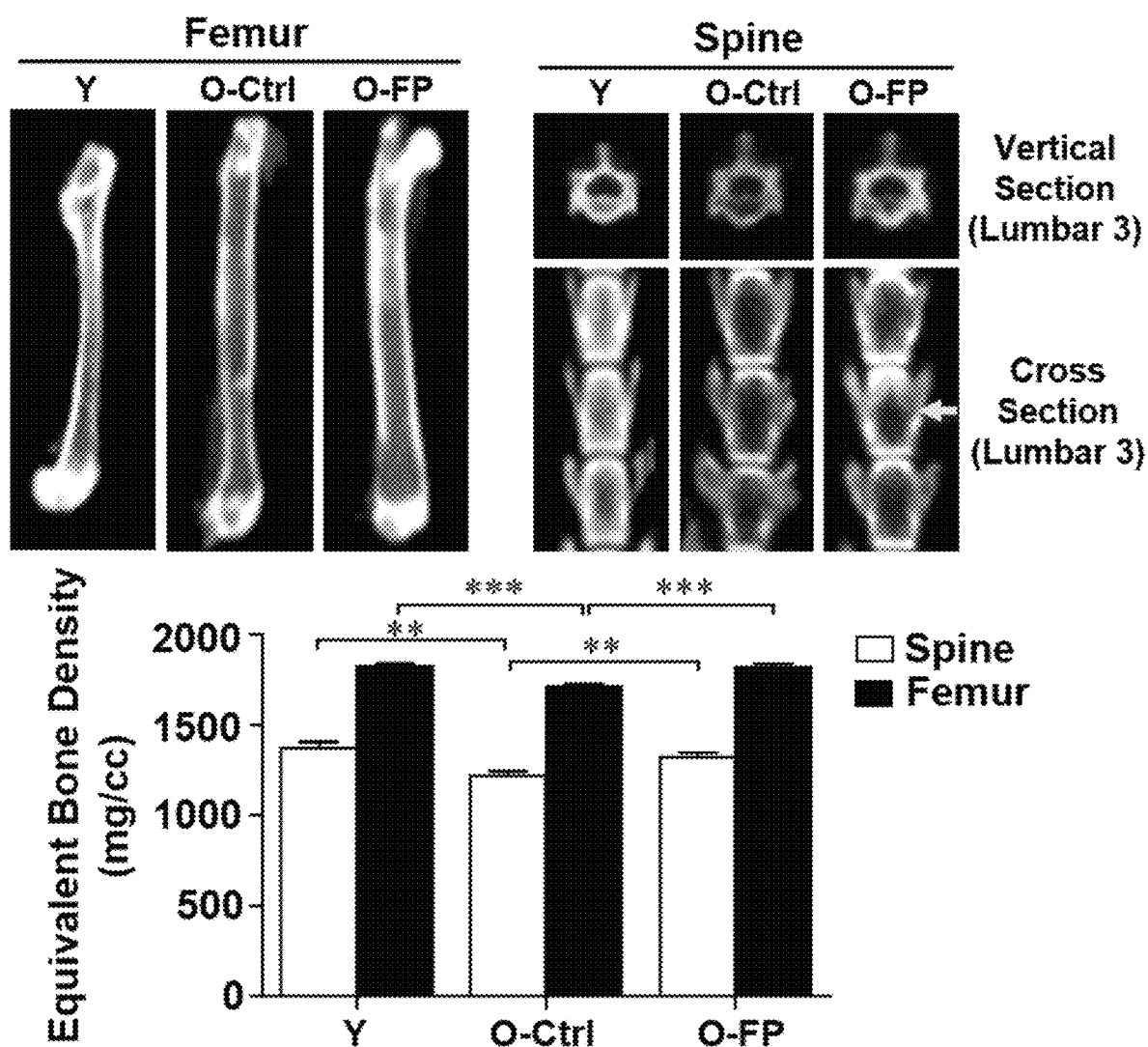

Example 11: Improvement of Healthspan in Aged Mice after Immunization—Prevention of Kyphosis and Osteoporosis While control aged mice had severe kyphosis and significant decrease of bone mineral density compared with control young mice. FPNI-aged mice showed elevated bone mineral densities in both spine and femur (FIG. 10d), and better maintained spinal curve angle (FIG. 11c).

Example 12: Enhancement of Immune Functions in Aged Mice after Immunization

Figure 10E:
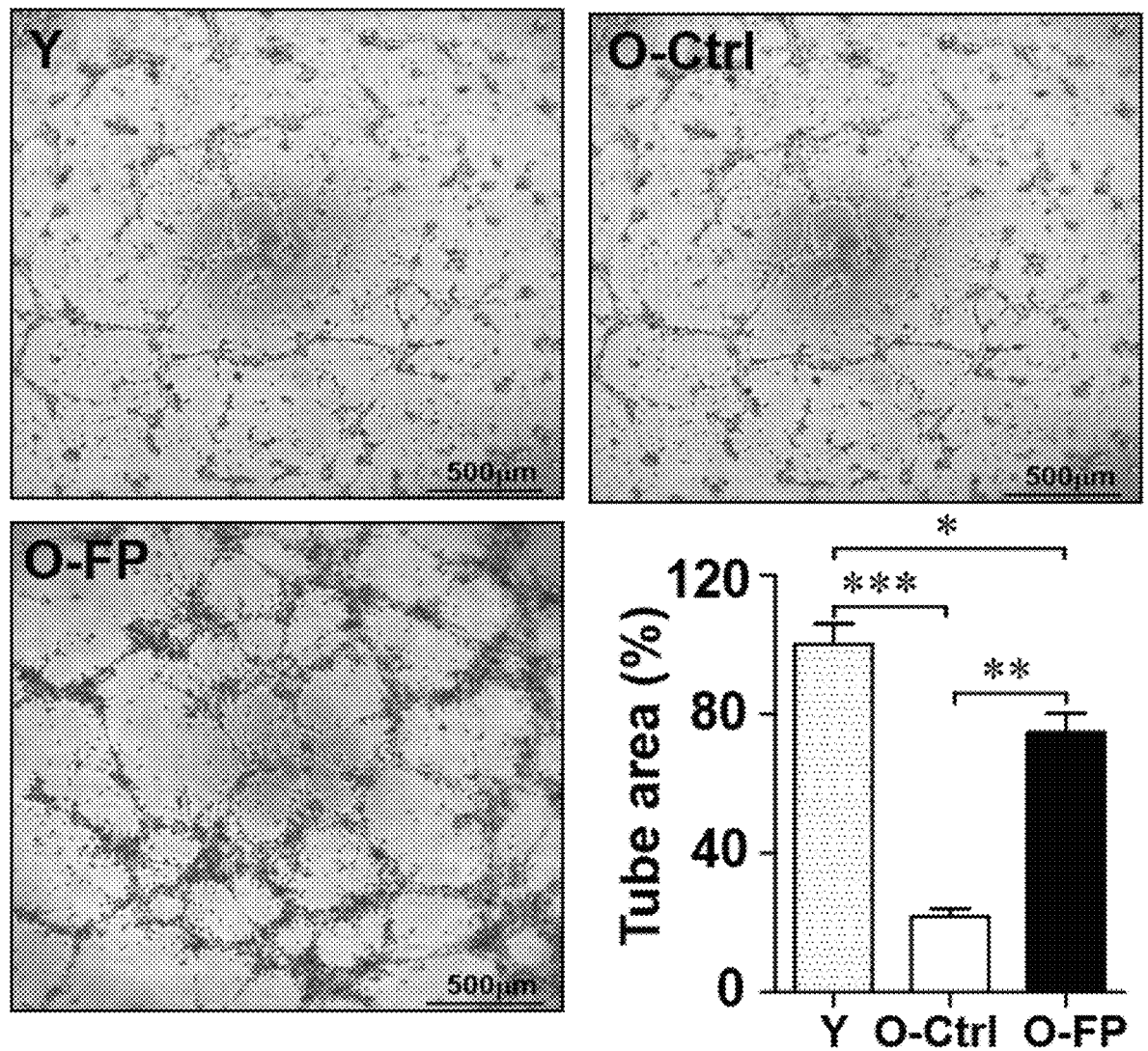

FPNI also led to an increase in the (the higher) activity of bone marrow-derived stem cells, as analyzed by tube formation (FIG. 10e).

Figure 10G:
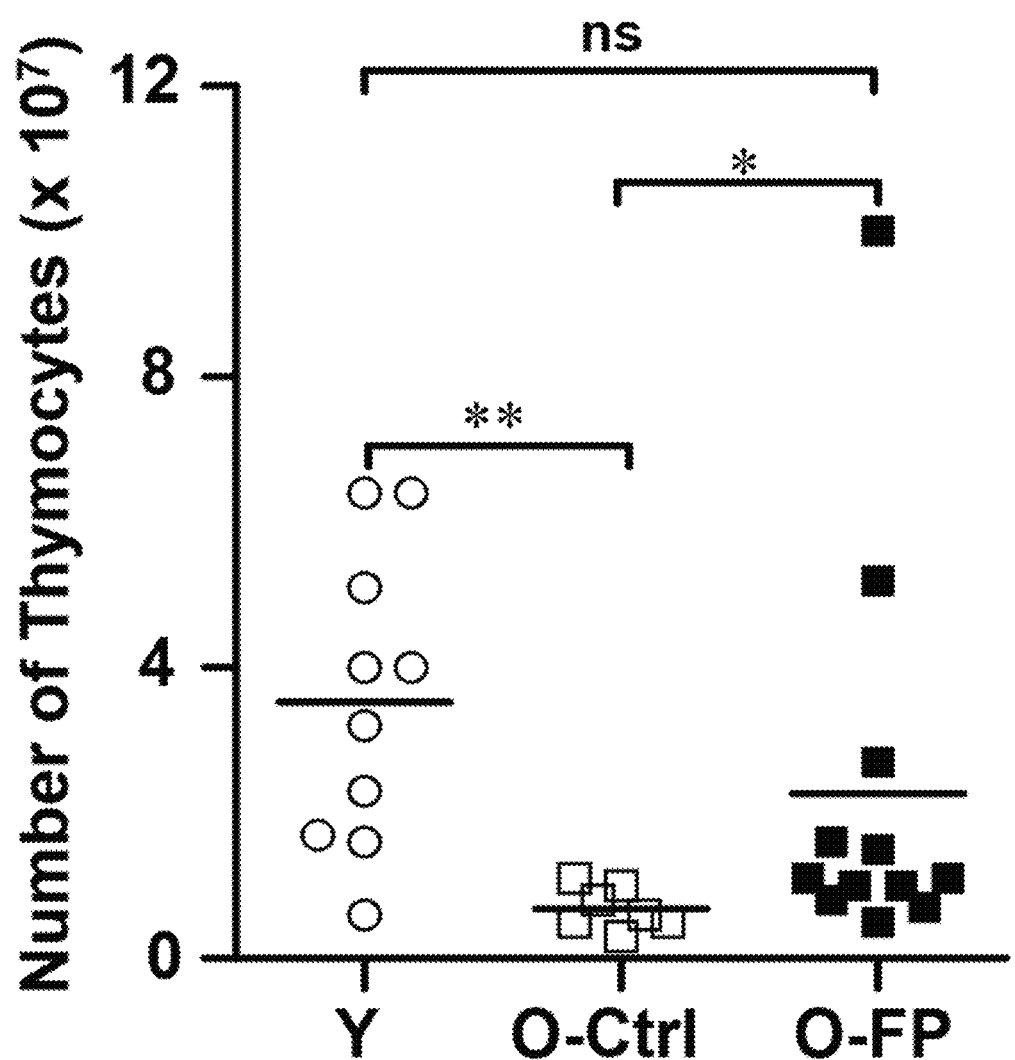
Figure 10H:
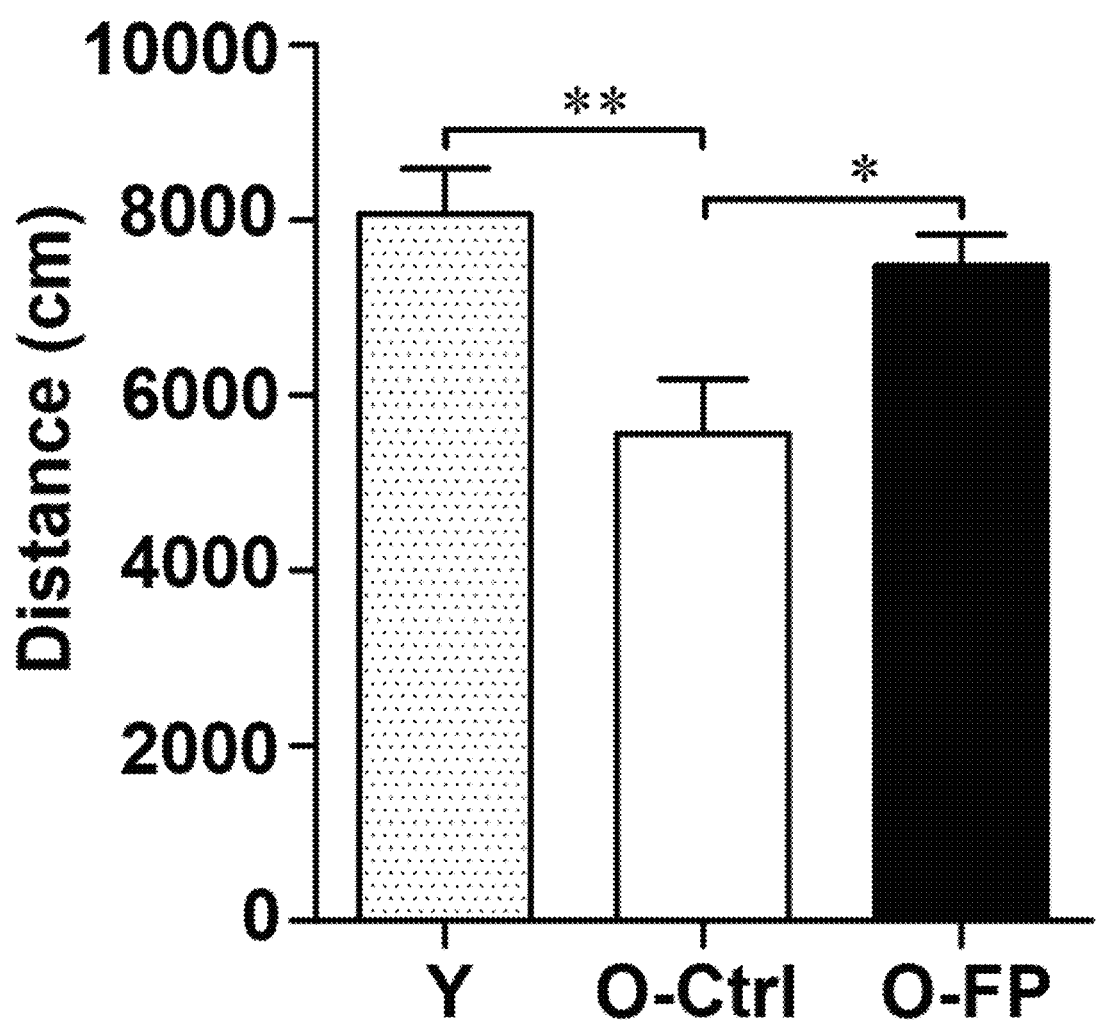
Figure 10I:
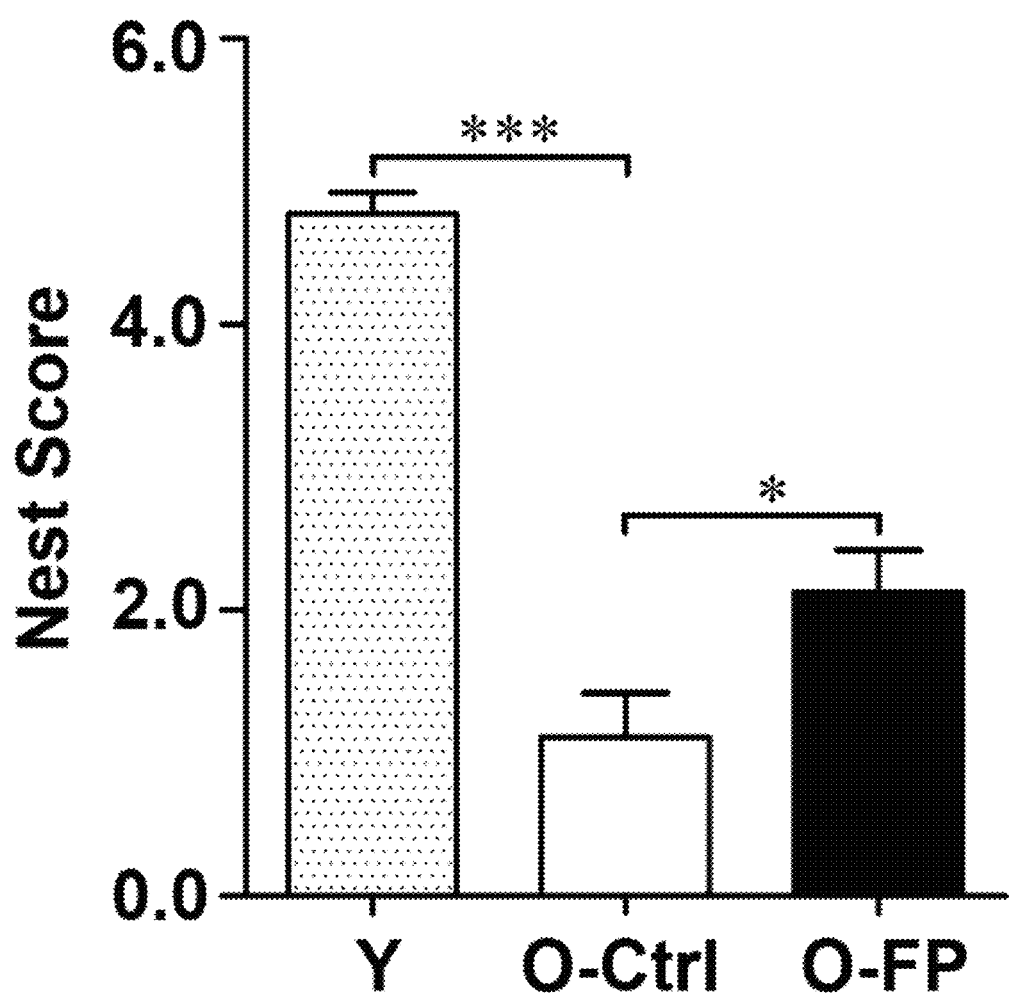
Figure 10J:
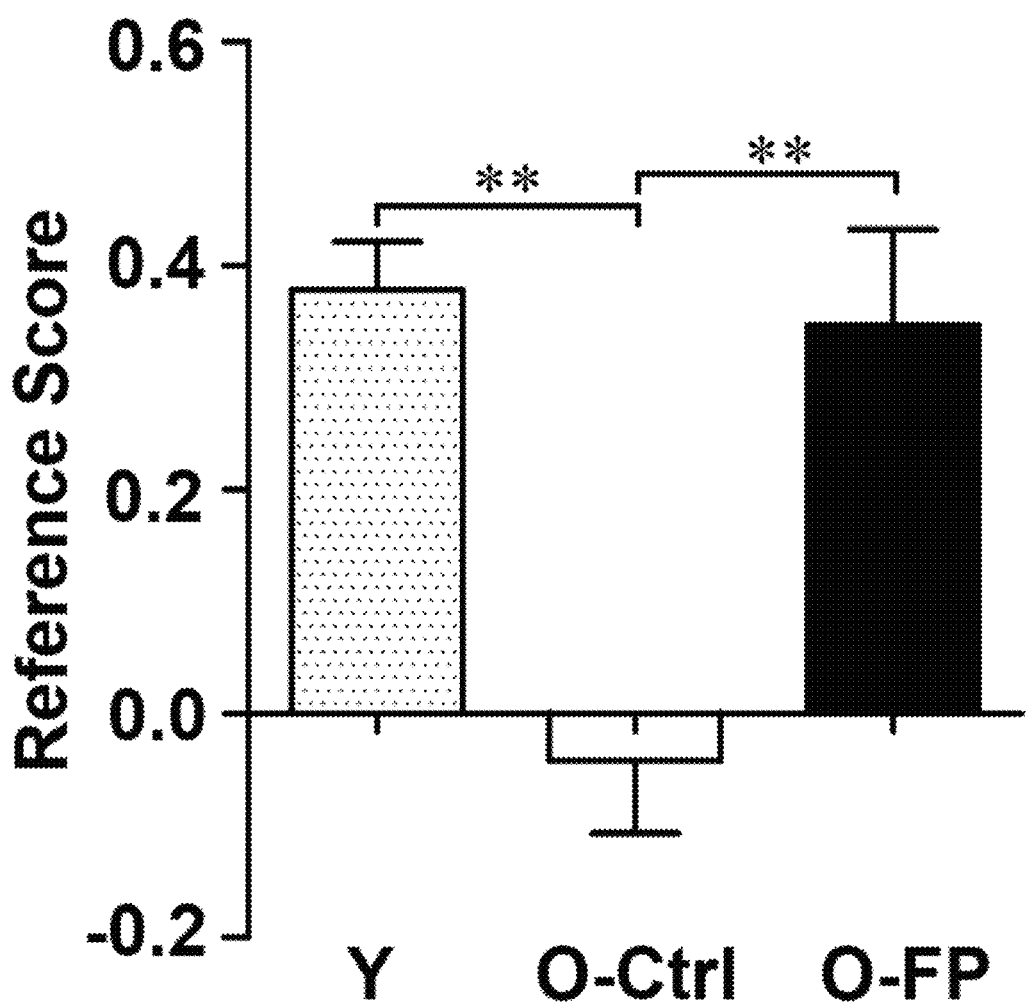
Figure 10K:
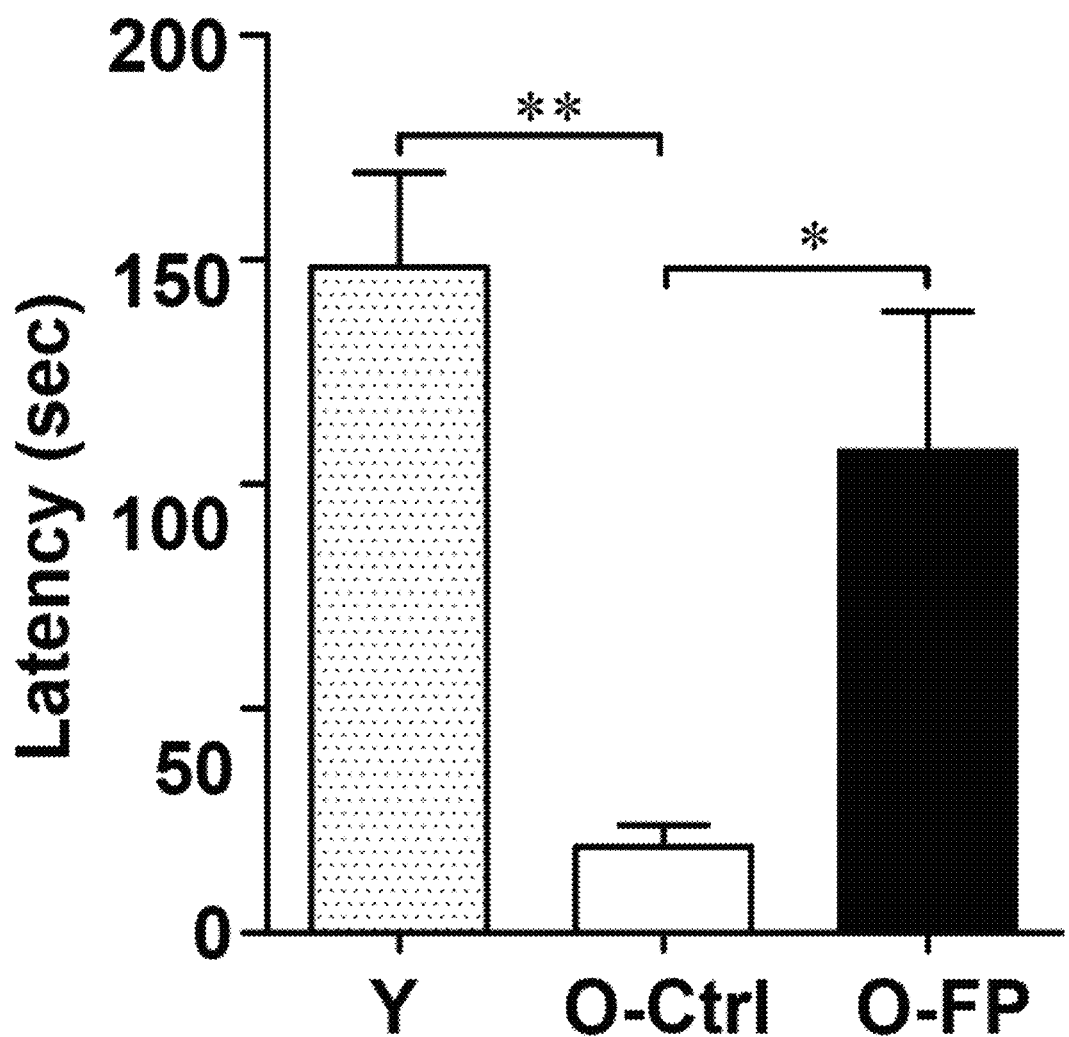
Figure 12A:
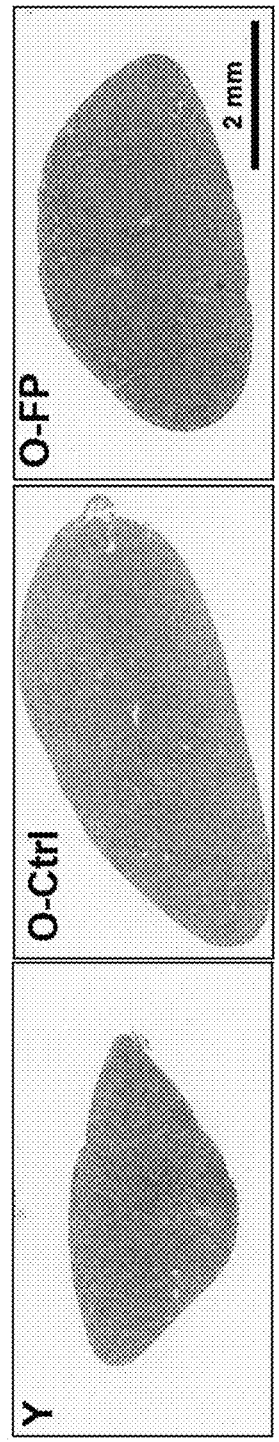
Figure 12B:
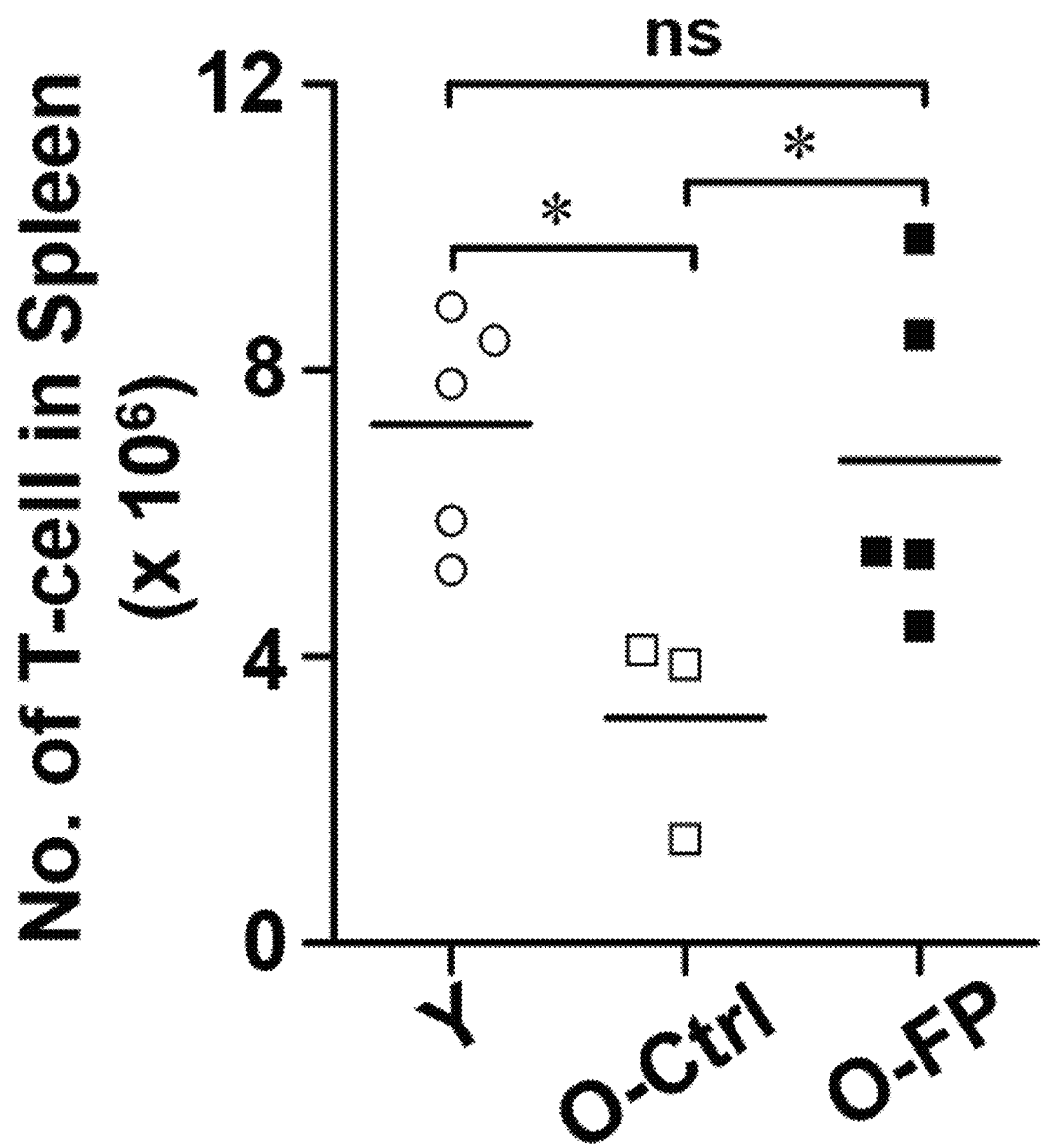
Figure 12C:
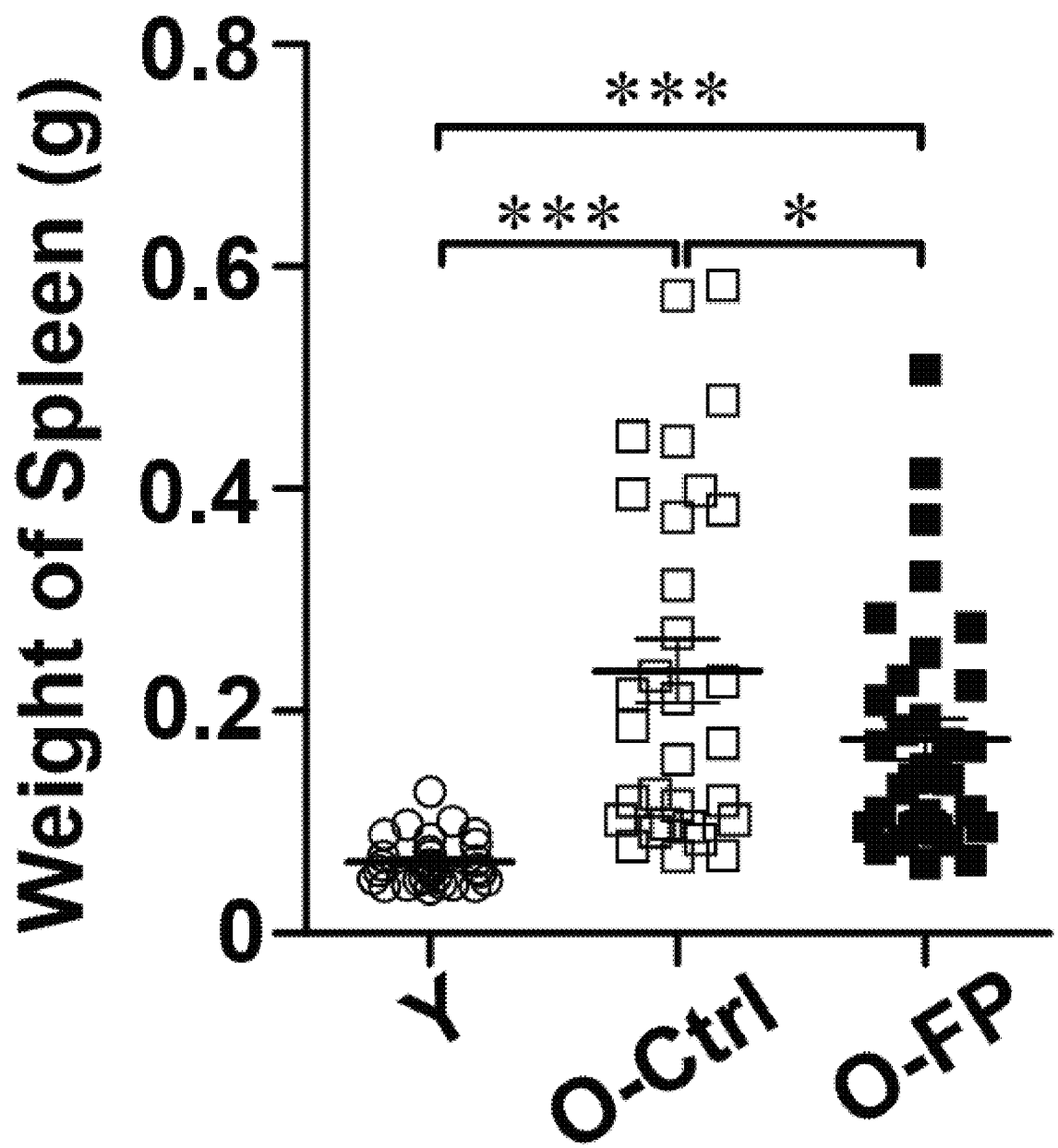
Figure 12D:
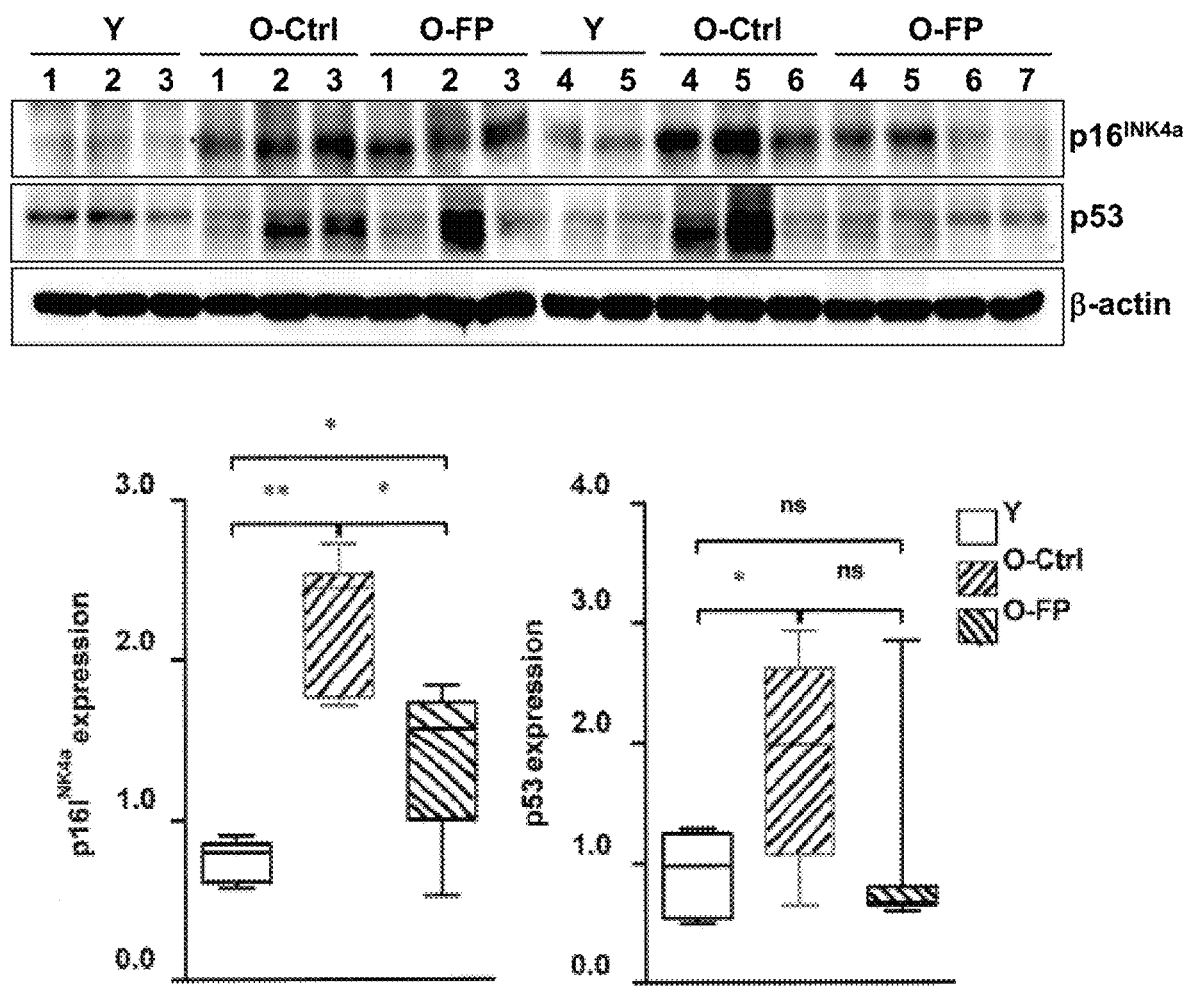
Figure 13A:
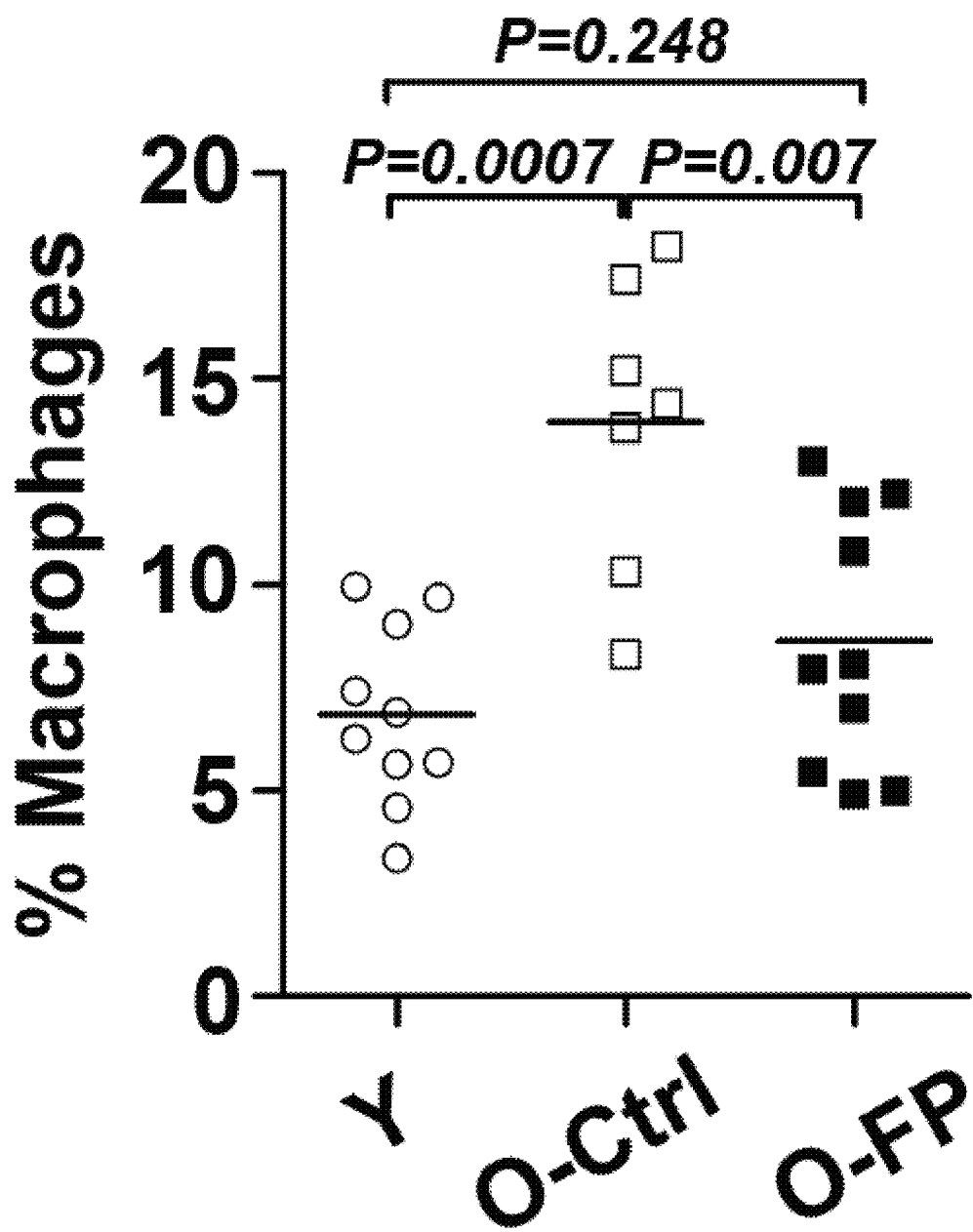
Figure 13B:
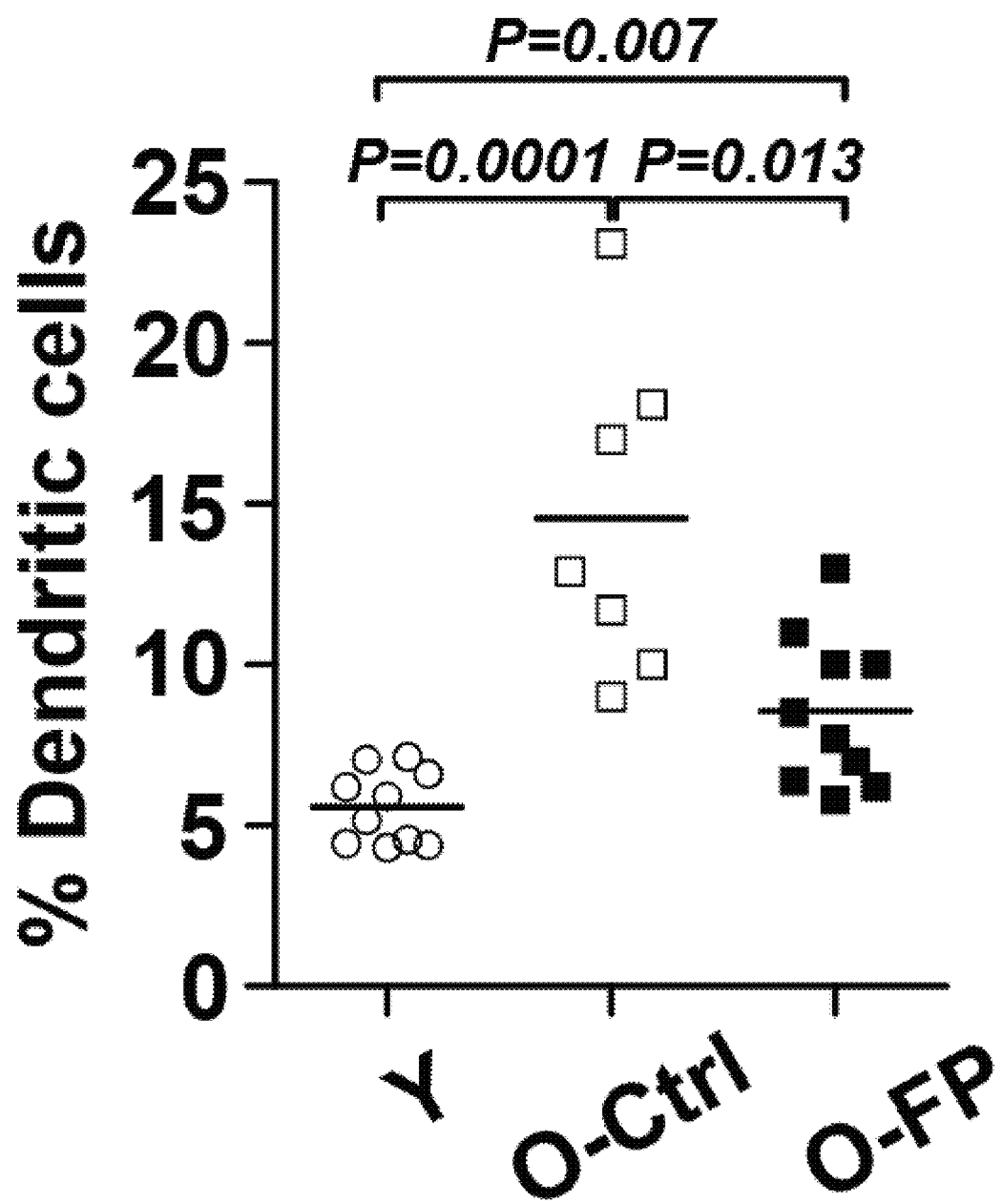
Figure 13C:
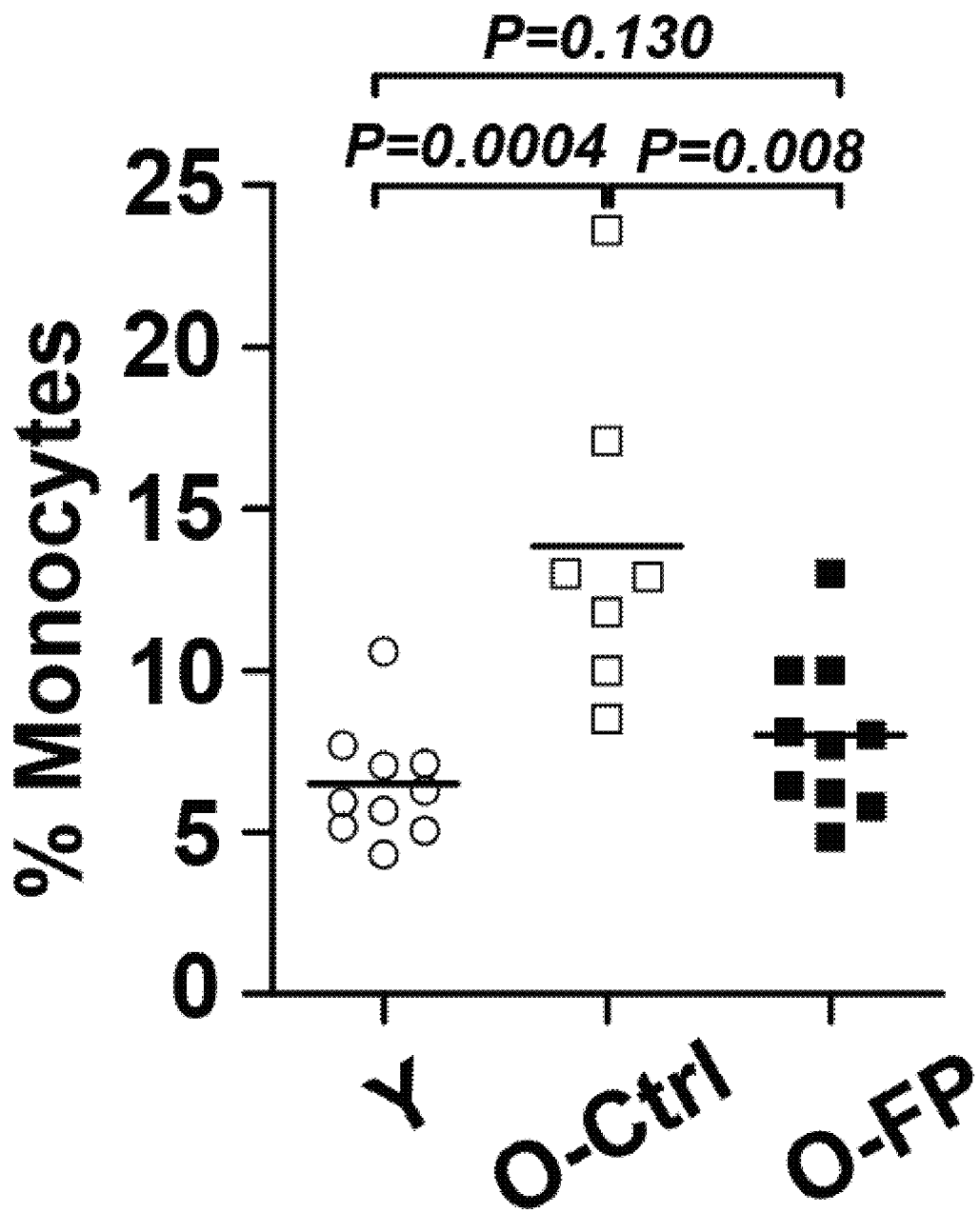
Figure 13D:
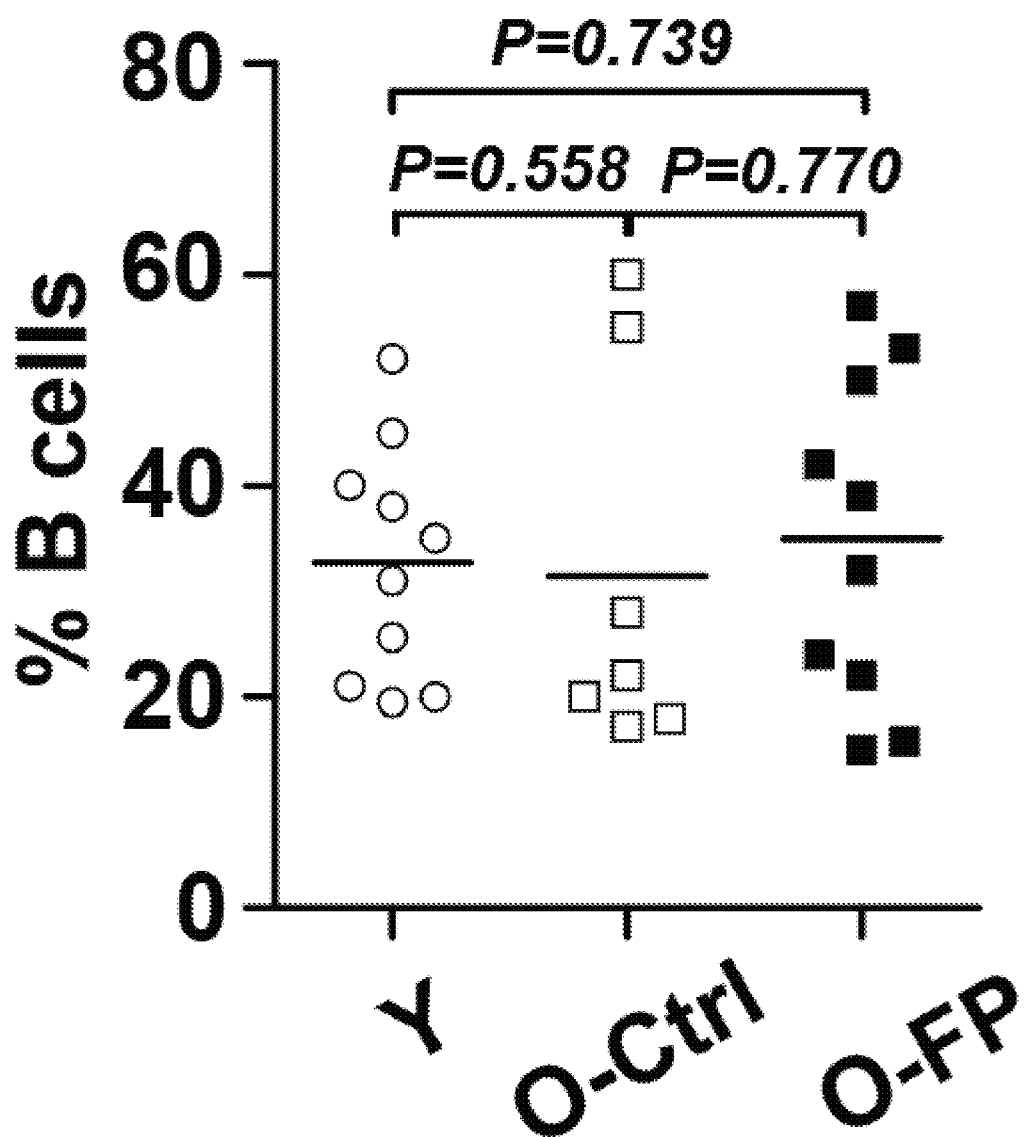
Figure 13E:
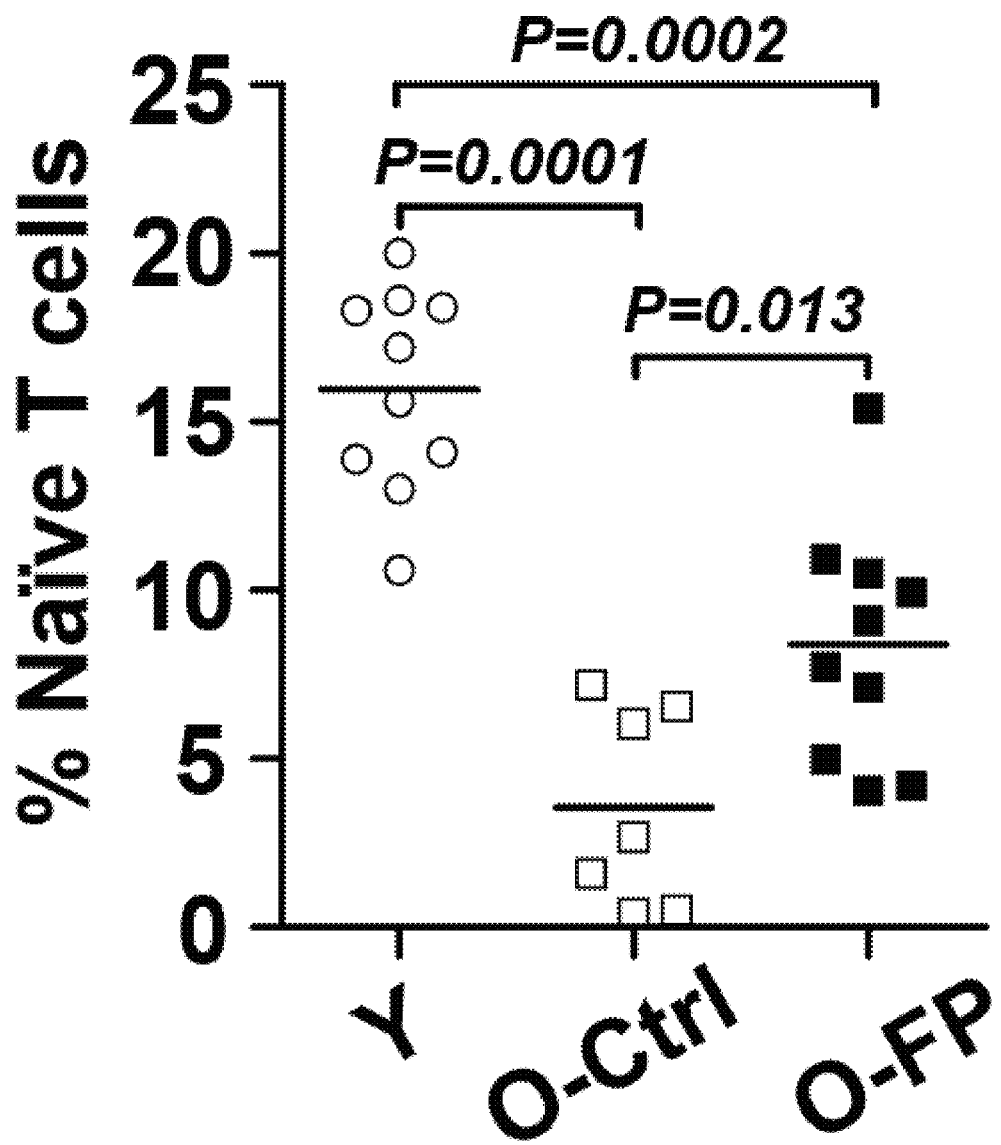
Figure 13F:
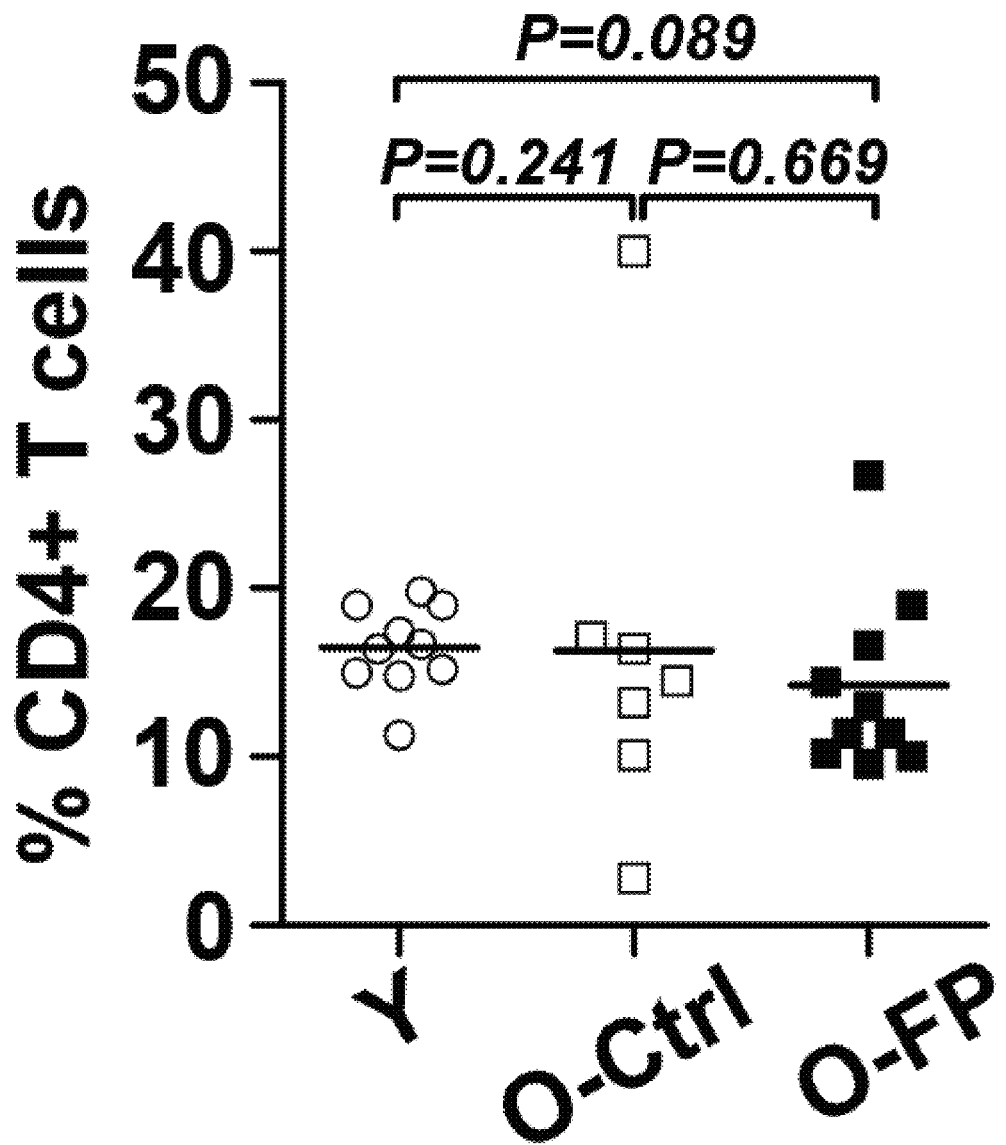
Figure 13G:
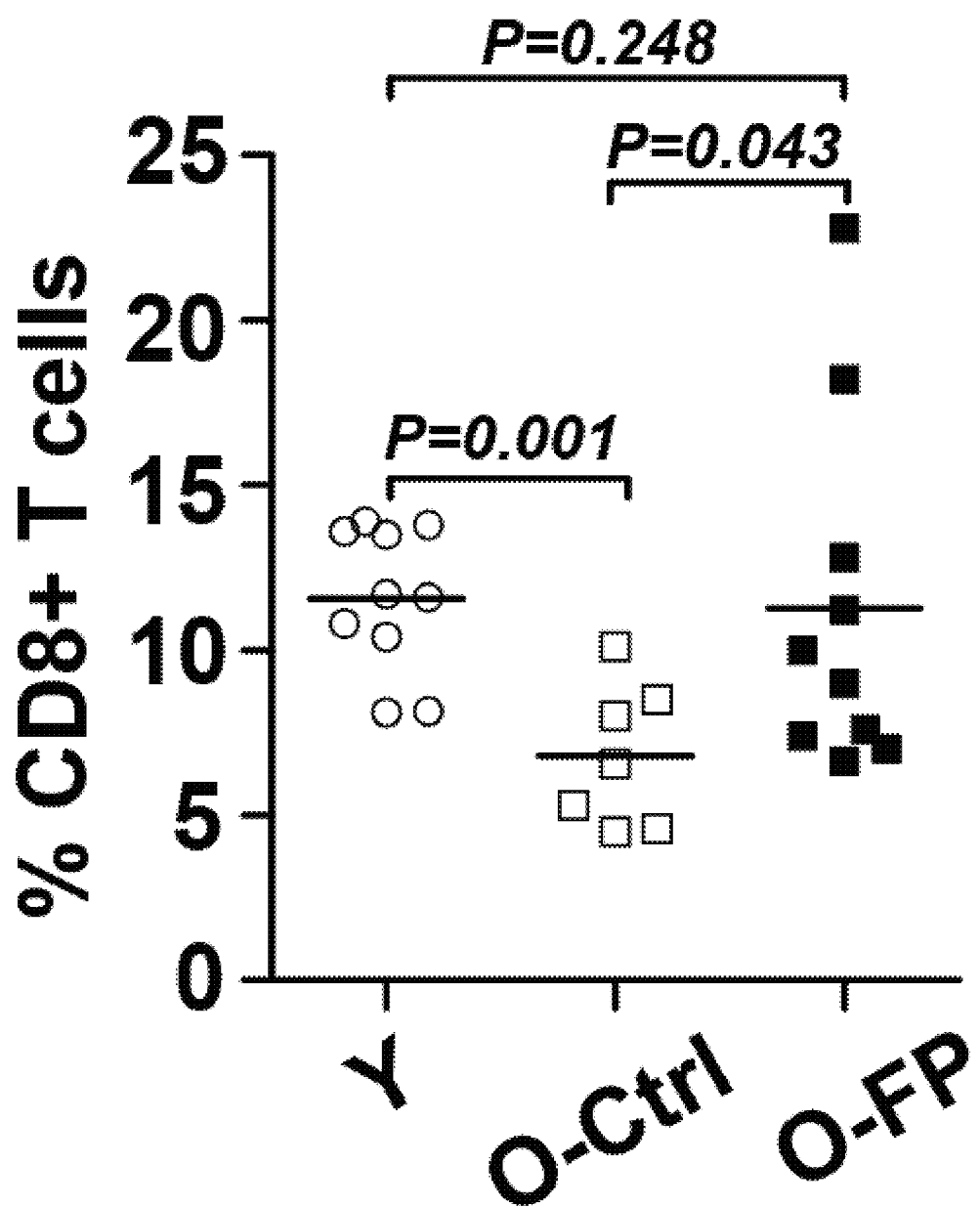
Figure 13H:
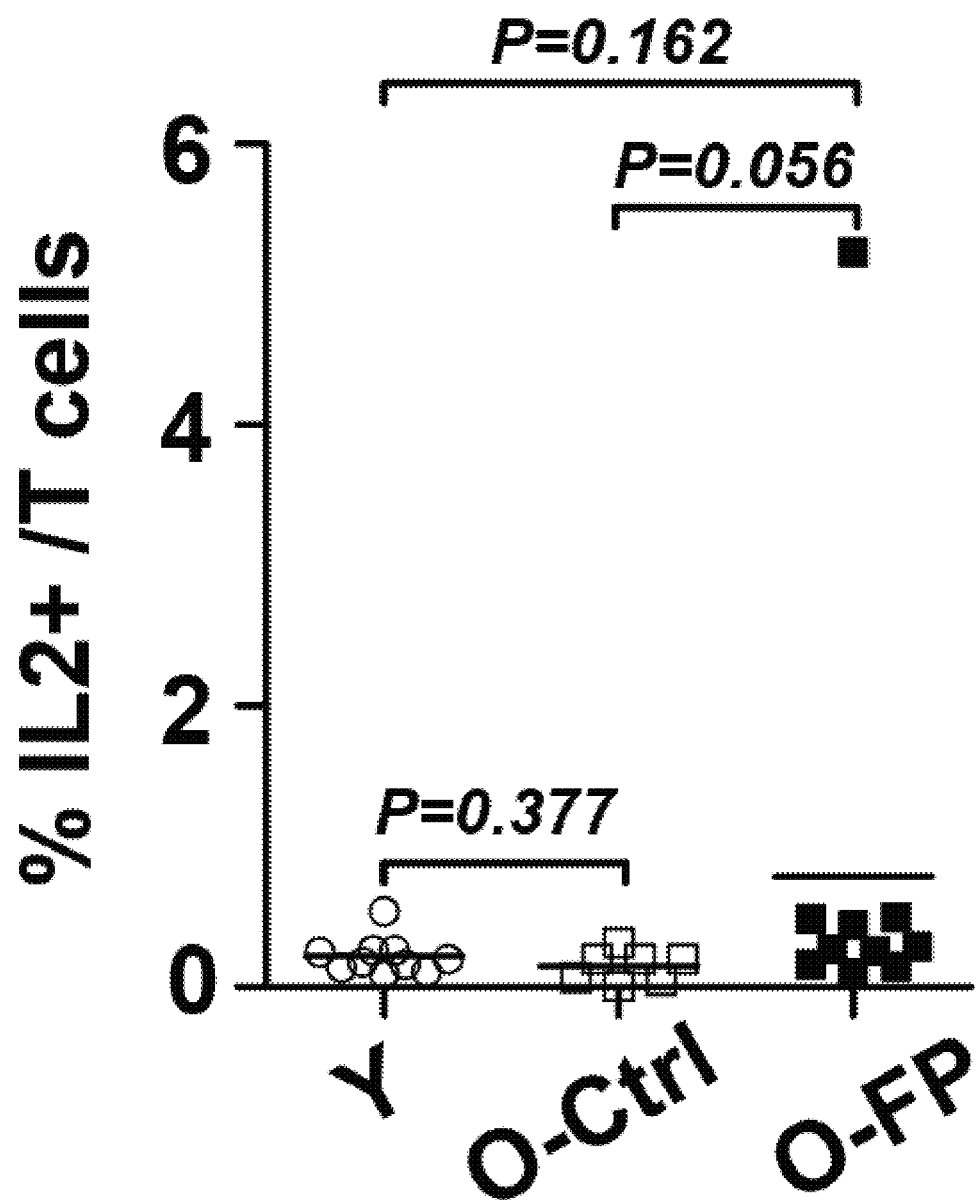
Figure 13I:
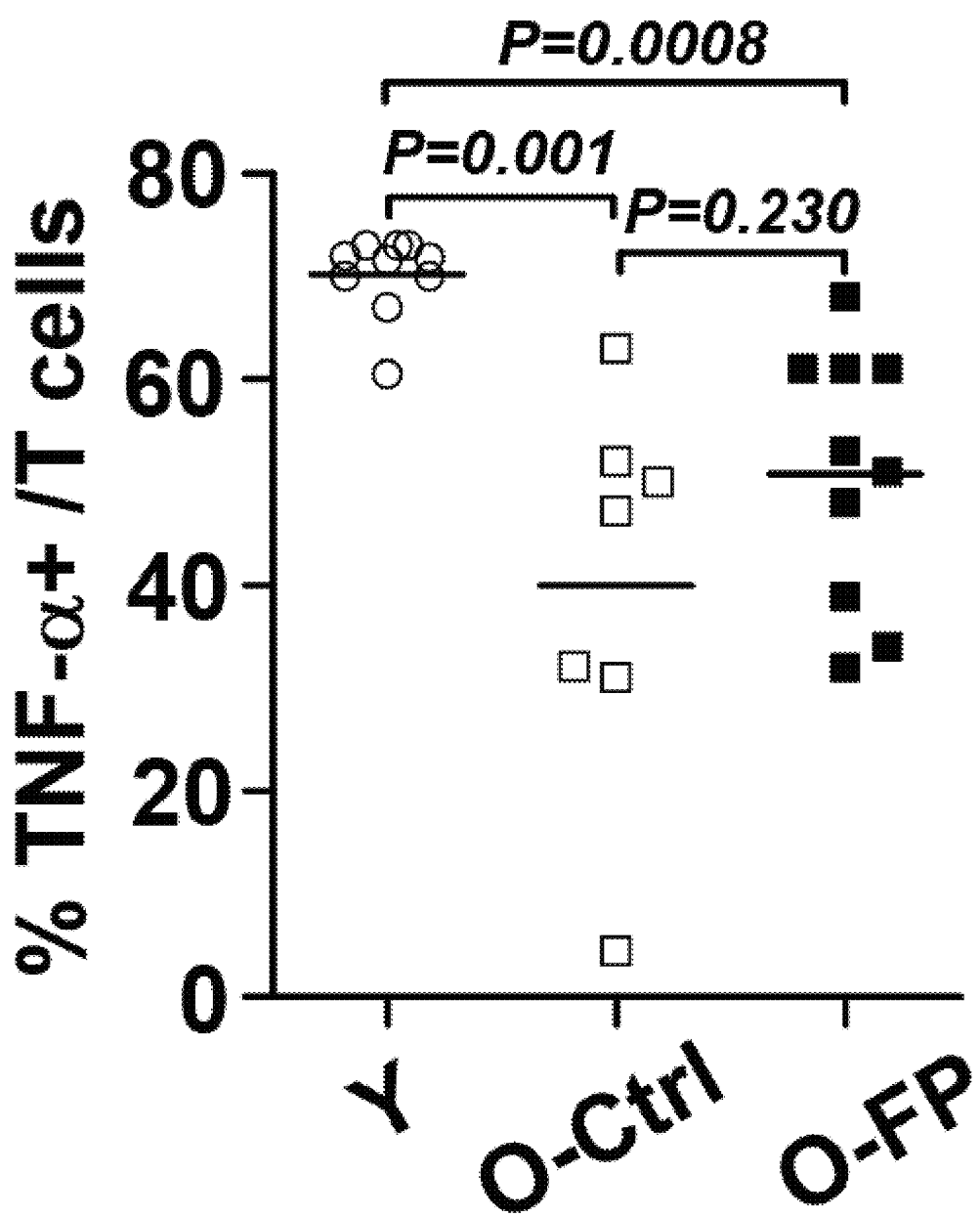
Figure 13J:
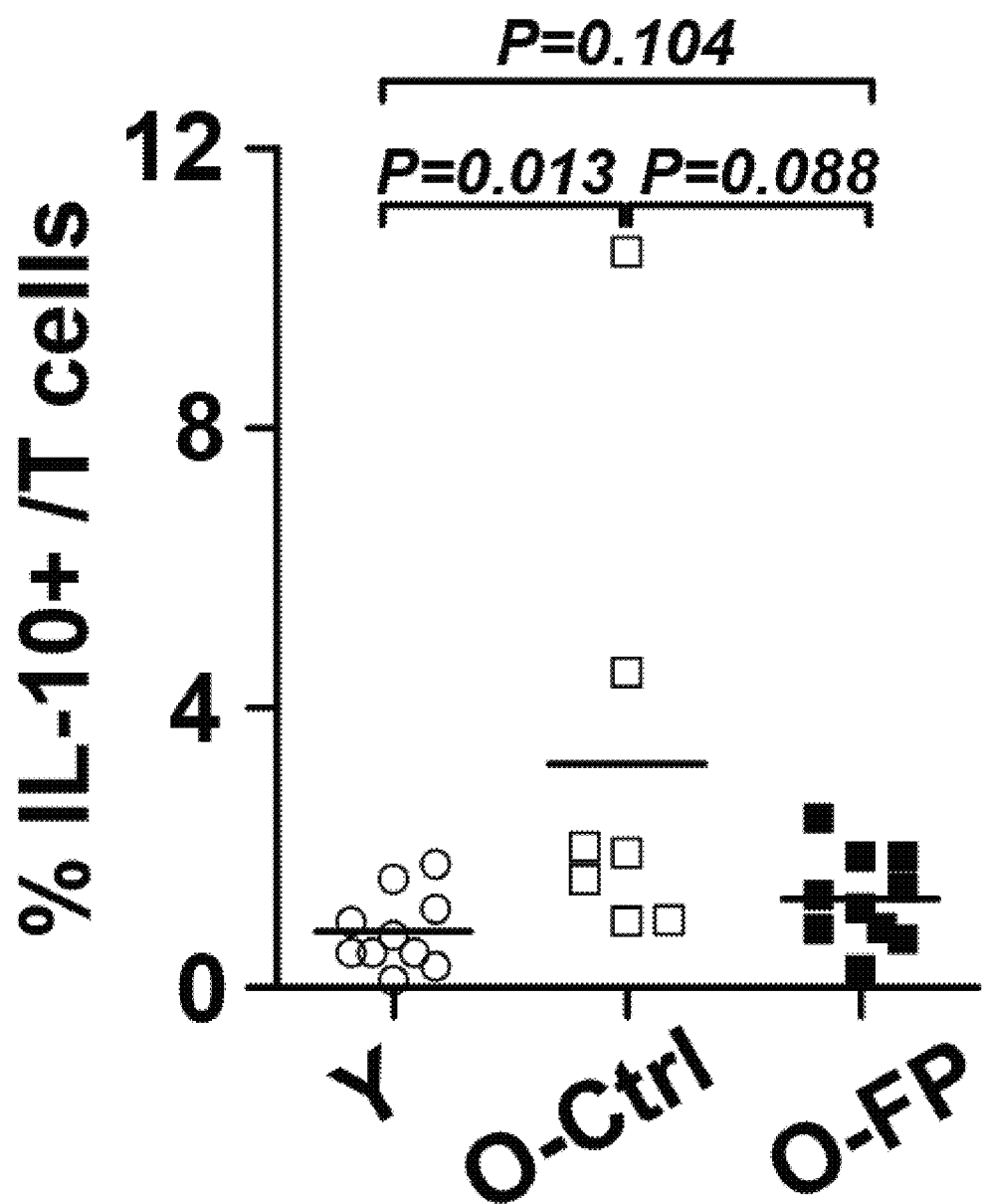
Figure 14A:
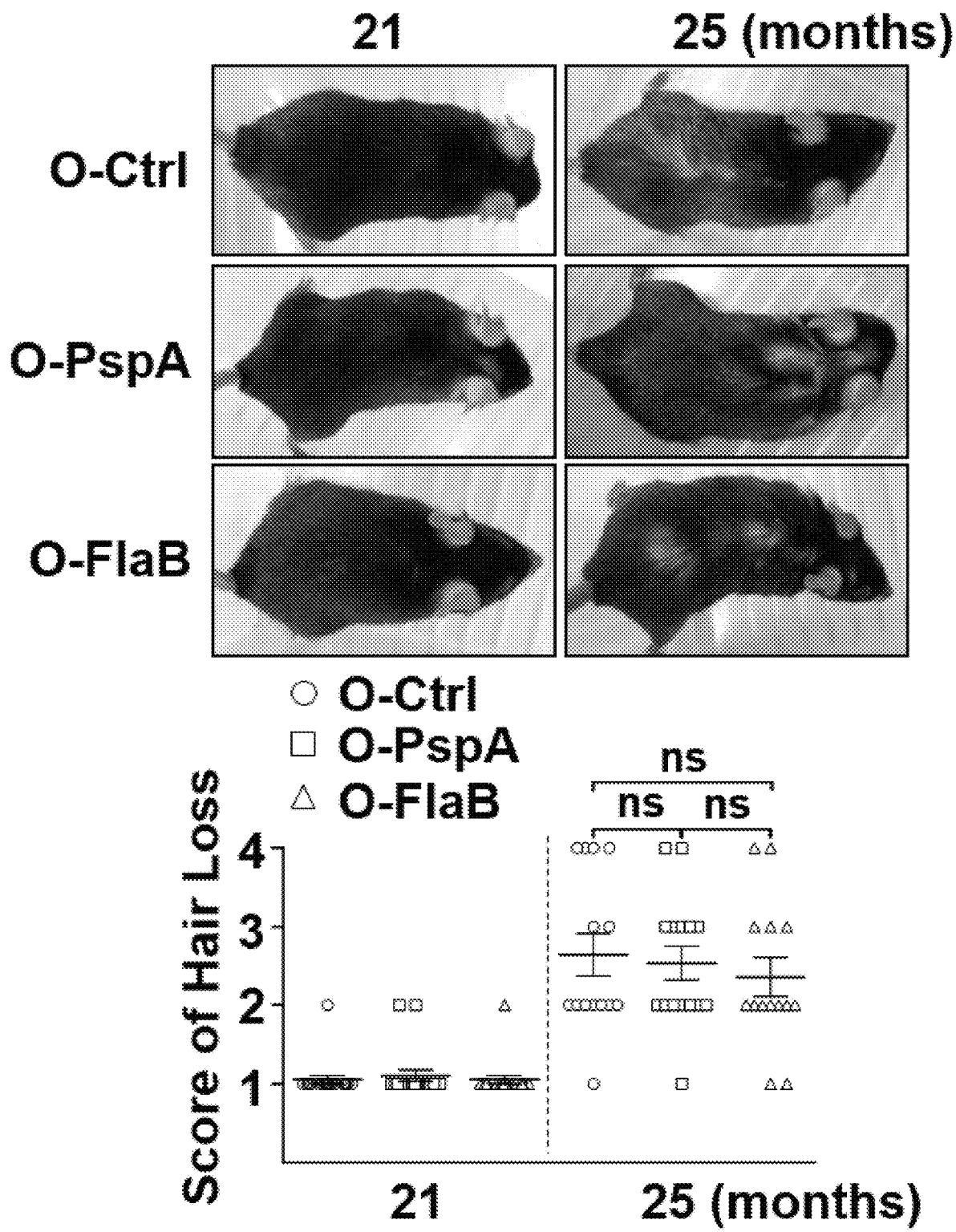
Figure 14B:
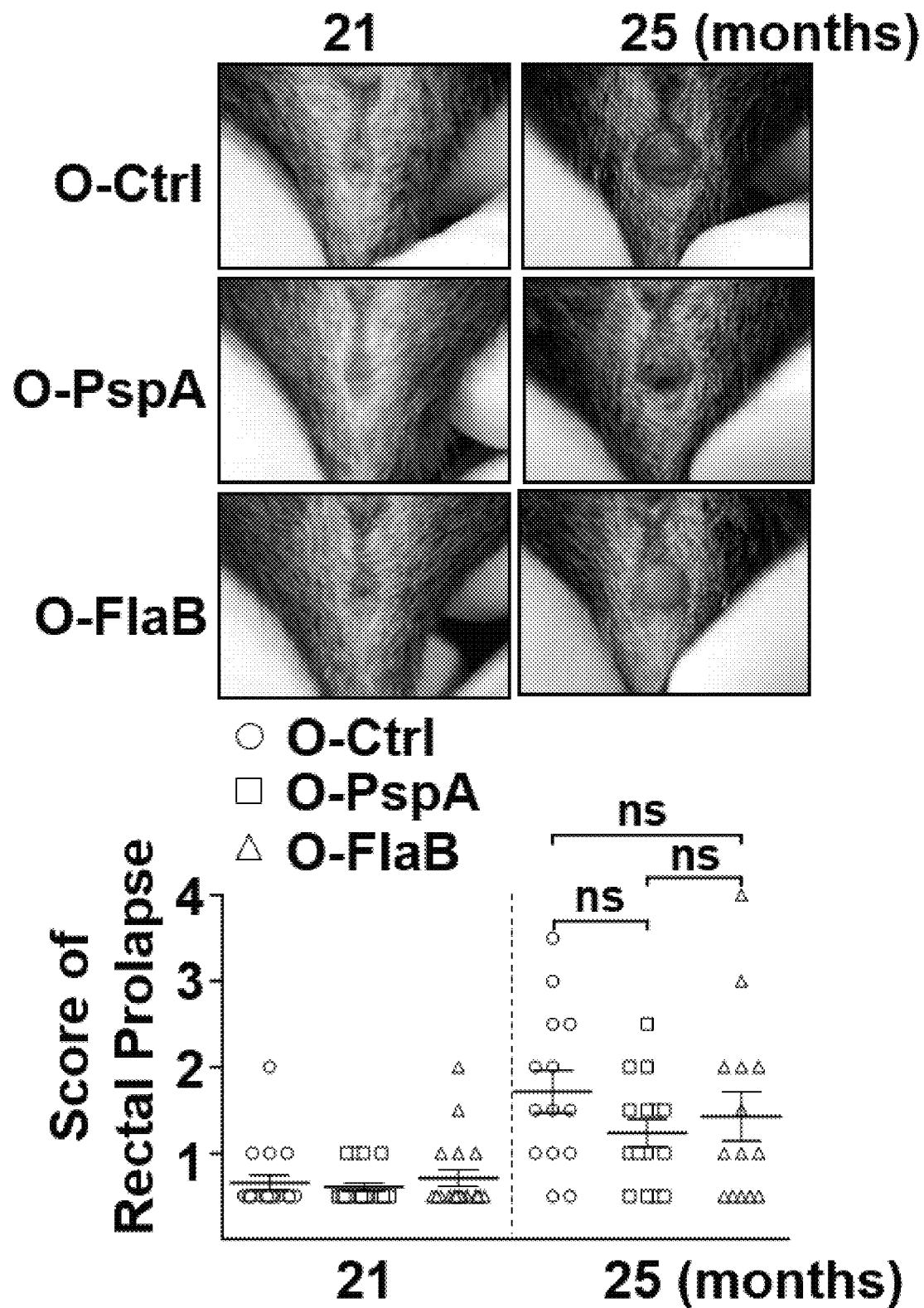
Figure 14D:
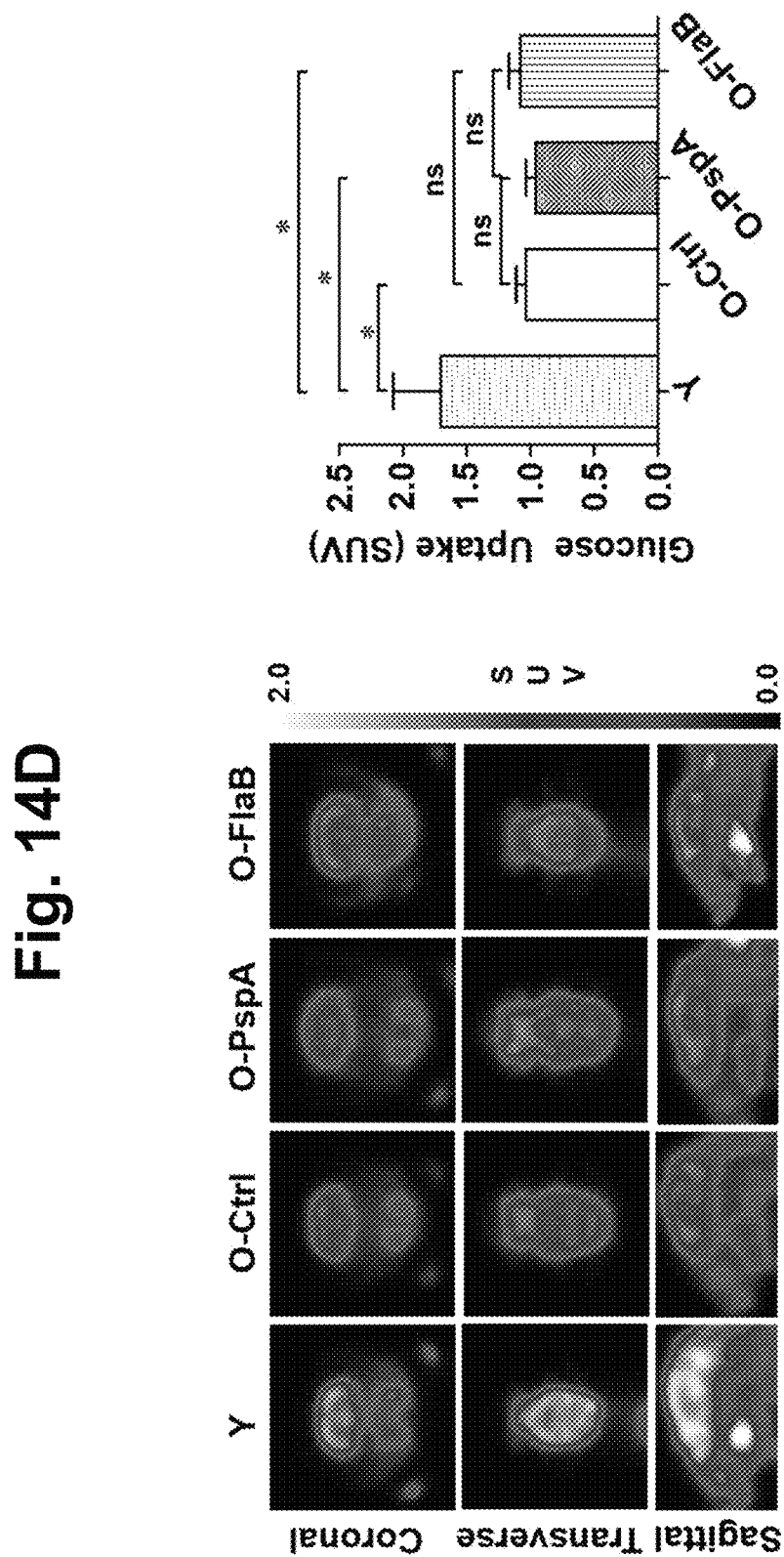

The numbers of thymocytes and bone marrow-derived hematopoietic stem cells were increased in the aged mice (FIGS. 10f and 10g).

Further, spleens of FPNI-treated aged mice preserved follicles, containing T and B cells similar to a lymph node, and revealed lower levels of aging markers, such as p53 and p16INK4a, than those in control aged mice (FIGS. 12a-12d). Broad range immunological analysis by FACS with specific markers revealed that immune surveillance-related cell populations were increased and inflammatory response-related cell populations were reduced by FPNI (FIGS. 13a-13j).

Example 13: Restoration of Locomotive and Cognitive Functions in Aged Mice after Immunization Aging is also closely associated with the decline in locomotive and cognitive functions. Since FPNI-aged mice showed more active movement than the control aged mice, we performed open field tests to investigate the effect of FPNI on the spontaneous behavior of the aged mice. Aged animals revealed a significant decrease in horizontal locomotor activities, nest building, novel object recognition and passive avoidance task compared to young mice. This reduced activity of aged mice was dramatically restored after FPNI (FIGS. 10h-10k), indicating that FPNI restores locomotive and cognitive functions of aged mice.

Taken together, it could be summarized that FPNI can extend lifespan, improve healthspan, enhance immune function and restore locomotive and cognitive capacity of aged mice.

Example 14: TLR5 Binding Moiety in the FlaB Moiety for Immunological Activation

In the next step, in order to understand the mode of action by immunological activation for longevity, we have dissected the effect of single nasal immunization with either PspA or FlaB from that of FPNI. The PspA or FlaB showed no notable effect on lifespan (data was not shown) or healthspan (FIGS. 14a-14d). Since FP was designed to target TLR5, we examined whether TLR5 was essential for FPNI-induced longevity.

TLR5 knockout mice is known to display severe inflammatory problems. Thereby, we constructed a site-directed mutation at tlr5 binding domain in the FlaB moiety (A. Verma et al., Infect Immun 73, 8237-8246 (2005)) and fused with PspA (FP SDM) (FIG. 15a). As expected, FP SDM was not able to bind with TLR5, and in consequence could not confer activation of NF-κB, a crucial transcription factor for TLR5 signaling (FIG. 15b). Nasal administration of FP, FP SDM, or vehicle was respectively initiated at 650 days of aged mice, and survival was tested. As shown in FIG. 15c, FP SDM, failed to extend lifespan. These results strongly demonstrated that TLR5 played a pivotal role in FP-mediated longevity in aged mice. These results suggested that anti-aging effector molecule should be consist of both TLR5 binding moiety and a partner antigen such as PspA for sufficient activation of immune system.

TABLE 5

| Age of animal (Months) | Immunization frequences | | Female | | |
|---|---|---|---|---|---|
| | | | Hair loss | Cataract | Rectal Prolapse |
| 21 | 0 | O-Ctrl (n = 25) | 1.36 ± 0.10 | 1.88 ± 0.23 | 1.00 ± 0.00 |
| | | O-FP (n = 25) | 1.40 ± 0.10 | 1.92 ± 0.23 | 1.00 ± 0.00 |
| | | O-FP SDM (n = 25) | 1.32 ± 0.10 | 1.92 ± 0.19 | 1.00 ± 0.00 |
| 22 | 2nd | O-Ctrl (n = 24) | 1.42 ± 0.12 | 2.25 ± 0.28 | 1.08 ± 0.06 |
| | | O-FP (n = 25) | 1.16 ± 0.07* | 1.84 ± 0.21 | 1.00 ± 0.00 |
| | | O-FP SDM (n = 25) | 1.32 ± 0.10 | 2.00 ± 0.20 | 1.04 ± 0.04 |
| 23 | 4th | O-Ctrl (n = 23) | 1.61 ± 0.14 | 2.26 ± 0.27 | 1.13 ± 0.07 |
| | | O-FP (n = 24) | 1.13 ± 0.07**, # | 2.04 ± 0.23 | 1.00 ± 0.00 |
| | | O-FP SDM (n = 25) | 1.36 ± 0.10 | 2.24 ± 0.21 | 1.12 ± 0.07 |
| 24 | 6th | O-Ctrl (n = 20) | 1.70 ± 0.16 | 2.45 ± 0.29 | 1.10 ± 0.07 |
| | | O-FP (n = 24) | 1.21 ± 0.09**, # | 2.17 ± 0.23 | 1.00 ± 0.00 |
| | | O-FP SDM (n = 23) | 1.44 ± 0.11 | 2.35 ± 0.20 | 1.13 ± 0.07 |
| 25 | 8th | O-Ctrl (n = 19) | 1.90 ± 0.17 | 2.84 ± 0.19 | 1.47 ± 0.19 |
| | | O-FP (n = 23) | 1.35 ± 0.12**, # | 2.22 ± 0.23 | 1.00 ± 0.00*, ## |
| | | O-FP SDM (n = 20) | 1.75 ± 0.16 | 2.75 ± 0.24 | 1.53 ± 0.16 |

Score: 1 (Good)~4 (Severe)
Score of mouse phenotypes is shown as mean ± SEM.
*P < 0.05; **P < 0.01, O-Ctrl vs. O-FP-immunized mice
# P < 0.05; ## P < 0.01, O-FP vs. O-FP SDM-immunized mice Example 15: TLR5-Dependent Enhancement of Intestinal Mucosal Immunity and Metabolic Activities in Aged Mice after Immunization We hypothesized that TLR5-mediated mucosal activity is vital for both maintaining overall host metabolism and avoiding harmful intestinal inflammation. We investigated TLR5-dependent enhancement of intestinal mucosal immunity as well as broad range of metabolic activities in aged mice after FPNI.

Figure 16A:
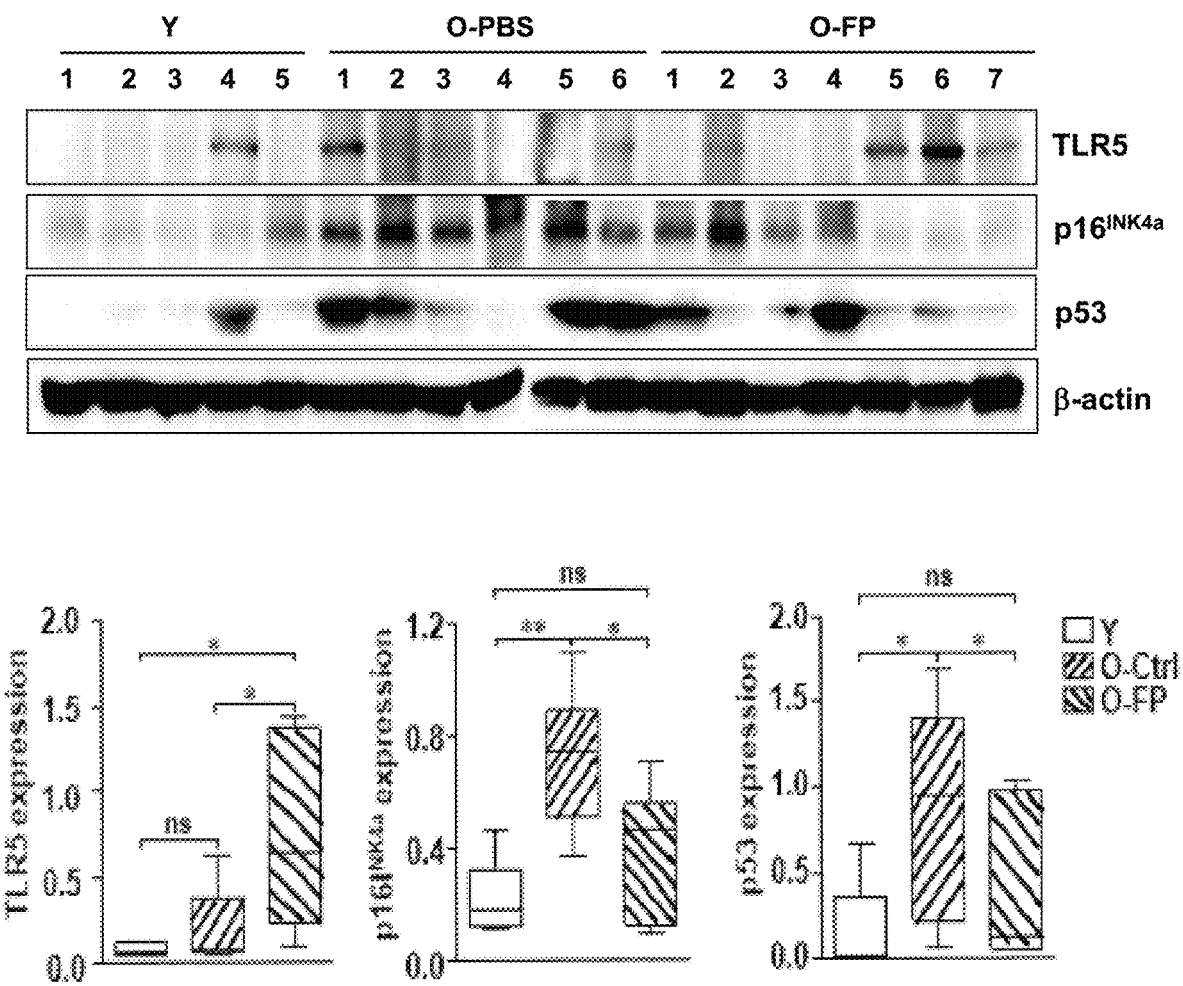
Figure 16B:
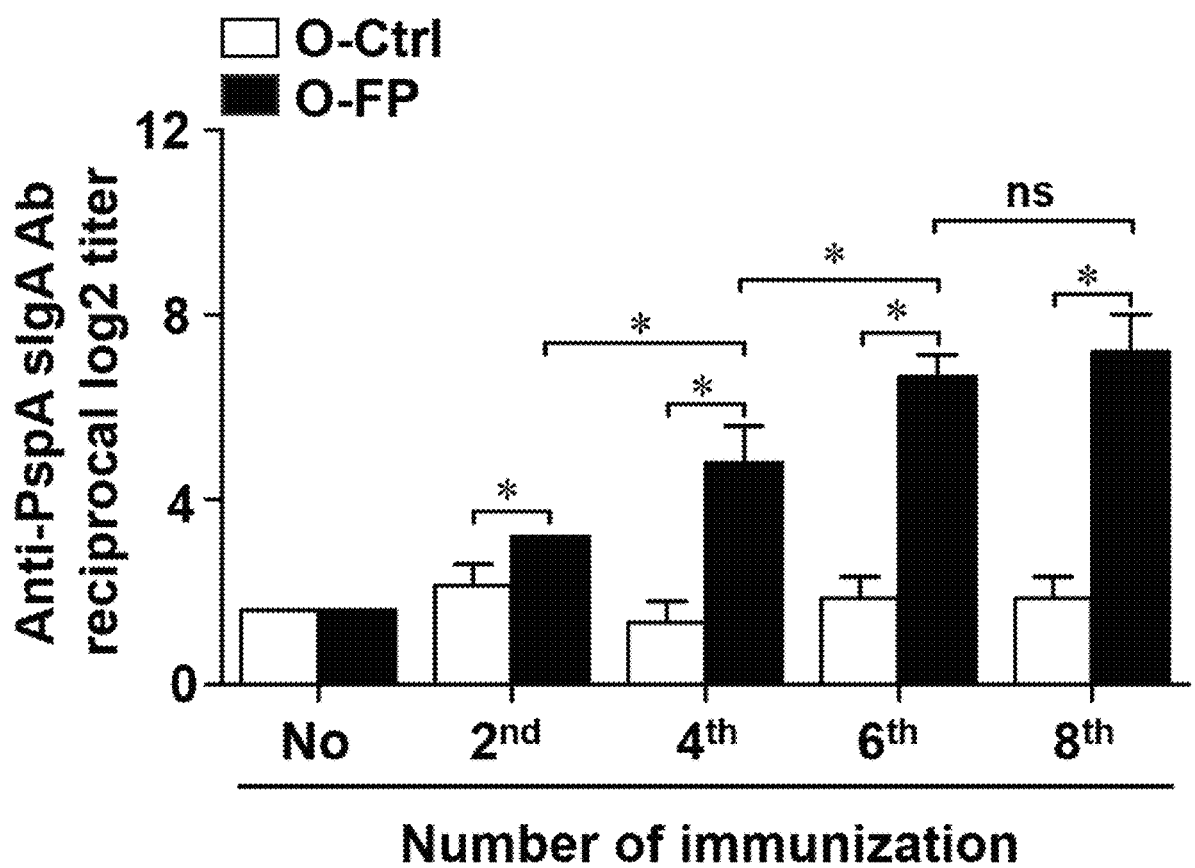

Interestingly, FPNI led to induction of TLR5 expression together with reduction of aging markers, including p53 and p16INK4a in the intestine from aged mice (FIG. 16a). It should be noted that a marker of mucosal immunity, SIgA, increased continuously in feces during FPNI, compared with control aged mice (FIG. 16b), which implicates activation of mucosal immunity by FPNI.

Figure 16C:
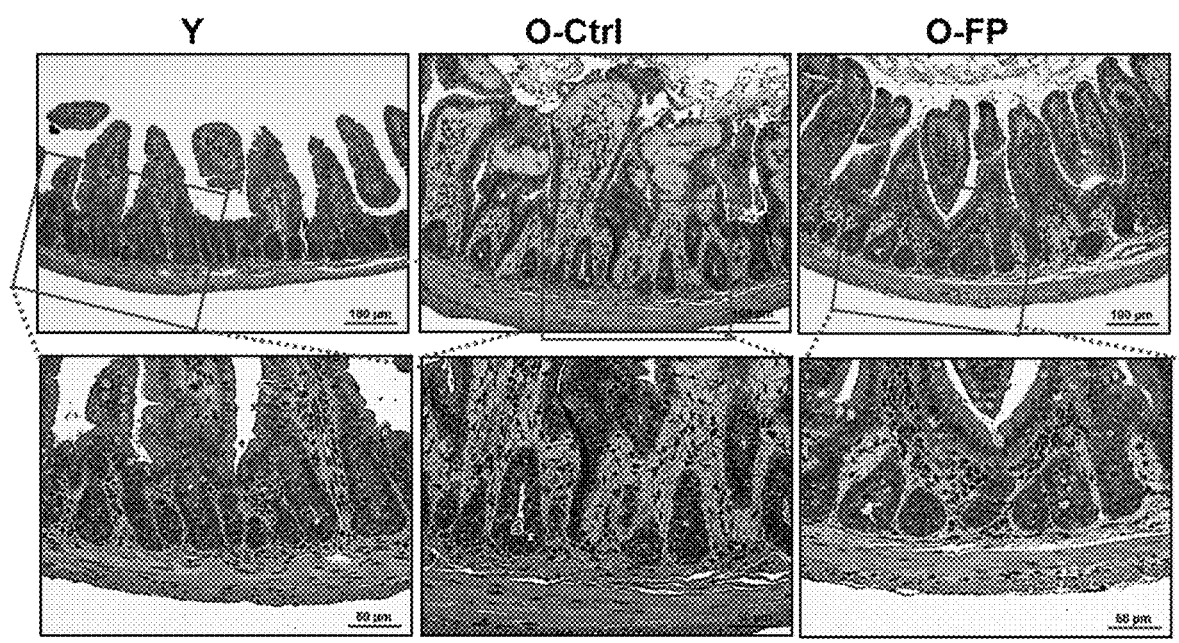
Figure 16E:
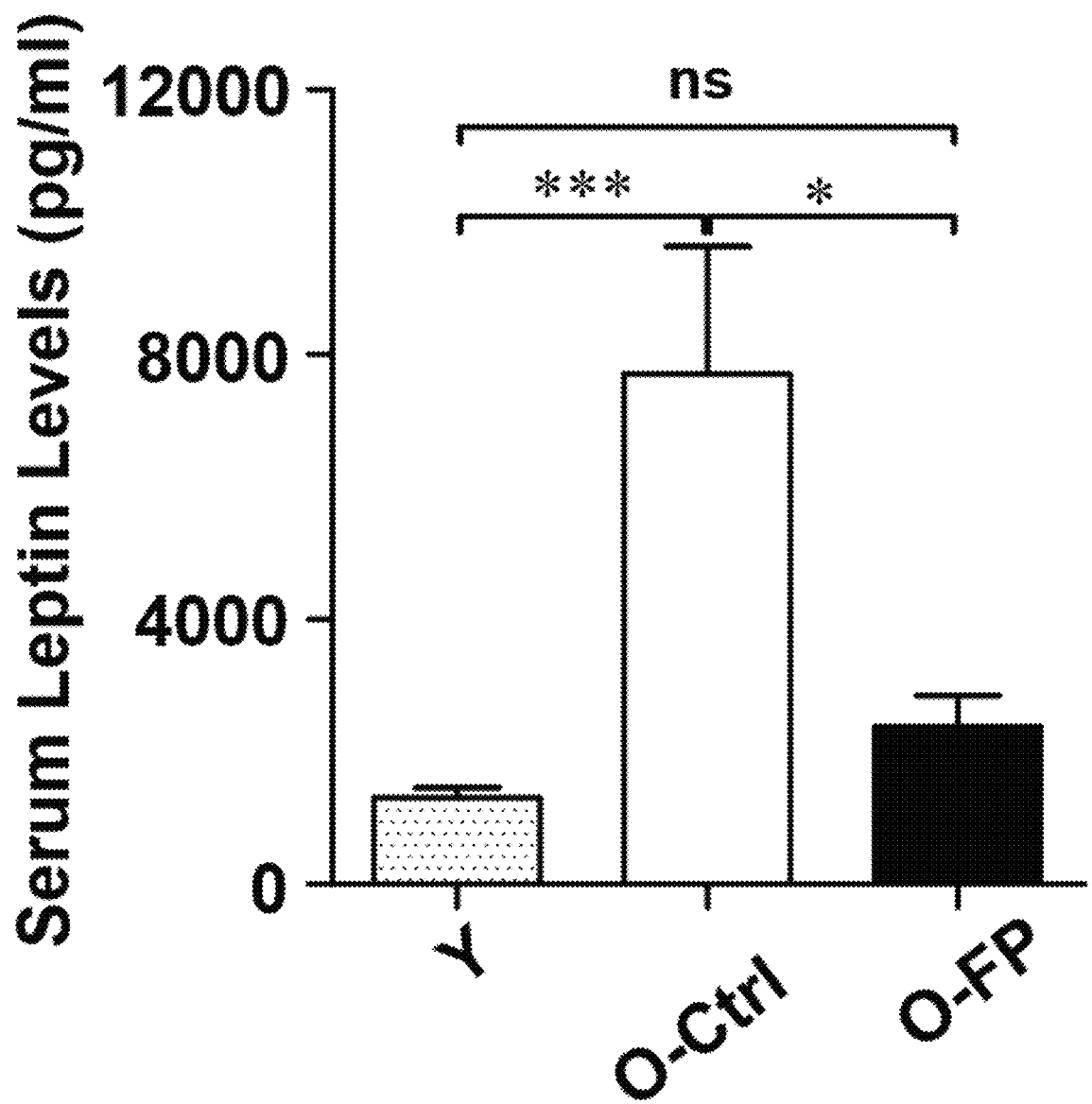
Figure 16F:
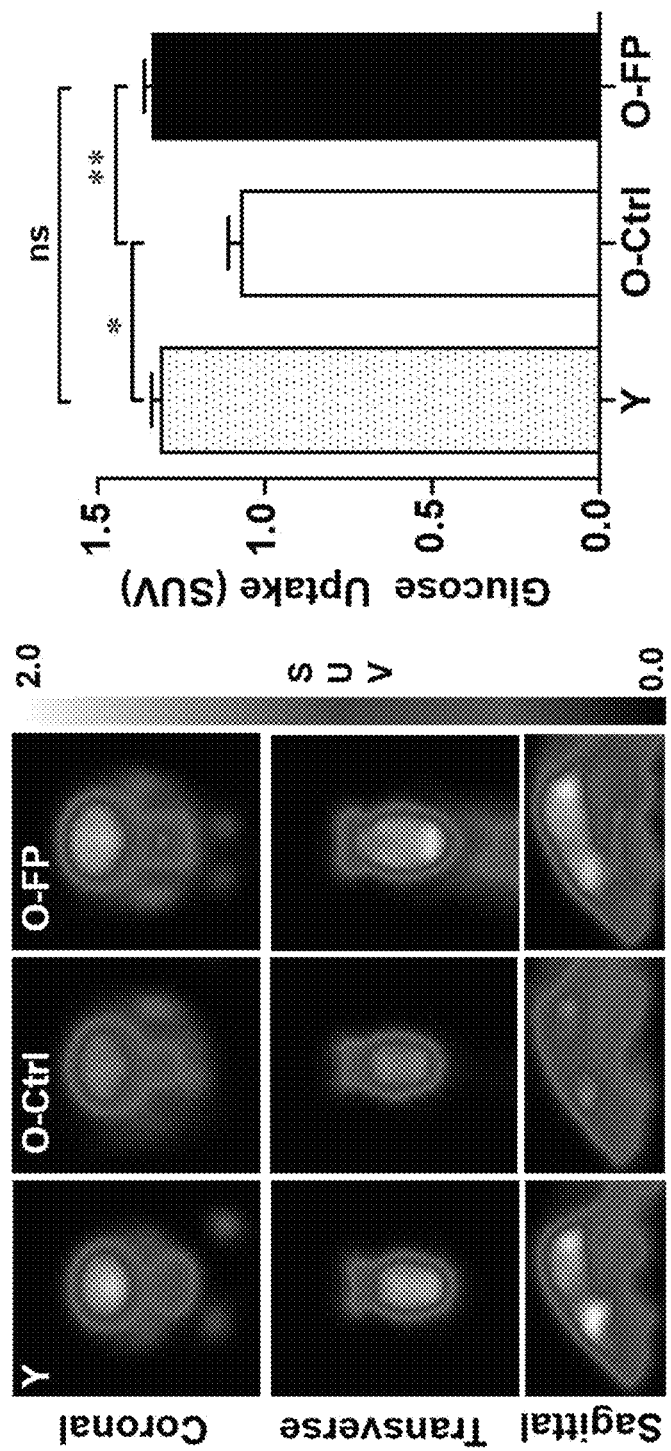
Figure 16G:
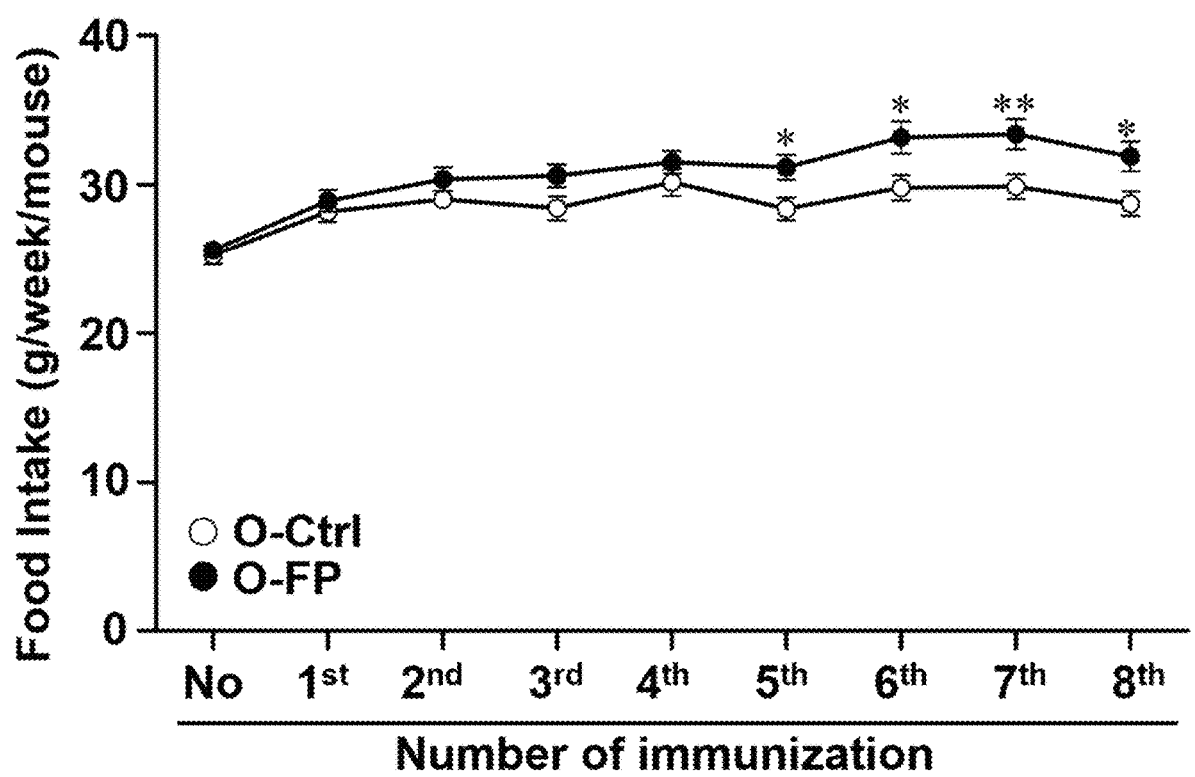

Next, we analyzed intestinal villi structures in FPNI-aged mice and found these were well preserved similar to that in young mice, i.e. small and regular size of crypt and thin epithelial layer (FIG. 16c). Rectal prolapse, a main symptom of colitis in both of TLR5-deficient mice and aging, was also remarkably prevented by FPNI (FIG. 16d). In aging mammals, increased fat mass, abdominal adiposity, and insulin resistance are frequently associated with leptin resistance and increased plasma leptin levels. We found that control aged mice showed leptin resistance with higher level of leptin in serum (FIG. 16e) in contrast to lower level of leptin in serum of FPNI-aged mice as those of young mice. To elucidate leptin-dependent metabolic activation, we measured brain glucose absorption by micro-CT and food intake after FPNI in aged mice. Interestingly, brain glucose absorption and food intake were increased without changes in total body weight during FPNI in aged mice unlike control aged mice (FIGS. 16f-16h). These results suggest that FPNI might induce more calorie consumption than their vehicle control, implying the shift in energy metabolism.

Our study showed nasal administration of FP successfully induce immunity in bronchus-associated lymphoid tissue (BALT) against to pneumococcal infection (Aging Cell (2015) 14, 907-915) as well as in GALT (gut-associated lymphoid tissue)(FIGS. 16a-16g) in aged mice through TLR5 activation. Our results (FIGS. 10a-10k; FIGS. 16a-16g; FIGS. 12a-12d; and FIGS. 13a-13j) showed TLR5-targeting mucosal vaccine FP enhanced broad range of immunity including GALT-mediated immunity and metabolic activities, leading to extension of health span.

Now we provide novel murine longevity model and demonstrated the molecular mechanism via TLR5-dependent mucosal immune stimulation.

The present study strongly demonstrates that TLR5 played an essential role in FP-mediated longevity and healthspan extension in aged mice through: prevention of hair loss, rectal prolapse and cataracts; elevating bone mineral densities in both spine and femur, and better maintained spinal curve angle; increase in the activity of bone marrow-derived stem cells; restoration of locomotive and cognitive functions; enhancing mucosal immunity, and metabolic activities.

What is claimed is:

1. A method of treating or improving an age-related disease or condition in a mammalian subject, the method comprising administering to the subject an effective amount of a composition consisting of a recombinant FlaB-PspA protein comprising the amino acid sequence of SEQ ID NO: 1 as the active ingredient, wherein the age-related disease or condition is at least one selected from the group consisting of age-related hair disease or condition, age-related skin disease or condition, age-related eye disease or condition, age-related bowel disease or condition, age-related bone disease or condition, and age-related decreased immunity, wherein the age-related hair disease or condition is at least one selected from the group consisting of hair loss, and hair discoloration, wherein the age-related skin disease or condition is reduced dermal layer of skin, wherein the age-related eye disease or condition is cataracts, wherein the age-related bowel disease or condition is rectal prolapse and/or age-related hernia, wherein the age-related bone disease or condition is kyphosis, and wherein the age-related decreased immunity is decreased level of hematopoietic stem cells and/or bone marrow-derived cells compared to a non-aged control.

2. The method of claim 1, the composition is administered mucosally.

3. The method of claim 1, the composition is pharmaceutical or food composition.

4. The method of claim 1, the composition is administered at intervals of 7 to 14 days.

5. The method of claim 1, the composition is administered more than three times.

6. The method of claim 2, wherein the administration is intranasal.

7. The method of claim 1, wherein the method is additionally for increasing the levels of secretory IgA in a subject.

8. The method of claim 1, wherein the recombinant protein is a FlaB-PspA protein consisting of the amino acid sequence of SEQ ID NO: 1.

9. The method of claim 1, wherein the mammalian subject is a human.

* * * * *

SEQUENCE LISTING

```
<160> NUMBER OF SEQ ID NOS: 11

<210> SEQ ID NO 1
<211> LENGTH: 612
<212> TYPE: PRT
<213> ORGANISM: Artificial Sequence
<220> FEATURE:
<223> OTHER INFORMATION: Synthetic Construct

<400> SEQUENCE: 1

Met Ala Val Asn Val Asn Thr Asn Val Ala Ala Met Thr Ala Gln Arg
1               5                   10                  15

Tyr Leu Asn Asn Ala Asn Ser Ala Gln Gln Thr Ser Met Glu Arg Leu
            20                  25                  30

Ser Ser Gly Phe Lys Ile Asn Ser Ala Lys Asp Asp Ala Ala Gly Leu
        35                  40                  45

Gln Ile Ser Asn Arg Leu Asn Val Gln Ser Arg Gly Leu Asp Val Ala
    50                  55                  60

Val Arg Asn Ala Asn Asp Gly Ile Ser Ile Ala Gln Thr Ala Glu Gly
65                  70                  75                  80

Ala Met Asn Glu Thr Thr Asn Ile Leu Gln Arg Met Arg Asp Leu Ser
                85                  90                  95

Leu Gln Ser Ala Asn Gly Ser Asn Ser Lys Ser Glu Arg Val Ala Ile
            100                 105                 110

Gln Glu Glu Val Thr Ala Leu Asn Asp Glu Leu Asn Arg Ile Ala Glu
        115                 120                 125

Thr Thr Ser Phe Gly Gly Asn Lys Leu Leu Asn Gly Thr Tyr Gly Thr
    130                 135                 140

Lys Ala Met Gln Ile Gly Ala Asp Asn Gly Glu Ala Val Met Leu Ser
145                 150                 155                 160

Leu Lys Asp Met Arg Ser Asp Asn Val Met Met Gly Gly Val Ser Tyr
                165                 170                 175

Gln Ala Glu Glu Gly Lys Asp Lys Asn Trp Asn Val Ala Ala Gly Asp
            180                 185                 190

Asn Asp Leu Thr Ile Ala Leu Thr Asp Ser Phe Gly Asn Glu Gln Glu
        195                 200                 205

Ile Glu Ile Asn Ala Lys Ala Gly Asp Asp Ile Glu Glu Leu Ala Thr
    210                 215                 220

Tyr Ile Asn Gly Gln Thr Asp Leu Val Lys Ala Ser Val Gly Glu Gly
225                 230                 235                 240

Gly Lys Leu Gln Ile Phe Ala Gly Asn Asn Lys Val Gln Gly Glu Ile
                245                 250                 255

Ala Phe Ser Gly Ser Leu Ala Gly Glu Leu Gly Leu Gly Glu Gly Lys
            260                 265                 270

Asn Val Thr Val Asp Thr Ile Asp Val Thr Thr Val Gln Gly Ala Gln
        275                 280                 285

Glu Ser Val Ala Ile Val Asp Ala Ala Leu Lys Tyr Val Asp Ser His
    290                 295                 300

Arg Ala Glu Leu Gly Ala Phe Gln Asn Arg Phe Asn His Ala Ile Ser
305                 310                 315                 320
```

-continued

Asn Leu Asp Asn Ile Asn Glu Asn Val Asn Ala Ser Lys Ser Arg Ile
                325                 330                 335

Lys Asp Thr Asp Phe Ala Lys Glu Thr Thr Gln Leu Thr Lys Thr Gln
            340                 345                 350

Ile Leu Ser Gln Ala Ser Ser Ile Leu Ala Gln Ala Lys Gln Ala
        355                 360                 365

Pro Asn Ser Ala Leu Ser Leu Leu Gly Val Asp Ser Pro Val Ala Ser
    370                 375                 380

Gln Ser Lys Ala Glu Lys Asp Tyr Asp Ala Ala Lys Lys Asp Ala Lys
385                 390                 395                 400

Asn Ala Lys Lys Ala Val Glu Asp Ala Gln Lys Ala Leu Asp Asp Ala
                405                 410                 415

Lys Ala Ala Gln Lys Lys Tyr Asp Glu Asp Gln Lys Lys Thr Glu Glu
            420                 425                 430

Lys Ala Ala Leu Glu Lys Ala Ala Ser Glu Glu Met Asp Lys Ala Val
        435                 440                 445

Ala Ala Val Gln Gln Ala Tyr Leu Ala Tyr Gln Ala Thr Asp Lys
    450                 455                 460

Ala Ala Lys Asp Ala Ala Asp Lys Met Ile Asp Glu Ala Lys Lys Arg
465                 470                 475                 480

Glu Glu Glu Ala Lys Thr Lys Phe Asn Thr Val Arg Ala Met Val Val
                485                 490                 495

Pro Glu Pro Glu Gln Leu Ala Glu Thr Lys Lys Ser Glu Ala
            500                 505                 510

Lys Gln Lys Ala Pro Glu Leu Thr Lys Lys Leu Glu Glu Ala Lys Ala
        515                 520                 525

Lys Leu Glu Glu Ala Glu Lys Lys Ala Thr Glu Ala Lys Gln Lys Val
    530                 535                 540

Asp Ala Glu Glu Val Ala Pro Gln Ala Lys Ile Ala Glu Leu Glu Asn
545                 550                 555                 560

Gln Val His Arg Leu Glu Gln Glu Leu Lys Glu Ile Asp Glu Ser Glu
                565                 570                 575

Ser Glu Asp Tyr Ala Lys Glu Gly Phe Arg Ala Pro Leu Gln Ser Lys
            580                 585                 590

Leu Asp Ala Lys Lys Ala Lys Leu Ser Lys Leu Glu Glu Leu Ser Asp
        595                 600                 605

Lys Ile Asp Glu
    610

<210> SEQ ID NO 2
<211> LENGTH: 612
<212> TYPE: PRT
<213> ORGANISM: Artificial Sequence
<220> FEATURE:
<223> OTHER INFORMATION: Synthetic Construct

<400> SEQUENCE: 2

Met Ala Val Asn Val Asn Thr Asn Val Ala Ala Met Thr Ala Gln Arg
1               5                   10                  15

Tyr Leu Asn Asn Ala Asn Ser Ala Gln Gln Thr Ser Met Glu Arg Leu
            20                  25                  30

Ser Ser Gly Phe Lys Ile Asn Ser Ala Lys Asp Asp Ala Ala Gly Leu
        35                  40                  45

Gln Ile Ser Asn Arg Leu Asn Val Gln Ser Arg Gly Leu Asp Val Ala
    50                  55                  60

-continued

```
Val Arg Asn Ala Asn Asp Gly Ile Ser Ile Ala Gln Thr Ala Glu Gly
 65                  70                  75                  80

Ala Met Asn Glu Thr Thr Asn Ile Leu Gln Arg Ala Arg Asp Ala Ser
             85                  90                  95

Leu Gln Ser Ala Asn Gly Ser Asn Ser Lys Ser Glu Arg Val Ala Ile
            100                 105                 110

Gln Glu Glu Val Thr Ala Leu Asn Asp Glu Leu Asn Arg Ile Ala Glu
        115                 120                 125

Thr Thr Ser Phe Gly Gly Asn Lys Leu Leu Asn Gly Thr Tyr Gly Thr
    130                 135                 140

Lys Ala Met Gln Ile Gly Ala Asp Asn Gly Glu Ala Val Met Leu Ser
145                 150                 155                 160

Leu Lys Asp Met Arg Ser Asp Asn Val Met Met Gly Gly Val Ser Tyr
                165                 170                 175

Gln Ala Glu Glu Gly Lys Asp Lys Asn Trp Asn Val Ala Ala Gly Asp
            180                 185                 190

Asn Asp Leu Thr Ile Ala Leu Thr Asp Ser Phe Gly Asn Glu Gln Glu
        195                 200                 205

Ile Glu Ile Asn Ala Lys Ala Gly Asp Asp Ile Glu Glu Leu Ala Thr
    210                 215                 220

Tyr Ile Asn Gly Gln Thr Asp Leu Val Lys Ala Ser Val Gly Glu Gly
225                 230                 235                 240

Gly Lys Leu Gln Ile Phe Ala Gly Asn Asn Lys Val Gln Gly Glu Ile
                245                 250                 255

Ala Phe Ser Gly Ser Leu Ala Gly Glu Leu Gly Leu Gly Glu Gly Lys
            260                 265                 270

Asn Val Thr Val Asp Thr Ile Asp Val Thr Thr Val Gln Gly Ala Gln
        275                 280                 285

Glu Ser Val Ala Ile Val Asp Ala Ala Leu Lys Tyr Val Asp Ser His
    290                 295                 300

Arg Ala Glu Leu Gly Ala Phe Gln Asn Arg Phe Asn His Ala Ile Ser
305                 310                 315                 320

Asn Leu Asp Asn Ile Asn Glu Asn Val Asn Ala Ser Lys Ser Arg Ile
                325                 330                 335

Lys Asp Thr Asp Phe Ala Lys Glu Thr Thr Gln Leu Thr Lys Thr Gln
            340                 345                 350

Ile Leu Ser Gln Ala Ser Ser Ile Leu Ala Gln Ala Lys Gln Ala
        355                 360                 365

Pro Asn Ser Ala Leu Ser Leu Leu Gly Val Asp Ser Pro Val Ala Ser
    370                 375                 380

Gln Ser Lys Ala Glu Lys Asp Tyr Asp Ala Ala Lys Lys Asp Ala Lys
385                 390                 395                 400

Asn Ala Lys Lys Ala Val Glu Asp Ala Gln Lys Ala Leu Asp Asp Ala
                405                 410                 415

Lys Ala Ala Gln Lys Lys Tyr Asp Glu Asp Gln Lys Lys Thr Glu Glu
            420                 425                 430

Lys Ala Ala Leu Glu Lys Ala Ala Ser Glu Glu Met Asp Lys Ala Val
        435                 440                 445

Ala Ala Val Gln Gln Ala Tyr Leu Ala Tyr Gln Gln Ala Thr Asp Lys
    450                 455                 460

Ala Ala Lys Asp Ala Ala Asp Lys Met Ile Asp Glu Ala Lys Lys Arg
465                 470                 475                 480

Glu Glu Glu Ala Lys Thr Lys Phe Asn Thr Val Arg Ala Met Val Val
```

485                 490                 495
Pro Glu Pro Glu Gln Leu Ala Glu Thr Lys Lys Lys Ser Glu Glu Ala
            500                 505                 510
Lys Gln Lys Ala Pro Glu Leu Thr Lys Lys Leu Glu Glu Ala Lys Ala
        515                 520                 525
Lys Leu Glu Glu Ala Glu Lys Lys Ala Thr Glu Ala Lys Gln Lys Val
    530                 535                 540
Asp Ala Glu Glu Val Ala Pro Gln Ala Lys Ile Ala Glu Leu Glu Asn
545                 550                 555                 560
Gln Val His Arg Leu Glu Gln Glu Leu Lys Glu Ile Asp Glu Ser Glu
                565                 570                 575
Ser Glu Asp Tyr Ala Lys Glu Gly Phe Arg Ala Pro Leu Gln Ser Lys
            580                 585                 590
Leu Asp Ala Lys Lys Ala Lys Leu Ser Lys Leu Glu Glu Leu Ser Asp
        595                 600                 605
Lys Ile Asp Glu
    610

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Leu Gln Arg Ile Arg Asp Leu Ala Leu Gln
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Leu Gln Arg Met Arg Asp Leu Ser Leu Gln
1               5                   10

<210> SEQ ID NO 5
<211> LENGTH: 28
<212> TYPE: DNA
<213> ORGANISM: Artificial Sequence
<220> FEATURE:
<223> OTHER INFORMATION: Synthetic Construct

<400> SEQUENCE: 5
gaattcatgg cagtgaatgt aaatacaa                                      28

<210> SEQ ID NO 6
<211> LENGTH: 31
<212> TYPE: DNA
<213> ORGANISM: Artificial Sequence
<220> FEATURE:
<223> OTHER INFORMATION: Synthetic Construct

<400> SEQUENCE: 6
ttgtagagat gcgtcacgcg cacgttgtag g                                  31

<210> SEQ ID NO 7
<211> LENGTH: 31

```
<212> TYPE: DNA
<213> ORGANISM: Artificial Sequence
<220> FEATURE:
<223> OTHER INFORMATION: Synthetic Construct

<400> SEQUENCE: 7
cctacaacgt gcgcgtgacg catctctaca a                               31

<210> SEQ ID NO 8
<211> LENGTH: 27
<212> TYPE: DNA
<213> ORGANISM: Artificial Sequence
<220> FEATURE:
<223> OTHER INFORMATION: Synthetic Construct

<400> SEQUENCE: 8
ctgcagttag cctagtagac ttagcgc                                    27

<210> SEQ ID NO 9
<211> LENGTH: 30
<212> TYPE: DNA
<213> ORGANISM: Artificial Sequence
<220> FEATURE:
<223> OTHER INFORMATION: Synthetic Construct

<400> SEQUENCE: 9
ctacaacgta tgcgtgacct atctctacaa                                 30

<210> SEQ ID NO 10
<211> LENGTH: 30
<212> TYPE: DNA
<213> ORGANISM: Artificial Sequence
<220> FEATURE:
<223> OTHER INFORMATION: Synthetic Construct

<400> SEQUENCE: 10
ctacaacgtg cgcgtgacgc atctctacaa                                 30

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

Leu Gln Arg Ala Arg Asp Ala Ser Leu Gln
1               5                   10
```